United States Patent
Kirchgessner et al.

(10) Patent No.: US 7,235,375 B2
(45) Date of Patent: Jun. 26, 2007

(54) ORGANIC ANION TRANSPORT PROTEINS

(75) Inventors: Todd G. Kirchgessner, North Wales, PA (US); Bonnie Hsiang, Trenton, NJ (US); Yingjie Zhu, Killingworth, CT (US); Yuli Wu, Newtown, PA (US); Zhaoging Wang, Piscataway, NJ (US); Jean S. Lynch, Ringoes, NJ (US); Xin Huang, Cranbury, NJ (US); Wen-Pin Yang, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 213 days.

(21) Appl. No.: 10/736,936

(22) Filed: Dec. 16, 2003

(65) Prior Publication Data

US 2004/0132135 A1 Jul. 8, 2004

Related U.S. Application Data

(62) Division of application No. 09/575,081, filed on May 19, 2000, now Pat. No. 6,692,934.

(60) Provisional application No. 60/135,081, filed on May 20, 1999.

(51) Int. Cl.
| | |
|---|---|
| G01N 33/567 | (2006.01) |
| G01N 33/53 | (2006.01) |
| A61K 49/00 | (2006.01) |
| A61B 10/00 | (2006.01) |
| C01P 21/06 | (2006.01) |
| C07K 1/00 | (2006.01) |

(52) U.S. Cl. ............... 435/7.21; 435/7.2; 435/7.8; 435/455; 435/69.1; 436/503; 424/9.2; 424/9.6; 530/350

(58) Field of Classification Search ............... None
See application file for complete search history.

(56) References Cited

FOREIGN PATENT DOCUMENTS

| WO | WO9517905 | 7/1995 |
| WO | WO9731111 | 8/1997 |

OTHER PUBLICATIONS

NCBI Entrez Accession No. L19031 (gi:410310), Jacquemin, et al., Mar. 4, 1994.
NCBI Entrez Accession No. P46720 (gi:1171883), Jacquemin, et al., May 1, 2005.
NCBI Entrez Accession No. P46721 (gi:1171882), Kullak-Ublick, et al., May 1, 2005.
NCBI Entrez Accession No. T55488 (gi:657349), Hillier, et al., Feb. 6, 1995.
NCBI Entrez Accession No. U21943 (gi:885977), Kullak-Ublick, et al., Feb. 16, 1996.
NCBI Entrez Accession No. T73863 (gi:690538), Wilson, R.K., Mar. 2, 1995.
NCBI Entrez Accession No. AI027850 (gi:3246549), Strausberg, R., Oct. 30, 1998.
Chen, et al. "Identification of two *hERR2*-related novel nuclear receptors utilizing bioinformatics and inverse PCR", Gene, vol. 228, pp. 101-109 (1999).
Hagenbuch, B., et al., Proc. Natl. Acad. Sci. vol. 88, Dec. 1991 pp. 10629-10633.
Hagenbuch,B., et al., The American Society for Clinical Investigation, Inc. vol. 93, Mar. 1994, pp. 1326-1331.
Meier, P.J., et al., Hepatology vol. 26, No. 6, 1997, pp. 1667-1677.
Jacquemin, E., et al., Proc. Natl. Acad. Sci. vol. 91, Jan. 1994, pp. 133-137.
Noe, B.A., et al., Proc. Nat; Acad. Sci. vol. 94, Sep. 1997, pp. 10346-10350.
Abe, T., et al. , J. Biol. Chem. vol. 273, No. 18, (1998), pp. 11395-11401.
Bossuyt, X., et al., J. Pharmacol. Exp. Ther. vol. 276, (1996), pp. 891-896.
Bossuyt, X., et al., J. Hepatol. vol. 25, (1996) pp. 733-738.
Kanai, N., et al., Am. J. Physiol. vol. 270, (1996) pp. F319-F325.
Kanai, N., et al., Am. J. Physiol. vol. 270, (1996), pp. F326-F331.
Kontaxi, M., et al., J. Pharmacol. Exp. Ther. vol. 279, (1996), pp. 1507-1513.
Li, L., et al., J. Biol. Chem. vol. 273, No. 26, (1998), pp. 16184-16191.
Kullak-Ublick, G.A., et al., Gastroenterology vol. 109, No. 4, (1995), pp. 1274-1282.
Kullak-Ublick, G.A., et al., Hepatology vol. 20, No. 2, (1994), pp. 441-416.
Kullak-Ublick, G.A., et al., FEBS Lett., vol. 424, (1998), pp. 173-176.
Wolkoff, A.W., Semin. Liver Dis., vol. 16, No. 2, (1996), pp. 121-127.
Abe, T., et al., J. Biol. Chem., vol. 273, No. 35 (1998), pp. 22395-22401.

*Primary Examiner*—Olga N. Chernyshev
(74) *Attorney, Agent, or Firm*—Bristol-Myers Squibb Patent Department

(57) ABSTRACT

The current invention discloses nucleic acid and amino acid sequences for novel organic anion transfer proteins ("OATPs"). The invention encompasses the OATPs described herein, together with vectors containing the cDNA sequences, host cells containing the vectors and polypeptides having all or part of an OATP. Also encompasses are uses for OATPs for targeting drugs to specific organs and for modulating the concentration of endogenous substrates.

1 Claim, 8 Drawing Sheets

Tissue Key

H: heart
B: brain
P: placenta
L: lung
Lv: liver
Sm: skeletal muscle
K: kidney
Pn: pancreas
S: spleen
Ty: thymus
Pr: prostate
T: testis
O: ovary
Si: small intestine
C: colon
Bl: peripheral blood leukocytes

FIG. 3A

```
                1                                                               80
roatp2          ..........  ..........  ..........  ..........  ..........  ..........  ..........  ..........
roatp3          ..........  ..........  ..........  ..........  ..........  ..........  ..........  ..........
rOAT-K1         ..........  ..........  ..........  ..........  ..........  ..........  ..........  ..........
roatp1          ..........  ..........  ..........  ..........  ..........  ..........  ..........  ..........
hOATP           ..........  ..........  ..........  ..........  ..........  ..........  ..........  ..........
hOATP-RP5       ..........  ..........  ..........  ..........  ..........  ..........  ..........  ..........
hOATP2          ..........  ..........  ..........  ..........  ..........  ..........  ..........  ..........
hOATP3          ..........  ..........  ..........  ..........  ..........  ..........  ..........  ..........
hPGT            ..........  ..........  ..........  ..........  ..........  ..........  ..........  ..........m
hOATP-RP2       mdegtglqpg  ageqleapat  aeavqercep  etlrsksIpv  lssascrpsl  sptsgdanpa  fgcvdssghq  elkqgpnpla
hOATP-RP4       ..........  ..........  mplhqlgdkp  ltfpspnsam  engldhtpps  rraspgtpls  pgslrsaahs  pldtskqplc
hOATP-RP1       ----------  ----------  ----------  ----------  ----------  ----------  ----------  ----------
Cons nsus       ----------  ----------  ----------  ----------  ----------  ----------  ----------  ----------

81                                                              160
roatp2          .........m  G.........  ........k   sEkrvAthg.  .vrCFakIkm  FLLAltcAyv  sksLs.GtYM  nSmLTQIERq
roatp3          .........m  G.........  .........e  tEkrvAthe.  .vrCFskIkm  FLLAltwAyv  sqsLs.GiYM  ntmLTQIERq
rOAT-K1         .........m  G.........  ........d   lEkgaAthg.  .agCFakIKv  FLmALtcAyv  sksLs.GtfM  sSmLTQIERq
roatp1          .........m  e.........  .........e  tEkkiAtqe.  .grlFskmKv  FLLsLtcAcl  tksLs.GvYM  nSmLTQIERq
hOATP           .........m  G.........  .........e  tEkriethr.  .irClsklKm  FLLAitcAfv  sktLs.GsYM  nSmLTQIERq
hOATP-RP5       dtsskeniql  fcktsvq.pv Gr.....psfk tEypsseek.  .qpCcgelKv  FLcALsfvyf  akaLa.egYl  kStiTQIERR
hOATP2          .........   ..mdqng.hl n.......kt aEaqpsenkk  .trycnglKm  FLaALslsfi  aktlg.aiiM  kSsiihIERR
hOATP3          mqgkkpggss  gggrsge.lq G........de aqrnkkkkkk .vsCFsnIKi FLvsecalml aqgtv.GaYl  vSvLTtlERR
hPGT            ..........mg  llpklgv.sq G........sd tstsrAgrca .rsvFgnIKv FvLcgglIql cqlLy.sayf  kSsLTtiEkR
hOATP-RP2       ..........   .mgtent.pg  G........k  aspdpqdvr.  .psvFhnIKl  FvLchsllql  aqlmi.sgYl  kSsistvEkR
hOATP-RP4       pspsapstsa  glgdcnh.rv  dlsktfsvss  alamlqerrc  lyvvltdsrc  FLvcmcfltf  iqalmvsgYl  sSviTTIERR
hOATP-RP1       qlwaekhgar  gthevryxsa  G.......qsv acgwwAfapp clqvlntpKg  iLfflcaAaf  lqgmtvngfi  ntviTslERR
Cons nsus       ----------  G---------  ----------  -----E----A-----  --CF--IK-   FLLAL--A--  ----L--G-YM  -S-LTQIERR
```

```
              161                                                                                   240
roatp2      FgIptSiVGL InGSFEIGNL LLIiFVSYFG tKLHRPimIG vGCavMGLGc fLisLPHFLM GqYEYEt... ilptsNvsSn
roatp3      FdIpiSiVGf InGSFEIGNf LLIiFVSYFG tKLHRPimIG vGCviMGLGc fLmsLPHFLM GrYEYEtt. isptsNlsSn
rOAT-K1     FgIptaiVGf InGSFEIGNL LLIiFVSYFG mKLHRPivIG vGCavMGLGc fiisLPHFLM GrYEYEtt. ilptsNlsSn
roatp1      FdIstSvaGL InGSFEIGNL ffIvFVSYFG tKLHRPvvIG iGCviMGLGc lLmsLPHFfM GrYEYEtt. isptgNlsSn
hOATP       FnIptSlVGf InGSFEIGNL LLIiFVSYFG tKLHRPimIG iGCvvMGLGc fLksLPHFLM nqYEYEst. vsvsgNlsSn
hOATP-RP5   FdIpsSlVGv IdGSFEIGNL LvItFVSYFG aKLHRPkiIG aGCviMGvGt lLiamPqFfM eqYkYEr.. yspssNstls
hOATP-RP2   FeIsSSlVGf IdGSFEIGNL LvIvFVSYFG sKLHRPklIG iGCfiMGiGg vLtaLPHFfM GyYrYsketn idsseNstSt
hOATP-RP3   FnlqSadVGv IassFEIGNL aLiLFVSYFG argHRPrlIG cGgivMaLGa lLsaLPeFLt hqYkYEag. .eirwgaegr
hPGT        FglsSSssGL IsslnEisNa iLiLFVSYFG srvHRPrlIG iGglflaaGa filtLPHFLs epYqYtla. .stgnNsrlq
hOATP-RP2   FglsSqtsGL lasfnEvGNt aLIvFVSYFG srvHRPrmIG yGailvaLag lLmtLPHFis epYrYdnts. .pedmpqdfk
hOATP-RP4   yslkSSesGL lvscFdIGNL vvvFVSYFG grgrRPlwla vGglliafGa aLfaLPHFis ppYqige... ..lnasapnd
hOATP-RP1   ydlhSyqsGL IasSydlaac LcltFVSYFG gsgHkPrwlG wGvlMGtGs lvfaLPHFta GrYEvEl.. .....dagvr
Consensus   F-I-SS-VGL I-GSFEIGNL LLI-FVSYFG -KLHRP--IG -GC--MGLG- -L--LPHFLM G-YEYE---- -----N--S-

241                                                                                   320
roatp2      sffCveNrSq ......tLnPt qD..psECvK Emk.SLMWIY VlVG...NIi RGIGETPImP LGISYIeDFA KsENSPLYIG
roatp3      sfLCmeNrSq ......tLkPt qD..paECiK Emk.SLMWIY VlVG...NIi RGIGETPImP LGISYIeDFA KsENSPLYIG
rOAT-K1     sfLCmeNqtq ......tLnPa qD..paECvK Evk.SLMWIY VlVG...NIi RGIGETPImP LGvSYIenFA KsENSPLYIG
roatp1      sfLCmeNrtq ......tLkPt qD..paECvK Emk.SLMWIc VmVG...NIi RGIGETPIvP LGISYIeDFA KsENSPLYIG
hOATP       sfLCmeNgtq ......iLrPt qD..psECtK Evk.SLMWvY VlVG...NIv RGmGETPIlP LGISYIeDFA KfENSPLYIG
hOATP-RP5   ispCllesSs qlpvsvmeks kskisneECev dts.SsMWIY VflG...NLL RGIGETPIqP LGIaYlDDFA sedNaafYIG
hOATP-RP2   lstClINqil s....lnras peivgkgClK Esg.SyMWIY VfmG...NmL RGIGETPIvP LGlSYIDDFA KeghSsLYlG
hOATP-RP3   .dvCaaNgSg g....degPd pD...liCrn rta.tnMmyl llIGa..qvL LGIGaTPvqP LGvSYIDDhv rrkdSsLYIG
hPGT        aeLCqkhwqd ......LpPs kchsttqmpq ket.SsMWgl mvVa...qlL aGIGtvPIqP fGISYIvDDFs epsNSPLYIs
hOATP-RP2   asLClpttSa p....asaPs ng..ncssyt Etq.hLsvvg imfva..qtL lGvGvPIqP iGmGsTPIyt hnsNSPLYIG
hOATP-RP4   .gLCqqgnSt a....tLeP. p.....aCpK dsggmnhwvY lalficaqIL iGmGsTPIyt LGpTYlDDnv KkENSsLYla
hOATP-RP1   ..tCpaN... ...P..... ....gavCad stsglsryql Vfmlg..qfL hGvGaTPlyt LGvtYlDenv KsscSPvYIa
Cons nsus   -LC---N-S- -------L-P- -D-----EC-K E---SLMWIY V-VG---NIL RGIGETPI-P LGISYIDDFA K-ENSPLYIG
```

FIG. 3B

```
                                                                                                    400
          321
roatp2    ILeTgmtiGP liGlLLaSsC AnIYVDiesV NTDdLtITPt DtRWVGAWWi GFLvCAGvni LtSfPFFFFP KtLP...KeG
roatp3    ILeTgkvfGP ivGlLLGSfC AsIYVDtGsV NTDdLtITPt DtRWVGAWWi GFLiCAGvmi LsSIPFFFFP KtLP...KeG
rOAT-K1   ILeTgkmiGP ifGlLLGSfC AsIYVDtGsV NTDdLtITPt DiRWVGAWWi GFLvCAGvni LiSIPFFFFP KtLP...KeG
roatp1    ILemgkvaGP ifGlLLGSyC AqIYVDiGsV NTDdLtITPs DtRWVGAWWi GFLvCAGvni LtSIPFFFFP KaLP...KkG
hOATP     lveTgaiiGP liGlLLaSfC AnvYVDtGfV NTDdLiITPt DtRWVGAWWf GFLiCAGvnv LtaIPFFFlP ntLP...KeG
hOATP-RP5 cvqTvaiiGP ifGfILGSlC AklYVDiGfV NlDhitiTPk DPqWVGAWW1 GYliagiisl LaavPFwylP KsLP...rsq
hOATP-RP2 ILnaiamiGP iiGfTLGSlf skmYVDiGyv dlstirITPt DsRWVGAWW1 nFLvsglfsi isSIPFFFlP qtpn...Kpq
hOATP-RP3 ILfTmlvfGP acGfiLGSfC tkIYVDavfi dTsnLdITPd DPRWiGAWWg GFLlCgallf fsSLlmFgFP qsLPphsdpa
hPGT      ILfaisvfGP afGyLLGSim lqIfVDyGrV NTaavnlvPg DPRWiGAWWi GLlissallv LtSfPFFFFP ramP....iG
hOATP-RP2 ILfavtmmGP glafgLGSlm lrlYVDinqm peggislTik DPRWVGAWW1 GFLiaAGava LaaIPyFFFP KemPkekrel
hOATP-RP4 ImyvmgalGP avGyLLGgll igfYVDp... .rnpvhldqn DPRFiGnWWs GFLlCAiamf LvifPmFtFP KKLPprhKkk
hOATP-RP1 IfyTaailGP aaGyLiGgal lnIYtemG.. ..rrtelTte sPlWVGAWWv GFLgsgaaaf ftavPilgyP rqLP...gs
Consensus IL-T----GP --G-LLGS-C A-IYVD-G-V NTD-L-ITP- DPRWVGAWW- GFL-CAG--- L-SIPFFFFP K-LP---K-G 480
          401
roatp2    lq..enVdgt e.........n akekkhrkka k.......... .eekrgit KDFfvfmKsL scNPiYmLfi LisV1QfNaf
roatp3    lq..ddVdgt n.........n dkeekhreka k.......... .eenrgit KDFlpfmKsL scNPiYmLli LtsV1QiNaf
roatp1    lq..enVdgt e.........n akeestekrp r.......... .kkmrgit KDFipfflKsp v1qPdlhavh pykvlQvNaf
roatp1    qq..enVavt k.........d gkvekyggqa r.......... .eenlgit KDFltfmKrL fcNPiYmLfi LtsV1QvNgf
hOATP     le..tnadii k.........n enedkqkeev k.......... .kekygit KDFlpfmKsL scNPiYmLfi LvsV1QfNaf
hOATP-RP5 sr..edsnss seksifii.d dhtdyqtpqg m.......... .akimema rDFlpslKnL fgNPvYfLyl ctstvQfNsl
hOATP-RP2 ke..rkasls lhvletn..d ekdqtanltn qg.......... .knitknv tgFfqsfKsi LtNPlYvmfv LitllQvssy
hOATP-RP3 mes.eqamls ereyerpkps ngvlrhplep dss......... .ascfql rvipkvtkhL LsNPvftcii Laacmeiavv
hPGT      ak...rapat a........d earkleeaks r.......... .gslvdfi KrFpcifIrL LmNslfvLvv Laqctfssvi
hOATP-RP2 qfr.rkVlav tdsparqkd spskqspges tkkqdglvqi apn1tviqfi KvFprvligt LsqVc1ssma LsqV1QfNaf
hOATP-RP4 kkkkfsVdav sddvdlkeks nnseqadkkv ss.......... .mgfgkdv rDlpraavri LsNmtflfvs Lsytaesaiv
hOATP-RP1 qr..yaVmra a..em....h qlkdssrgea sn......... .pdfgkti rDlplsiwLl LkNPtfilLc LagateatLi
Consensus -----V--- ---------- ---------- ---------- ----- KDF----K-L L-NP-Y-L-- L--V-Q-N--
```

FIG. 3C

```
            481                                                                         560
roatp2      insfTFmPKY LEQQYGkSta evvFLmGlym LPpiCiGyli GGlIMKKFKv tVkkAAhLAf wlCLseYLls flsyvmtCdN
roatp3      inmfTFLPKY LEQQYGkSta evvLliGvyn LPpiCiGyll iGfIMKKFKi tVkkAAymAf cLSLfeYLLy flhFmltCdN
rOAT-K1     niyfsFLPKY LEnYGkSta  eviFLmGvyn LPaiCiGyli aGfmMKKFKi tVktAAfLrf cLSLseYsfg fcnFlitCdN
roatp1      inkfTFLPKY LEQQYGkSta eAiFLiGvys LPpiCiGyli GGfIMKKFKi tVkkAAyLAf cLSVfeYLLf lchFmltCdN
hOATP       vnmisFmPKY LEQQYGisSS dAiFLmGlyn LPpiCiGyii GGlIMKKFKi tVkqAAhigc wlSLleYLLy flsFlmtCeN
hOATP-RP5   fGmvTykPKY iEQQYGqSsS rAnFviGlin iPavalGifs GGiVMKKFri sVcgAAkLyl gsSvfgYLLf lslFalgCeN
hOATP2      iGafTyvfKY vEQQYGqpsS kAnillGvit iPifasGmfl GGyIkKKFKl ntvgiAkfsc ftavmslsfy llyFfilCeN
hOATP-RP3   aGfaaFLgKY LEQQfnlttS sAnqLlGmta iPcaClGifl GGllvKKlsl salgAirmAm lvnLvstacy vsflflgCdt
hPGT        aGlsTFLnkf LEkQYGtsSa yAnFLiGavn LPaaalGmlf GGilMKrFvf slqtipriAt tiitismiLc vplFFmgCst
hOATP-RP2   aGmaTFLPKf LERQfsitaS yAnlLiGcls fPsvivGivv GGvlvKrlhl gpvgcgaLcl lgmLlclffs lplFfigCss
hOATP-RP4   tafiTFiPKf iEsQfGipaS nAsiytGvii vPsagvGivl GGyIikKKl1 icSgvsllcf stlFivgCes
hOATP-RP1   tGmsTFsPKf LEsQfslSaS eAatLfGylv vPagggGtfl GGffvnKlrl rgsavikfcl fctvvsLlg. ilvFslhCps
Cons nsus   -G---TFLPKY LEQQYG-S-S -A-FL-G---- LP---C-G--- GG-IMKKFK- -V--AA-LA- --SL--YLL- ---F----C-N 561                                                                         640
roatp2      fpVAGLTtsY  eGvqhqlyvE nkvlADCNtr  CnCststntwdP VCG.dNGlaY mSACLAGCe. .kSvGTGtN mVFq.NCSCI
roatp3      fpVAGLTaly  eGvhhplyvE nkvlADCNrg  CSCststnswdP VCG.dNGlaY mSACLAGCk. .kSvGTGtN mVFq.NCSCI
rOAT-K1     vpVAGLTnsY  erdqkplylE nnvlADCNtr  CSCltktwdP   VCG.dNGlaY mSACLAGCe. .kSvGTGtN mVFh.NCSCI
roatp1      aaVAGLTtsY  kGvghqlhvE skvlADCNtr  CSCststntwdP VCG.dNGvaY mSACLAGCk. .kfvGTGtN mVFq.dCSCI
hOATP       ssVvGintsY  eGipqdlyvE ndifADCNvd  CnCpskiwdP   VCG.nNGlsY lSACLAGCe. .tSiGTGiN mVFq.NCSCI
hOATP-RP5   sdVAGLTvsY  qGtkpvsyhE ralfsDCNsr  CkCsetkWeP   mCG.eNGitY vSACLAGCq. .tSnrsGxN iiFY.NCtCv
hOATP2      ksVAGLTmtY  dGnnpvtshr dvplsyCNsd  CnCdesqWeP   VCG.nNGitY iSpCLAGCk. .sSsGnkkp iVFY.NCSCl
hOATP-RP3   gpVAGVTvpY  .Gnstapgsa ldpyspCNnn  CeCqtdsftP   VCG.adGitY lSACfAGCn. ..stnlTG.. CaCl
hPGT        gpVAGVTvpY  ..tss.sihp qs..paCrrd  CSCpdsifhP   VCG.dNGieY lSpChAGCsn inmSsaTskq liyl.NCSCv
hOATP-RP2   ptVAevypps  ..sahpglE  ls..psCmea  CSCpldgfnP   VCdpstrveY itpChAGCss wvvqdaldns qVFytNCSCv
hOATP-RP4   hqiAGiThqt  ttgpsltmph rnltgsCNvm  CgCkiheyeP   VCG.sdGitY fnpCLAGCv. ..nSgnlstg irnyteCtCv
hOATP-RP1   inlgGinipY  Ggsllpegh  lnltApCNaa  CSCqpehysP   VCG.sdGlmY fSlChAGCpa atetnvdGqk .Vyr.dcsCI
vpmAGvTaSY
Consensus   --VAGLT-SY  -G------E  ----ADCN--  CSC----W-P   VCG---NG---Y -SACLAGC-- ---S-GTG-N -VF---NCSCI
```

FIG. 3D

```
            641                                                                          720
roatp2      qs..........  sGNSS.....  ..........  .AVLGlCnKg  PdCankLqYF  LiiaifgcFI  ySLagIPGYM  VlLRCiksEE
roatp3      rs..........  sGNSS.....  ..........  .AVLGlCkKg  PeCankLqYF  LimsvigSFI  ySitaIPGYM  VlLRCikpEk
rOAT-K1     qs..........  pGNSS.....  ..........  .AVLGlCnKg  PeCtnkLqYl  Lilsgflsil  ysFaaIPGYM  VfLRCVKsEE
roatp1      qs..........  lGNSS.....  ..........  .AVLGlCkKg  PeCanrLqYF  Liltiiisfi  ySLtaIPGYM  VfLRCVKsEE
hOATP       qt..........  sGNSS.....  ..........  .AVLGlCdKg  PdCslmLqYF  LilsamsSFI  ySLaaIPGYM  VlLRCmKsEE
hOATP-RP5   gia...ask     sGNSS.....  ..........  .givGrCqKd  ngCpqmflyF  LvisvitSyt  lSLggIPGYi  llLRCikpql
hOATP-RP2   evt...glq     nrNyS.....  ..........  .AhLGeCprd  daCtrkfyfF  vaiqvlnlFf  salggtshvM  livkivqpEl
hOATP-RP3   ttv...p..     aeNat.....  ..........  .vVpGkCp.s  PgCqeafltF  Lcvmcicsli  gamaqtPsvi  iliRtVspEl
hPGT        tg..........  .GsaS.....  ..........  .AktGsCp..  vpCahfLlpa  iflisfvsli  acishnPlYM  mvLRvVnqEE
hOATP-RP2   ve..........  .GNp......  ..........  .vlaGsCd..  stCshlvvpF  Lllvslgsal  acLthtPsfM  liLRgVKkEd
hOATP-RP4   qsrqvitppt    vGqrSqlrvv  ivktylneng   yAVsGkCkr.  .tCntlip.F  Lvflfivtfi  tacaqpsaii  VtLRsVedEE
hOATP-RP1   pqn....ls     sGfgh.....  ..........   .AtaGkCt..  stCqrkpl.l  Lvfifvvifff  tflssIPalt  atLRCVrdpq
Consensus   ----------    -GNSS----   ----------   -AVLG-C-K-  P-C----L-YF L------SFI  -SL--IPGYM  V-LRCVK-EE 721                                                                          800
roatp2      KSLgvGlHaf  ciRiLAGIPA  PIYFGALIDr  TCLHWGTlkC  GepGACRmYD  insFRrlYLG  LpaALRgaSf  vpaffILrLt
roatp3      KSLgiGlHaf  ctRvfAGIPA  PIYFGALIDr  TCLHWGTlkC  GepGACRmYn  innFRriYLv  LpaALRgsSy  LpalfILiLm
rOAT-K1     KSLgiGiHaf  ciRvfAGIPA  PIYFGALIDr  TCLHWGTqkC  GapGr.RmYD  insFRriYLG  msaALRgsSy  LpafvIviLt
roatp1      KSLgvGlHtf  ciRvfAGIPA  PvYFGALIDr  TCLHWGTlkC  GqrGACRmYD  insFRhiYLG  LpiALRgsSy  LpaffILiLm
hOATP       KSLgvGlHtf  ctRvfAGIPA  PIYFGALmDs  TCLHWGTlkC  GesGACRiYD  sttFRyiYLG  LpaALRgsSf  vpaliILiLl
hOATP-RP5   KSfAlGiytl   aiRvLAGIPA  PvYFGvLIDt  TCLkWGfkrC  GsrGsCRlYD  snvFRhiYLG  LtviLgtvSi  LisiavLfil
hOATP-RP2   KSLAlGfHsm   viRaLgGIlA  PIYFGALIDt  TCikWsTnnC  GtrGsCRtYn  stsFsrvYLG  LssmLRvsSl  vlyiiliyam
hOATP-RP3   KSyAlGvlfl   llRlLgfIPp  PliFGAgIDs  TCLfwsT.fC  GeqGACvlYD  nvvyRylYvs   iaiALksfaf  ilytttwqcl
hPGT        KSfAiGvqfl   lmRlLAwlPs  PalyGltIDh  sCirWnslcl  GrrGACayYD  ndalRdrYLG  Lqmgykalgm  Lllcflswrv
hOATP-RP2   KtLAvGiqfm   flRilAwmPs  PvihGsaIDt  TCvHWal.sC  GrravCRyYn  ndllRnrfiG  Lqfffktgsv  icfalvLavl
hOATP-RP4   rpfAlGmqfv   llRtLAyIPt  PIYfGAvIDt  TCmlWqq.eC  GvqGsCweYn  vtsFRfvYfG  LaagLkfvgf  ififlawysi
hOATP-RP1   rsfAlGiqwi   vvRilgGIPg  PlaFGwvIDk  aCllWqd.qC  GqqGsClvYq  nsamsryiLi  mgllykvlgv  Lffaiacfly
Consensus   KSLA-G-H--   --R-LAGIPA  PIYFGALID-  TCLHWGT--C  G--GACR-YD  ---FR--YLG  L--ALR--S-  L----IL-L-
```

FIG. 3E

```
              801                                                           880
   roatp2     R.......tfq fPgd...Ies Sk....tdha emkltlKESe cTevlrs.kv t..eD........... ..........
   roatp3     R.......Kfq fPge...IdS SE....tela emkitvKkse cTdvHgspqv e..nDgElkT rl..... ..........
   rOAT-K1    R.......Kfs lPgk...InS SE....meia emklteKESq cTdvHrnpkf k..nDgElkT kl..... ..........
   roatp1     R.......Kfq fPgd...IdS Sa....tdht emmlgeKESe hTdvHgspqv e..nDgElkT kl..... ..........
   hOATP      R.......Kch lPge...naS Sg....teli etkvkgKEne ckdiyqkstv l..kDdElkT kl..... ..........
   hOATP-RP5  k.......Kny vskhrsfItk rE....rtmv strfq.KEny tTsdHllqpn y..wpgke.T ql..... ..........
   hOATP2     k.......Kky qekd..Ina SE....ngsv mdean.lESl nknkHfvpsa g..aDsEthc ....... ..........
   hOATP-RP3  Rkny....Kry iknhegglst SEff.astlt ldnlgrdpvp anqtHrtkfi ynleDhEwce nmesvl. ..........
   hPGT       k.......Knk .eyn...vqk aa.....gli ........ ........ ........ ....... ..........
   hOATP-RP2  Rqqd....Kea rtke..srS Sp....ave qqllvsgppgk kpedsrv.. ........ ....... ..........
   hOATP-RP4  kykedglqrr rqrefplstv SErvghpdna rtrscpafst qgefHeetgl qkgiqcaaqT ypgpfpeais ssadpglees
   hOATP-RP1  k.......Pls....eS Sd...gletc lpsqssapds aTdsqlqssv ........ ....... ..........
   Consensus  R-------K-- -P-------- SE-------- ------KES- -T---H---- ----D-E--T ------- ----------

881
   roatp2     ..........
   roatp3     ..........
   rOAT-K1    ..........
   roatp1     ..........
   hOATP      ..........
   hOATP-RP5  ..........
   hOATP2     ..........
   hOATP-RP3  ..........
   hPGT       ..........
   hOATP-RP2  ..........
   hOATP-RP4  paalepxs..
   hOATP-RP1  ..........
   Consensus  ----------
```

FIG. 3F

SEQUENCE LISTING

<160> NUMBER OF SEQ ID NOS: 22

<210> SEQ ID NO 1
<211> LENGTH: 2830
<212> TYPE: DNA
<213> ORGANISM: Homo sapiens

<400> SEQUENCE: 1

```
cggacgcgtg ggcggacgcg tgggtcgccc acgcgtccga cttgttgcag ttgctgtagg      60
attctaaatc caggtgattg tttcaaactg agcatcaaca acaaaaacat ttgtatgata     120
tctatatttc aatcatggac caaaatcaac atttgaataa aacagcagag gcacaacctt     180
cagagaataa gaaaacaaga tactgcaatg gattgaagat gttcttggca gctctgtcac     240
tcagctttat tgctaagaca ctaggtgcaa ttattatgaa aagttccatc attcatatag     300
aacggagatt tgagatatcc tcttctcttg ttggttttat tgacggaagc tttgaaattg     360
gaaatttgct tgtgattgta tttgtgagtt actttggatc caaactacat agaccaaagt     420
taattggaat cggttgtttc attatgggaa ttggaggtgt tttgactgct ttgccacatt     480
tcttcatggg atattacagg tattctaaag aaactaatat cgattcatca gaaaattcaa     540
catcgacctt atccacttgt ttaattaatc aaatttatc actcaataga gcatcacctg     600
agatagtggg aaaaggttgt ttaaaggaat ctgggtcata catgtggata tatgtgttca     660
tgggtaatat gcttcgtgga ataggggaga ctcccatagt accattgggg ctttcttaca     720
ttgatgattt cgctaaagaa ggacattctt ctttgtattt aggtatattg aatgcaatag     780
caatgattgg tccaatcatt ggctttaccc tgggatctct gttttctaaa atgtacgtgg     840
atattggata tgtagatcta agcactatca ggataactcc tactgattct cgatgggttg     900
gagcttggtg gcttaatttc cttgtgtctg gactattctc cattatttct tccataccat     960 tcttttttctt gccccaaact ccaataaac cacaaaaaga aagaaaagct tcactgtctt    1020
tgcatgtgct ggaaacaaat gatgaaaagg atcaaacagc taatttgacc aatcaaggaa    1080
aaaatattac caaaaatgtg actggttttt tccagtcttt taaaagcatc cttactaatc    1140
ccctgtatgt tatgttttgtg cttttgacgt tgttacaagt aagcagctat attggtgctt    1200
ttacttatgt cttcaaatac gtagagcaac agtatggtca gccttcatct aaggctaaca    1260
tcttattggg agtcataacc ataccctattt ttgcaagtgg aatgttttta ggaggatata    1320
tcattaaaaa attcaaactg aacaccgttg gaattgccaa attctcatgt tttactgctg    1380
tgatgtcatt gtcctttac ctattatatt ttttcatact ctgtgaaaac aaatcagttg    1440
ccggactaac catgacctat gatggaaata tccagtgac atctcataga gatgtaccac    1500
tttcttattg caactcagac tgcaattgtg atgaaagtca atgggaacca gtctgtggaa    1560
```

```
acaatggaat aacttacatc tcaccctgtc tagcaggttg caaatcttca agtggcaata    1620
aaaagcctat agtgttttac aactgcagtt gtttggaagt aactggtctc cagaacagaa    1680
attactcagc ccatttgggt gaatgcccaa gagatgatgc ttgtacaagg aaattttact    1740
tttttgttgc aatacaagtc ttgaatttat ttttctctgc acttggaggc acctcacatg    1800
tcatgctgat tgttaaaatt gttcaacctg aattgaaatc acttgcactg ggtttccact    1860
caatggttat acgagcacta ggaggaattc tagctccaat atattttggg gctctgattg    1920
atacaacgtg tataaagtgg tccaccaaca actgtggcac acgtgggtca tgtaggacat    1980
ataattccac atcattttca agggtctact tgggcttgtc ttcaatgtta agagtctcat    2040 cacttgttt atatattata ttaatttatg ccatgaagaa aaaatatcaa gagaaagata    2100
tcaatgcatc agaaatgga agtgtcatgg atgaagcaaa cttagaatcc ttaaataaaa    2160
ataaacattt tgtcccttct gctggggcag atagtgaaac acattgttaa ggggagaaaa    2220
aaagccactt ctgcttctgt gtttccaaac agcattgcat tgattcagta agatgttatt    2280
tttgaggagt tcctggtcct ttcactaaga atttccacat cttttatggt ggaagtataa    2340
ataagcctat gaacttataa taaaacaaac tgtaggtaga aaaaatgaga gtactcattg    2400
ttacattata gctacatatt tgtggttaag gttagactat atgatccata caaattaaag    2460
tgagagacat ggttactgtg taataaaaga aaaaatactt gttcaggtaa ttctaattct    2520
taataaaaca aatgagtatc atacaggtag aggttaaaaa ggaggagcta gattcatatc    2580
ctaagtaaag agaaatgcct agtgtctatt ttattaaaca aacaaacaca gagtttgaac    2640
tataatacta aggcctgaag tctagcttgg atatatgcta caataatatc tgttactcac    2700
ataaaattat atatttcaca gactttatca atgtataatt aacaattatc ttgtttaagt    2760
aaatttagaa tacatttaag tattgtggaa gaaataaaga cattccaata tttgcaaaaa    2820
aaaaaaaaaa                                                           2830
```

<210> SEQ ID NO 2
<211> LENGTH: 691
<212> TYPE: PRT
<213> ORGANISM: Homo sapiens

<400> SEQUENCE: 2

```
Met Asp Gln Asn Gln His Leu Asn Lys Thr Ala Glu Ala Gln Pro Ser
 1               5                  10                  15

Glu Asn Lys Lys Thr Arg Tyr Cys Asn Gly Leu Lys Met Phe Leu Ala
                20                  25                  30

Ala Leu Ser Leu Ser Phe Ile Ala Lys Thr Leu Gly Ala Ile Ile Met
            35                  40                  45

Lys Ser Ser Ile Ile His Ile Glu Arg Arg Phe Glu Ile Ser Ser Ser
        50                  55                  60

Leu Val Gly Phe Ile Asp Gly Ser Phe Glu Ile Gly Asn Leu Leu Val
 65                  70                  75                  80

Ile Val Phe Val Ser Tyr Phe Gly Ser Lys Leu His Arg Pro Lys Leu
                85                  90                  95

Ile Gly Ile Gly Cys Phe Ile Met Gly Ile Gly Gly Val Leu Thr Ala
            100                 105                 110

Leu Pro His Phe Phe Met Gly Tyr Tyr Arg Tyr Ser Lys Glu Thr Asn
        115                 120                 125

Ile Asp Ser Ser Glu Asn Ser Thr Ser Thr Leu Ser Thr Cys Leu Ile
    130                 135                 140
```

-continued

```
Asn Gln Ile Leu Ser Leu Asn Arg Ala Ser Pro Glu Ile Val Gly Lys
145                 150                 155                 160

Gly Cys Leu Lys Glu Ser Gly Ser Tyr Met Trp Ile Tyr Val Phe Met
            165                 170                 175

Gly Asn Met Leu Arg Gly Ile Gly Glu Thr Pro Ile Val Pro Leu Gly
            180                 185                 190

Leu Ser Tyr Ile Asp Asp Phe Ala Lys Glu Gly His Ser Ser Leu Tyr
            195                 200                 205

Leu Gly Ile Leu Asn Ala Ile Ala Met Ile Gly Pro Ile Ile Gly Phe
210                 215                 220

Thr Leu Gly Ser Leu Phe Ser Lys Met Tyr Val Asp Ile Gly Tyr Val
225                 230                 235                 240

Asp Leu Ser Thr Ile Arg Ile Thr Pro Thr Asp Ser Arg Trp Val Gly
            245                 250                 255

Ala Trp Trp Leu Asn Phe Leu Val Ser Gly Leu Phe Ser Ile Ile Ser
            260                 265                 270

Ser Ile Pro Phe Phe Phe Leu Pro Gln Thr Pro Asn Lys Pro Gln Lys
275                 280                 285

Glu Arg Lys Ala Ser Leu Ser Leu His Val Leu Glu Thr Asn Asp Glu
290                 295                 300

Lys Asp Gln Thr Ala Asn Leu Thr Asn Gln Gly Lys Asn Ile Thr Lys
305                 310                 315                 320

Asn Val Thr Gly Phe Phe Gln Ser Phe Lys Ser Ile Leu Thr Asn Pro
            325                 330                 335

Leu Tyr Val Met Phe Val Leu Leu Thr Leu Leu Gln Val Ser Ser Tyr
            340                 345                 350

Ile Gly Ala Phe Thr Tyr Val Phe Lys Tyr Val Glu Gln Gln Tyr Gly
            355                 360                 365

Gln Pro Ser Ser Lys Ala Asn Ile Leu Leu Gly Val Ile Thr Ile Pro
370                 375                 380

Ile Phe Ala Ser Gly Met Phe Leu Gly Gly Tyr Ile Ile Lys Lys Phe
385                 390                 395                 400

Lys Leu Asn Thr Val Gly Ile Ala Lys Phe Ser Cys Phe Thr Ala Val
            405                 410                 415

Met Ser Leu Ser Phe Tyr Leu Leu Tyr Phe Phe Ile Leu Cys Glu Asn
            420                 425                 430

Lys Ser Val Ala Gly Leu Thr Met Thr Tyr Asp Gly Asn Asn Pro Val
            435                 440                 445

Thr Ser His Arg Asp Val Pro Leu Ser Tyr Cys Asn Ser Asp Cys Asn
450                 455                 460

Cys Asp Glu Ser Gln Trp Glu Pro Val Cys Gly Asn Asn Gly Ile Thr
465                 470                 475                 480

Tyr Ile Ser Pro Cys Leu Ala Gly Cys Lys Ser Ser Ser Gly Asn Lys
            485                 490                 495

Lys Pro Ile Val Phe Tyr Asn Cys Ser Cys Leu Glu Val Thr Gly Leu
            500                 505                 510

Gln Asn Arg Asn Tyr Ser Ala His Leu Gly Glu Cys Pro Arg Asp Asp
            515                 520                 525

Ala Cys Thr Arg Lys Phe Tyr Phe Phe Val Ala Ile Gln Val Leu Asn
530                 535                 540

Leu Phe Phe Ser Ala Leu Gly Gly Thr Ser His Val Met Leu Ile Val
545                 550                 555                 560
```

```
Lys Ile Val Gln Pro Glu Leu Lys Ser Leu Ala Leu Gly Phe His Ser
                565                 570                 575
Met Val Ile Arg Ala Leu Gly Gly Ile Leu Ala Pro Ile Tyr Phe Gly
            580                 585                 590
Ala Leu Ile Asp Thr Thr Cys Ile Lys Trp Ser Thr Asn Asn Cys Gly
        595                 600                 605
Thr Arg Gly Ser Cys Arg Thr Tyr Asn Ser Thr Ser Phe Ser Arg Val
    610                 615                 620
Tyr Leu Gly Leu Ser Ser Met Leu Arg Val Ser Ser Leu Val Leu Tyr
625                 630                 635                 640
Ile Ile Leu Ile Tyr Ala Met Lys Lys Tyr Gln Glu Lys Asp Ile
                645                 650                 655
Asn Ala Ser Glu Asn Gly Ser Val Met Asp Glu Ala Asn Leu Glu Ser
                660                 665                 670
Leu Asn Lys Asn Lys His Phe Val Pro Ser Ala Gly Ala Asp Ser Glu
            675                 680                 685
Thr His Cys
    690

<210> SEQ ID NO 3
<211> LENGTH: 2442
<212> TYPE: DNA
<213> ORGANISM: Homo sapiens

<400> SEQUENCE: 3
cccgggtcga cccacgcgtc cgggataaag tactcccagg aaggctttga gccttggcag       60
aagaggctgg gattgaagct tcagggagag ccagaggtga ggctggagtg ggagatcacc      120
tgaggcaggg ccagcgggtg aggtacccca ggtaccagac aaggaaacca aagccacaat      180
gggcacagaa aacacacctg gaggcaaagc cagcccagac cctcaggacg tgcggccaag      240
tgtgttccat aacatcaagc tgttcgttct gtgccacagc tgctgcagc tggcgcagct      300 catgatctcc ggctacctaa agagctccat ctccacagtg gagaagcgct tcggcctctc      360
cagccagacg tcgggctgc tggcctcctt caacgaggtg gggaacacag ccttgattgt      420
gtttgtgagc tattttggca gccgggtgca ccgaccccga atgattggct atgggctat      480 ccttgtggcc ctggcgggcc tgctcatgac tctcccgcac ttcatctcgg agccataccg      540
ctacgacaac accagccctg aggatatgcc acaggacttc aaggcttccc tgtgcctgcc      600
cacaacctcg gccccagcct cggccccctc caatggcaac tgctcaagct acacagaaac      660
ccagcatctg agtgtggtgg ggatcatgtt cgtggcacag accctgctgg gcgtgggcgg      720
ggtgcccatt cagcccttg gcatctccta catcgttgac tttgcccaca acagtaactc      780
gcccctctac ctcgggatcc tgtttgcagt gaccatgatg gggccaggcc tggcctttgg      840
gctgggcagc tcatgctgc gcctttatgt ggacattaac cagatgccag aagtggtat      900 cagcctgacc ataaaggacc ccgatgggt gggtgcctgg tggctgggtt cctcatcgc      960 tgccggtgca gtggccctgg ctgccatccc ctacttcttc ttccccaagg aaatgcccaa     1020
ggaaaaacgt gagcttcagt ttcggcgaaa ggtcttagca gtcacagact cacctgccag     1080
gaagggcaag gactctccct ctaagcagag ccctggggag tccacgaaga gcaggatgg     1140 cctagtccag attgcaccaa acctgactgt gatccagttc attaaagtct tccccagggt     1200
gctgctgcag accctacgcc acccccatctt cctgctggtg gtcctgtccc aggtatgctt     1260
gtcatccatg gctgcgggca tggccaccctt cctgcccaag ttcctggagc gccagttttc     1320
```

-continued

```
catcacagcc tcctacgcca acctgctcat cggctgcctc tccttcccett cggtcatcgt    1380 gggcatcgtg gtgggtggcg tcctggtcaa gcggctccac ctgggccctg tgggatgcgg    1440
tgccctttgc ctgctgggga tgctgctgtg cctcttcttc agcctgccgc tcttctttat    1500
cggctgctcc agccaccaga ttgcgggcat acacaccag accagtgccc accctgggct    1560
ggagctgtct ccaagctgca tggaggcctg ctcctgccca ttggacggct ttaaccctgt    1620
ctgcgacccc agcactcgtg tggaatacat cacaccctgc cacgcaggct gctcaagctg    1680
ggtggtccag gatgctctgg acaacagcca ggttttctac accaactgca gctgcgtggt    1740
ggagggcaac cccgtgctgg caggatcctg cgactcaacg tgcagccatc tggtggtgcc    1800
cttcctgctc ctggtcagcc tgggctcggc cctggcctgt ctcacccaca caccctcctt    1860
catgctcatc ctaagaggag tgaagaaaga agacaagact ttggctgtgg gcatccagtt    1920
catgttcctg aggattttgg cctggatgcc cagccccgtg atccacggca gcgccatcga    1980
caccacctgt gtgcactggg ccctgagctg tgggcgtcga gctgtctgtc gctactacaa    2040
taatgacctg ctccgaaacc ggttcatcgg cctccagttc ttcttcaaaa caggttctgt    2100
gatctgcttc gccttagttt tggctgtcct gaggcagcag acaaagagg caaggaccaa    2160 agagagcaga tccagccctg ccgtagagca gcaattgcta gtgtcggggc agggaagaa    2220 gccagaggat tcccgagtgt gagctgtctt ggggcccccac ctggccaaga gtagcagcca    2280
cagcagtacc tcctctgagt cctttgccca agattgggtg tcaagagccc tgtgttccat    2340
tctggctcct ccactaaatt gctgtgtgac ttcaggcaaa aaaaaaaaaa aaaaaaaaa    2400 aaaaaaaaaa aaaaaaaaaa aaaaaaaaaa aaaaaaaaa aa                        2442
```

<210> SEQ ID NO 4
<211> LENGTH: 687
<212> TYPE: PRT
<213> ORGANISM: Homo sapiens

<400> SEQUENCE: 4

```
Met Gly Thr Glu Asn Thr Pro Gly Gly Lys Ala Ser Pro Asp Pro Gln
 1               5                  10                  15

Asp Val Arg Pro Ser Val Phe His Asn Ile Lys Leu Phe Val Leu Cys
            20                  25                  30

His Ser Leu Leu Gln Leu Ala Gln Leu Met Ile Ser Gly Tyr Leu Lys
        35                  40                  45

Ser Ser Ile Ser Thr Val Glu Lys Arg Phe Gly Leu Ser Ser Gln Thr
    50                  55                  60

Ser Gly Leu Leu Ala Ser Phe Asn Glu Val Gly Asn Thr Ala Leu Ile
65                  70                  75                  80

Val Phe Val Ser Tyr Phe Gly Ser Arg Val His Arg Pro Arg Met Ile
                85                  90                  95

Gly Tyr Gly Ala Ile Leu Val Ala Leu Ala Gly Leu Leu Met Thr Leu
            100                 105                 110

Pro His Phe Ile Ser Glu Pro Tyr Arg Tyr Asp Asn Thr Ser Pro Glu
        115                 120                 125

Asp Met Pro Gln Asp Phe Lys Ala Ser Leu Cys Leu Pro Thr Thr Ser
    130                 135                 140

Ala Pro Ala Ser Ala Pro Ser Asn Gly Asn Cys Ser Ser Tyr Thr Glu
145                 150                 155                 160

Thr Gln His Leu Ser Val Val Gly Ile Met Phe Val Ala Gln Thr Leu
                165                 170                 175
```

```
Leu Gly Val Gly Gly Val Pro Ile Gln Pro Phe Gly Ile Ser Tyr Ile
            180                 185                 190
Val Asp Phe Ala His Asn Ser Asn Ser Pro Leu Tyr Leu Gly Ile Leu
            195                 200                 205
Phe Ala Val Thr Met Met Gly Pro Gly Leu Ala Phe Gly Leu Gly Ser
            210                 215                 220
Leu Met Leu Arg Leu Tyr Val Asp Ile Asn Gln Met Pro Glu Gly Gly
225                 230                 235                 240
Ile Ser Leu Thr Ile Lys Asp Pro Arg Trp Val Gly Ala Trp Trp Leu
                245                 250                 255
Gly Phe Leu Ile Ala Ala Gly Ala Val Ala Leu Ala Ala Ile Pro Tyr
            260                 265                 270
Phe Phe Phe Pro Lys Glu Met Pro Lys Glu Lys Arg Glu Leu Gln Phe
            275                 280                 285
Arg Arg Lys Val Leu Ala Val Thr Asp Ser Pro Ala Arg Lys Gly Lys
290                 295                 300
Asp Ser Pro Ser Lys Gln Ser Pro Gly Glu Ser Thr Lys Lys Gln Asp
305                 310                 315                 320
Gly Leu Val Gln Ile Ala Pro Asn Leu Thr Val Ile Gln Phe Ile Lys
                325                 330                 335
Val Phe Pro Arg Val Leu Leu Gln Thr Leu Arg His Pro Ile Phe Leu
            340                 345                 350
Leu Val Val Leu Ser Gln Val Cys Leu Ser Ser Met Ala Ala Gly Met
            355                 360                 365
Ala Thr Phe Leu Pro Lys Phe Leu Glu Arg Gln Phe Ser Ile Thr Ala
            370                 375                 380
Ser Tyr Ala Asn Leu Leu Ile Gly Cys Leu Ser Phe Pro Ser Val Ile
385                 390                 395                 400
Val Gly Ile Val Val Gly Gly Val Leu Val Lys Arg Leu His Leu Gly
            405                 410                 415
Pro Val Gly Cys Gly Ala Leu Cys Leu Leu Gly Met Leu Leu Cys Leu
            420                 425                 430
Phe Phe Ser Leu Pro Leu Phe Phe Ile Gly Cys Ser Ser His Gln Ile
            435                 440                 445
Ala Gly Ile Thr His Gln Thr Ser Ala His Pro Gly Leu Glu Leu Ser
            450                 455                 460
Pro Ser Cys Met Glu Ala Cys Ser Cys Pro Leu Asp Gly Phe Asn Pro
465                 470                 475                 480
Val Cys Asp Pro Ser Thr Arg Val Glu Tyr Ile Thr Pro Cys His Ala
                485                 490                 495
Gly Cys Ser Ser Trp Val Val Gln Asp Ala Leu Asp Asn Ser Gln Val
            500                 505                 510
Phe Tyr Thr Asn Cys Ser Cys Val Val Glu Gly Asn Pro Val Leu Ala
            515                 520                 525
Gly Ser Cys Asp Ser Thr Cys Ser His Leu Val Val Pro Phe Leu Leu
            530                 535                 540
Leu Val Ser Leu Gly Ser Ala Leu Ala Cys Leu Thr His Thr Pro Ser
545                 550                 555                 560
Phe Met Leu Ile Leu Arg Gly Val Lys Lys Glu Asp Lys Thr Leu Ala
                565                 570                 575
Val Gly Ile Gln Phe Met Phe Leu Arg Ile Leu Ala Trp Met Pro Ser
            580                 585                 590
Pro Val Ile His Gly Ser Ala Ile Asp Thr Thr Cys Val His Trp Ala
```

```
                595                 600                 605
Leu Ser Cys Gly Arg Arg Ala Val Cys Arg Tyr Tyr Asn Asn Asp Leu
    610                 615                 620

Leu Arg Asn Arg Phe Ile Gly Leu Gln Phe Phe Lys Thr Gly Ser
625                 630                 635                 640

Val Ile Cys Phe Ala Leu Val Leu Ala Val Leu Arg Gln Gln Asp Lys
                645                 650                 655

Glu Ala Arg Thr Lys Glu Ser Arg Ser Ser Pro Ala Val Glu Gln Gln
            660                 665                 670

Leu Leu Val Ser Gly Pro Gly Lys Lys Pro Glu Asp Ser Arg Val
                675                 680                 685

<210> SEQ ID NO 5
<211> LENGTH: 2757
<212> TYPE: DNA
<213> ORGANISM: Homo sapiens

<400> SEQUENCE: 5
cccacgcgtc cggcgaggag ctgtgccttc cacctctcca gccccggcag gacgggggcg      60
gccgccgcga acccggggcg gggacagcac gcagcctcga ggcgcgcacc cccgcccggc     120
agcggccccg acaccggggg cgagcgggaa agcggcagcg gcggcggcgg cggcggcggc     180
gggggaagga tgcaggggaa gaagccgggc ggttcgtcgg gcggcggccg gagcggcgag     240
ctgcaggggg acgaggcgca gaggaacaag aaaaagaaaa agaaggtgtc ctgcttttcc     300
aacatcaaga tcttcctggt gtccgagtgc gccctgatgc tggcgcaggg cacggtgggc     360
gcctacctgg tgagcgtcct gaccaccctg agcgtaggt tcaacctgca gagcgctgac     420
gtgggtgtga tcgctagcag cttcgagatc gggaacctgg cgctcatcct cttcgtgagc     480
tacttcgggg cacgcgggca ccggccgcgc ctgatcggct gcggcggcat cgtcatggcg     540
ctgggcgcgc tgctgtcggc gctgcccgag ttcctgaccc accagtacaa gtacgaggcg     600
ggcgagatcc gctggggcgc cgagggccgc gacgtctgcg cagccaacgg ctcgggcggc     660
gacgaggggc ccgaccccga cctcatctgc gcaaccgga cggctaccaa catgatgtac     720
ttgctgctca ttgggcccca ggtgctcctg ggcatcggtg ctaccctgt gcagcccctg     780
ggcgtctcct acatcgacga ccacgtgcgg aggaaggact cctcgctcta tagaggaatc     840
ctgttcacga tgctggtatt tggaccagcc tgcgggttta tcctgggctc tttctgtacc     900
aaaatctacg tggatgcggt cttcattgac acaagtaacc tggacatcac tccggacgac     960
ccccgctgga tcggagcctg gtggggtggc tttctgctct gcggtgcctt actcttcttc    1020
tcttccctct tgatgtttgg gtttccacag tccctgcccc cgcactcaga ccccgccatg    1080
gaaagcgagc aggccatgct ctccgaaaga gaatacgaga acccaagcc cagcaacggg    1140
gtcctgaggc acccctgga gccagacagc agtgcctcct gtttccagca gctgagagtg    1200
atcccgaagg tcaccaagca cctgctctca aaccctgtgt tcacctgcat catcctggcc    1260
gcctgcatgg agattgcagt ggtggctggc ttcgctgcct ttttggggaa gtacctggag    1320
cagcagttta acctcaccac ctcttctgcc aaccagctgc ttgggatgac tgcgatcccg    1380
tgtgcttgtc tgggtatctt cctgggaggt cttttggtga agaagctcag cctgtctgcc    1440
ctgggggcca ttcggatggc catgctcgtc aacctggtgt ccactgcttg ctacgtctcc    1500
ttcctcttcc tgggctgcga cactggccct gtgctggggg ttactgttcc ctatggaaac    1560
agcacagcac ctggctcagc cctggacccc tactcgccct gcaataataa ctgtgaatgc    1620
```

-continued

```
caaaccgatt ccttcactcc agtgtgtggg gcagatggca tcacctacct gtctgcctgc    1680
tttgctggct gcaacagcac gaatctcacg ggctgtgcgt gcctcaccac cgtccctgct    1740
gagaacgcaa ccgtggttcc tggaaaatgc cccagtcctg ggtgccaaga ggccttcctc    1800
actttcctct gtgtgatgtg tatctgcagc ctgatcggtg ccatggcaca gacaccctca    1860
gtcatcatcc tcatcaggac agtcagcccct gaactcaagt cttacgcttt gggagttctt    1920
tttctcctcc ttcgtttgtt gggcttcatc cctccacccc tcatcttcgg ggctggcatc    1980
gactccacct gcctgttctg gagcacgttc tgtggggagc aaggcgcctg cgtcctctac    2040
gacaatgtgg tctaccgata cctgtatgtc agcatccgcca tcgcgctcaa atccttcgcc    2100
ttcatcctgt acaccaccac gtggcagtgc tgaggaaaaa actataaacg ctacatcaaa    2160
aaccacgagg gcgggctgag caccagtgag ttctttgcct ctactctgac cctagacaac    2220
ctggggaggg accctgtgcc cgcaaaccag acacatagga caaagtttat ctataacctg    2280
gaagaccatg agtggtgtga aaacatggag tccgttttat agtgactaaa ggagggctga    2340
actctgtatt agtaatccaa gggtcatttt tttcttaaaa aagaaaaaa aggttccaaa    2400
aaaaaccaaa actcagtaca cacacacagg cacagatgca cacacacgca gacagacaca    2460
ccgactttgt cctttttctc agcatcagag ccagacagga ttcagaataa ggagagaatg    2520
acatcgtgcg gcagggtcct ggaggccact cgcgcggctg ggccacagag tctactttga    2580
aggcacctca tggttttcag gatgctgaca gctgcaagca acaggcactg ccaaattcag    2640
ggaacagtgg tggccagctt ggaggatgga catttctgga tacacataca catacaaaac    2700
agaaaacatt ttttaaaaga agtttcctaa aataaaaaaa ataaaaaaaa aaaaaaa     2757
```

<210> SEQ ID NO 6
<211> LENGTH: 710
<212> TYPE: PRT
<213> ORGANISM: Homo sapiens

<400> SEQUENCE: 6

```
Met Gln Gly Lys Lys Pro Gly Ser Ser Gly Gly Arg Ser Gly
  1               5                  10                  15

Glu Leu Gln Gly Asp Glu Ala Gln Arg Asn Lys Lys Lys Lys Lys
                 20                  25                  30

Val Ser Cys Phe Ser Asn Ile Lys Ile Phe Leu Val Ser Glu Cys Ala
             35                  40                  45

Leu Met Leu Ala Gln Gly Thr Val Gly Ala Tyr Leu Val Ser Val Leu
         50                  55                  60

Thr Thr Leu Glu Arg Arg Phe Asn Leu Gln Ser Ala Asp Val Gly Val
     65                  70                  75                  80

Ile Ala Ser Ser Phe Glu Ile Gly Asn Leu Ala Leu Ile Leu Phe Val
                 85                  90                  95

Ser Tyr Phe Gly Ala Arg Gly His Arg Pro Arg Leu Ile Gly Cys Gly
                100                 105                 110

Gly Ile Val Met Ala Leu Gly Ala Leu Leu Ser Ala Leu Pro Glu Phe
            115                 120                 125

Leu Thr His Gln Tyr Lys Tyr Glu Ala Gly Glu Ile Arg Trp Gly Ala
        130                 135                 140

Glu Gly Arg Asp Val Cys Ala Ala Asn Gly Ser Gly Gly Asp Glu Gly
    145                 150                 155                 160

Pro Asp Pro Asp Leu Ile Cys Arg Asn Arg Thr Ala Thr Asn Met Met
                165                 170                 175
```

-continued

```
Tyr Leu Leu Leu Ile Gly Ala Gln Val Leu Gly Ile Gly Ala Thr
            180                 185                 190

Pro Val Gln Pro Leu Gly Val Ser Tyr Ile Asp Asp His Val Arg Arg
        195                 200                 205

Lys Asp Ser Ser Leu Tyr Ile Gly Ile Leu Phe Thr Met Leu Val Phe
        210                 215                 220

Gly Pro Ala Cys Gly Phe Ile Leu Gly Ser Phe Cys Thr Lys Ile Tyr
225                 230                 235                 240

Val Asp Ala Val Phe Ile Asp Thr Ser Asn Leu Asp Ile Thr Pro Asp
                245                 250                 255

Asp Pro Arg Trp Ile Gly Ala Trp Trp Gly Gly Phe Leu Leu Cys Gly
            260                 265                 270

Ala Leu Leu Phe Phe Ser Ser Leu Leu Met Phe Gly Phe Pro Gln Ser
        275                 280                 285

Leu Pro Pro His Ser Asp Pro Ala Met Glu Ser Glu Gln Ala Met Leu
        290                 295                 300

Ser Glu Arg Glu Tyr Glu Arg Pro Lys Pro Ser Asn Gly Val Leu Arg
305                 310                 315                 320

His Pro Leu Glu Pro Asp Ser Ser Ala Ser Cys Phe Gln Gln Leu Arg
                325                 330                 335

Val Ile Pro Lys Val Thr Lys His Leu Leu Ser Asn Pro Val Phe Thr
            340                 345                 350

Cys Ile Ile Leu Ala Ala Cys Met Glu Ile Ala Val Val Ala Gly Phe
        355                 360                 365

Ala Ala Phe Leu Gly Lys Tyr Leu Glu Gln Gln Phe Asn Leu Thr Thr
        370                 375                 380

Ser Ser Ala Asn Gln Leu Leu Gly Met Thr Ala Ile Pro Cys Ala Cys
385                 390                 395                 400

Leu Gly Ile Phe Leu Gly Gly Leu Leu Val Lys Lys Leu Ser Leu Ser
                405                 410                 415

Ala Leu Gly Ala Ile Arg Met Ala Met Leu Val Asn Leu Val Ser Thr
            420                 425                 430

Ala Cys Tyr Val Ser Phe Leu Phe Leu Gly Cys Asp Thr Gly Pro Val
        435                 440                 445

Ala Gly Val Thr Val Pro Tyr Gly Asn Ser Thr Ala Pro Gly Ser Ala
        450                 455                 460

Leu Asp Pro Tyr Ser Pro Cys Asn Asn Asn Cys Glu Cys Gln Thr Asp
465                 470                 475                 480

Ser Phe Thr Pro Val Cys Gly Ala Asp Gly Ile Thr Tyr Leu Ser Ala
                485                 490                 495

Cys Phe Ala Gly Cys Asn Ser Thr Asn Leu Thr Gly Cys Ala Cys Leu
            500                 505                 510

Thr Thr Val Pro Ala Glu Asn Ala Thr Val Pro Gly Lys Cys Pro
        515                 520                 525

Ser Pro Gly Cys Gln Glu Ala Phe Leu Thr Phe Leu Cys Val Met Cys
        530                 535                 540

Ile Cys Ser Leu Ile Gly Ala Met Ala Gln Thr Pro Ser Val Ile Ile
545                 550                 555                 560

Leu Ile Arg Thr Val Ser Pro Glu Leu Lys Ser Tyr Ala Leu Gly Val
                565                 570                 575

Leu Phe Leu Leu Leu Arg Leu Leu Gly Phe Ile Pro Pro Leu Ile
            580                 585                 590

Phe Gly Ala Gly Ile Asp Ser Thr Cys Leu Phe Trp Ser Thr Phe Cys
```

```
            595                 600                 605
Gly Glu Gln Gly Ala Cys Val Leu Tyr Asp Asn Val Val Tyr Arg Tyr
    610                 615                 620

Leu Tyr Val Ser Ile Ala Ile Ala Leu Lys Ser Phe Ala Phe Ile Leu
625                 630                 635                 640

Tyr Thr Thr Thr Trp Gln Cys Leu Arg Lys Asn Tyr Lys Arg Tyr Ile
                645                 650                 655

Lys Asn His Glu Gly Gly Leu Ser Thr Ser Glu Phe Phe Ala Ser Thr
                660                 665                 670

Leu Thr Leu Asp Asn Leu Gly Arg Asp Pro Val Pro Ala Asn Gln Thr
                675                 680                 685

His Arg Thr Lys Phe Ile Tyr Asn Leu Glu Asp His Glu Trp Cys Glu
    690                 695                 700

Asn Met Glu Ser Val Leu
705             710

<210> SEQ ID NO 7
<211> LENGTH: 3692
<212> TYPE: DNA
<213> ORGANISM: Homo sapiens
<220> FEATURE:
<221> NAME/KEY: misc_feature
<222> LOCATION: (713)
<223> OTHER INFORMATION: y = c or t
<220> FEATURE:
<221> NAME/KEY: misc_feature
<222> LOCATION: (2397)
<223> OTHER INFORMATION: k = g or t

<400> SEQUENCE: 7
ctgatttctc ttcggctgga cggaggctgc ctcctcacgc ggctcccaac tattcccgta      60
gctcagtgcc cccctcccgc cgctctactc agccaggcag acagactgac agactcgcta     120
gtcggcagct tcactcccga gggtgccgcg agcccaggcg gcgaacaccc ggtacccctg     180
gcgcagcgag gtgggatgct gtacggacag cagcgctaag tgccccccca ccccggcgc     240 agggtgcact cgctcctggc cgcgggccca cggcgcgcgg cggcggcggc ggcggagggg     300
atgagcccgg gacgcgcgag gcgcctgcct caagctaccg cccggagagg gacgccgagt     360
agggctcatc gcagtaccgc gcggacccct gccccctgtg gcacgcggct gcggagcctt     420
gaagccgtgt ctgtgatcag gatgcactgg gcgcctcgca gctggtgagg atgccctgct     480
gcgcggccct cgcgccccag ccccagtccc agtgggcaa gactgactgg gcccggcttc     540
ggcccctcgt gccggtggat gaaacgtgcc ggagtgcttg ggtgccatca gctatcaaat     600
ctgaattcta agcgccatgg acgaaggcac tggactgcag cccggggcgg gagagcagct     660
ggaggcgccg gccactgcag aagctgtcca agagaggtgc gagccggaga ccytcaggtc     720
taagagttta ccggtcctca gcagcgcctc ctgccggcca agcctcagtc ccactagtgg     780
agacgccaac ccggcctttg gctgtgtgga ttcttcgggc caccaggagt tgaagcaagg     840
cccgaacccg ttggccccca gtccctctgc cccgtccact tcggcgggc tcggggactg     900 taaccacagg gtggacctca gcaaaacctt ctcggtgtcc tccgccttgg ccatgctcca     960
ggagagaagg tgcctctacg tggtcctcac ggattcccgt tgcttcctgg tgtgcatgtg    1020
ctttctgacc ttcatccagg cgttaatggt ctctgggtac ctgagcagcg taattaccac    1080
cattgaaagg cgctacagtc tgaagagttc cgagtcgggg ctgctggtca gctgctttga    1140
catcgggaac ctggtggtgg tggtgttcgt cagctacttc ggcggccggg gtcggcggcc    1200
```

```
cctgtggctg gccgtgggtg gactcctcat cgccttcggg gcagccctct tcgccttacc    1260
tcacttcatc tcgccccccct accagatcca agagttgaac gcctcggccc ccaacgacgg    1320
cctgtgtcag ggtggcaact ccaccgccac tttggagcct ccggcctgtc cgaaggactc    1380
gggaggaaat aatcactggg tctacctggc tttattcatt tgcgcgcaga ttctcattgg    1440
aatgggctcc acacctattt ataccctggg accaacctac ttagatgaca atgtcaagaa    1500
agaaaactcc tccttgtacc tagccatcat gtatgtcatg ggagcacttg gccctgcagt    1560
gggatattta ttaggtggac ttcttattgg tttttatgtt gatcccagaa atcctgttca    1620
ccttgaccag aatgaccctc gtttcattgg aaactggtgg agtggattcc tcctttgtgc    1680
cattgcaatg tttcttgtga tattcccaat gtttactttc ccaaaaaagc ttccacctcg    1740
acacaagaaa aagaaaaaga aaaattttc tgttgatgct gttagtgatg acgatgttct    1800
gaaggagaaa tcaaacaaca gtgaacaagc ggacaaaaaa gtttcttcga tgggatttgg    1860
aaaggatgtc agagacctac caagagcagc tgtcaggatc ttaagcaaca tgacattcct    1920
ttttgtgagt ttgtcataca cagctgagag tgccattgta actgctttca ttaccttcat    1980
tcccaagttc atcgagtcac agtttggtat cccagcctcc aatgccagca tctacactgg    2040
ggttattatc gtccccagtg ctggtgttgg tattgtcctc ggaggctaca ttataaaaaa    2100
attgaaactt ggtgccagag aatctgcaaa actagcaatg atctgcagtg gtgtgtcttt    2160
actatgtttt tcaaccctat ttattgttgg atgtgaaagc attaatctag ggggcataaa    2220
catcccttat acaacaggac cttctctcac catgccccat aggaatctga caggaagctg    2280
caacgttaat tgtggttgta aaatacacga gtatgagcca gtctgtggat cagatggaat    2340
tacatacttt aacccttgtc tggctggctg tgttaatagt ggtaatctta gcactgkgat    2400
acggaattat acagaatgca cctgtgtcca aagtcgccaa gtgatcactc cacccaccgt    2460
gggacagcga agtcagctcc gtgtggttat tgtcaagact tatctcaatg agaacggcta    2520
tgctgtgtct gggaaatgta acggacctg caatactctt atcccattct tagttttttct    2580 tttcatagtc accttcatca cagcatgtgc ccaaccatca gctatcatag taacactcag    2640
gtccgtagaa gatgaggaga ccttttgc actgggaatg cagtttgttt tgttgcgaac    2700
acttgcatac attcctactc caatctactt tggagcagtc attgacacca cctgcatgct    2760
ctggcaacag gaatgtggtg tgcagggttc ttgctgggag tacaacgtga cgtcgtttcg    2820
ttttgtgtat tttggtttgg ctgccggcct caaattcgtt gggtttattt ttattttttct    2880 ggcctggtac tccataaaat acaaggagga tggactgcag aggcggaggc agagagaatt    2940 tccccctgagc accgtgagtg agagagtggg acaccccgac aatgcccgga ctagatcttg    3000
cccagctttc agcacccagg gagaattcca cgaagagact ggcctgcaaa aagggatcca    3060
gtgcgcagca cagacctacc cggggcccctt cccagaagca ataagttcct ctgcggaccc    3120
ggggctggaa gagagccccg ctgccttgga gccgccctcc tgaagcttga aaatggaaga    3180 atttagttttt gttggttgaa ttgaaatgg cgacttgaga acaactgtg ccttctttc    3240 tttctttctt tttttaacc tctacagaca caatcctcaa accaacaaaa ctcagtatac    3300
acagccgcta ttcattgagg ctggatacc tcaacaagac tgagagcctt tccccgcttc    3360
tctccaagaa ggagacgttc agctagattt gttcccattt ccgttgtgtt aattcaaagc    3420
tcatgctccc ctacggtaca ggctgaggta cacggttagc aaaaccatgg gaagggggaat    3480 ggcggtgcat atcattaact aacactccaa acaaaggtga gcttgcccag gacttggcat    3540
ttccaaatca aagttttag atatgaacac ctactgtgag ttctgctaca aagcacaaat    3600
```

```
gaatttgtct caactatgca atttgattgg aaaaatgtat gtgcagcatg ttacatttac    3660
tttcacggaa taaagcagat atgtttctga aa                                  3692

<210> SEQ ID NO 8
<211> LENGTH: 848
<212> TYPE: PRT
<213> ORGANISM: Homo sapiens
<220> FEATURE:
<221> NAME/KEY: PEPTIDE
<222> LOCATION: (33)
<223> OTHER INFORMATION: Xaa = Leu or Phe
<220> FEATURE:
<221> NAME/KEY: PEPTIDE
<222> LOCATION: (594)
<223> OTHER INFORMATION: Xaa = Gly or Val

<400> SEQUENCE: 8

Met Asp Glu Gly Thr Gly Leu Gln Pro Gly Ala Gly Glu Gln Leu Glu
 1               5                  10                  15

Ala Pro Ala Thr Ala Glu Ala Val Gln Glu Arg Cys Glu Pro Glu Thr
             20                  25                  30

Xaa Arg Ser Lys Ser Leu Pro Val Leu Ser Ser Ala Ser Cys Arg Pro
         35                  40                  45

Ser Leu Ser Pro Thr Ser Gly Asp Ala Asn Pro Ala Phe Gly Cys Val
     50                  55                  60

Asp Ser Ser Gly His Gln Glu Leu Lys Gln Gly Pro Asn Pro Leu Ala
 65                  70                  75                  80

Pro Ser Pro Ser Ala Pro Ser Thr Ser Ala Gly Leu Gly Asp Cys Asn
                 85                  90                  95

His Arg Val Asp Leu Ser Lys Thr Phe Ser Val Ser Ser Ala Leu Ala
            100                 105                 110

Met Leu Gln Glu Arg Arg Cys Leu Tyr Val Val Leu Thr Asp Ser Arg
        115                 120                 125

Cys Phe Leu Val Cys Met Cys Phe Leu Thr Phe Ile Gln Ala Leu Met
    130                 135                 140

Val Ser Gly Tyr Leu Ser Ser Val Ile Thr Thr Ile Glu Arg Arg Tyr
145                 150                 155                 160

Ser Leu Lys Ser Ser Glu Ser Gly Leu Leu Val Ser Cys Phe Asp Ile
                165                 170                 175

Gly Asn Leu Val Val Val Val Phe Val Ser Tyr Phe Gly Gly Arg Gly
            180                 185                 190

Arg Arg Pro Leu Trp Leu Ala Val Gly Gly Leu Leu Ile Ala Phe Gly
        195                 200                 205

Ala Ala Leu Phe Ala Leu Pro His Phe Ile Ser Pro Tyr Gln Ile
    210                 215                 220

Gln Glu Leu Asn Ala Ser Ala Pro Asn Asp Gly Leu Cys Gln Gly Gly
225                 230                 235                 240

Asn Ser Thr Ala Thr Leu Glu Pro Pro Ala Cys Pro Lys Asp Ser Gly
                245                 250                 255

Gly Asn Asn His Trp Val Tyr Leu Ala Leu Phe Ile Cys Ala Gln Ile
            260                 265                 270

Leu Ile Gly Met Gly Ser Thr Pro Ile Tyr Thr Leu Gly Pro Thr Tyr
        275                 280                 285

Leu Asp Asp Asn Val Lys Lys Glu Asn Ser Ser Leu Tyr Leu Ala Ile
    290                 295                 300

Met Tyr Val Met Gly Ala Leu Gly Pro Ala Val Gly Tyr Leu Leu Gly
```

-continued

```
            305                 310                 315                 320
Gly Leu Leu Ile Gly Phe Tyr Val Asp Pro Arg Asn Pro Val His Leu
                    325                 330                 335
Asp Gln Asn Asp Pro Arg Phe Ile Gly Asn Trp Trp Ser Gly Phe Leu
                340                 345                 350
Leu Cys Ala Ile Ala Met Phe Leu Val Ile Phe Pro Met Phe Thr Phe
            355                 360                 365
Pro Lys Lys Leu Pro Pro Arg His Lys Lys Lys Lys Lys Lys Lys Phe
        370                 375                 380
Ser Val Asp Ala Val Ser Asp Asp Val Leu Lys Glu Lys Ser Asn
385                 390                 395                 400
Asn Ser Glu Gln Ala Asp Lys Lys Val Ser Ser Met Gly Phe Gly Lys
                405                 410                 415
Asp Val Arg Asp Leu Pro Arg Ala Ala Val Arg Ile Leu Ser Asn Met
                420                 425                 430
Thr Phe Leu Phe Val Ser Leu Ser Tyr Thr Ala Glu Ser Ala Ile Val
                435                 440                 445
Thr Ala Phe Ile Thr Phe Ile Pro Lys Phe Ile Glu Ser Gln Phe Gly
            450                 455                 460
Ile Pro Ala Ser Asn Ala Ser Ile Tyr Thr Gly Val Ile Ile Val Pro
465                 470                 475                 480
Ser Ala Gly Val Gly Ile Val Leu Gly Gly Tyr Ile Ile Lys Lys Leu
                485                 490                 495
Lys Leu Gly Ala Arg Glu Ser Ala Lys Leu Ala Met Ile Cys Ser Gly
                500                 505                 510
Val Ser Leu Leu Cys Phe Ser Thr Leu Phe Ile Val Gly Cys Glu Ser
                515                 520                 525
Ile Asn Leu Gly Gly Ile Asn Ile Pro Tyr Thr Thr Gly Pro Ser Leu
                530                 535                 540
Thr Met Pro His Arg Asn Leu Thr Gly Ser Cys Asn Val Asn Cys Gly
545                 550                 555                 560
Cys Lys Ile His Glu Tyr Glu Pro Val Cys Gly Ser Asp Gly Ile Thr
                565                 570                 575
Tyr Phe Asn Pro Cys Leu Ala Gly Cys Val Asn Ser Gly Asn Leu Ser
                580                 585                 590
Thr Xaa Ile Arg Asn Tyr Thr Glu Cys Thr Cys Val Gln Ser Arg Gln
            595                 600                 605
Val Ile Thr Pro Pro Thr Val Gly Gln Arg Ser Gln Leu Arg Val Val
        610                 615                 620
Ile Val Lys Thr Tyr Leu Asn Glu Asn Gly Tyr Ala Val Ser Gly Lys
625                 630                 635                 640
Cys Lys Arg Thr Cys Asn Thr Leu Ile Pro Phe Leu Val Phe Leu Phe
                645                 650                 655
Ile Val Thr Phe Ile Thr Ala Cys Ala Gln Pro Ser Ala Ile Ile Val
                660                 665                 670
Thr Leu Arg Ser Val Glu Asp Glu Arg Pro Phe Ala Leu Gly Met
                675                 680                 685
Gln Phe Val Leu Leu Arg Thr Leu Ala Tyr Ile Pro Thr Pro Ile Tyr
        690                 695                 700
Phe Gly Ala Val Ile Asp Thr Thr Cys Met Leu Trp Gln Gln Glu Cys
705                 710                 715                 720
Gly Val Gln Gly Ser Cys Trp Glu Tyr Asn Val Thr Ser Phe Arg Phe
                725                 730                 735
```

```
Val Tyr Phe Gly Leu Ala Ala Gly Leu Lys Phe Val Gly Phe Ile Phe
            740                 745                 750

Ile Phe Leu Ala Trp Tyr Ser Ile Lys Tyr Lys Glu Asp Gly Leu Gln
            755                 760                 765

Arg Arg Arg Gln Arg Glu Phe Pro Leu Ser Thr Val Ser Glu Arg Val
            770                 775                 780

Gly His Pro Asp Asn Ala Arg Thr Arg Ser Cys Pro Ala Phe Ser Thr
785                 790                 795                 800

Gln Gly Glu Phe His Glu Glu Thr Gly Leu Gln Lys Gly Ile Gln Cys
                805                 810                 815

Ala Ala Gln Thr Tyr Pro Gly Pro Phe Pro Glu Ala Ile Ser Ser Ser
            820                 825                 830

Ala Asp Pro Gly Leu Glu Glu Ser Pro Ala Ala Leu Glu Pro Pro Ser
            835                 840                 845

<210> SEQ ID NO 9
<211> LENGTH: 3381
<212> TYPE: DNA
<213> ORGANISM: Homo sapiens

<400> SEQUENCE: 9
cgcaaagaaa tggctcaaaa gcttcagctc tttctgtgcc ctgggagctg agatgcacgt      60
cagtggcctt gccagcgtgg ccaattctct gctgactgcc agaaaaaaga ggccaggaag     120
aaagaggaaa gagaagagat cgctcagggg tgagaccatg cccttcatct tttcttttcc     180
ctaatctcct ctgcttgtgt ccacccacac tctccccacc tggcaaaatt gttcaaaatt     240
gctgtggagt ttacctcagt ttcctctttc agtctgtggt gtgtggtcca tcctcttgct     300
gagcacattg aaaggaactg ctatctttg atctcttcct ccagatcaga gtcaaggaat     360
gtgtttataa tggacacttc atccaaagaa aatatccagt tgttctgcaa aacttcagtg     420
caacctgttg aaggccttc ttttaaaaca gaatatccct cctcagaaga aaagcaacca     480
tgctgtggtg aactaaaggt gttcttgtgt gccttgtctt tgtttactt tgccaaagca     540
ttggcagaag gctatctgaa gagcaccatc actcagatag agagaaggtt tgatatccct     600
tcttcactgg tgggagttat tgatggtagt tttgaaattg ggaatctctt agttataaca     660
tttgttagct actttggagc caaacttcac aggccaaaaa taattggagc agggtgtgta     720
atcatgggag ttggaacact gctcattgca atgcctcagt tcttcatgga gcagtacaaa     780
tatgagagat attctccttc ctccaattcc actctcagca tctctccgtg tctcctagag     840
tcaagcagtc aattaccagt ttcagttatg gaaaaatcaa atccaaaat aagtaacgaa     900
tgtgaagtgg acactagctc ttccatgtgg atttatgttt tcctgggcaa tcttcttcgt     960
ggaataggag aaactcccat tcagcctttg ggcattgcct acctggatga ttttgccagt    1020
gaagacaatg cagcttttcta tattgggtgt gtgcagacgg ttgcaattat aggaccaatc    1080
tttggttttcc tgttaggctc attatgtgcc aaactatatg ttgacattgg ctttgtaaac    1140
ctagatcaca taaccattac cccaaaagat ccccagtggg taggagcctg gtggcttggc    1200
tatctaatag caggaatcat aagtcttctt gcagctgtgc ctttctggta tttaccaaag    1260
agttaccaa gatcccaaag tagagaggat tctaattctt cctctgagaa atccaagttt    1320
attatagatg atcacacaga ctaccaaaca ccccagggag aaaatgcaaa aataatggaa    1380
atggcaagag attttcttcc atcactgaag aatcttttg gaaacccagt atacttccta    1440
tatttatgta caagcactgt tcagttcaat tctctgttcg gcatggtgac gtacaaacca    1500
```

-continued

```
aagtacattg agcagcagta tggacagtca tcctccaggg ccaactttgt gatcgggctc    1560
atcaacattc cagcagtggc ccttggaata ttctctgggg ggatagttat gaaaaaattc    1620
agaatcagtg tgtgtggagc tgcaaaactc tacttgggat catctgtctt tggttacctc    1680
ctatttcttt ccctgtttgc actgggctgt gaaaattctg atgtggcagg actaactgtc    1740
tcctaccaag gaaccaaacc tgtctcttat catgaacgag ctctcttttc agattgcaac    1800
tcaagatgca aatgttcaga gacaaaatgg gaacccatgt gcggtgaaaa tggaatcaca    1860
tatgtatcag cttgtcttgc tggttgtcaa acctccaaca ggagtggaaa aaatattata    1920
ttttacaact gcacttgtgt gggaattgca gcttctaaat ccggaaattc ctcaggcata    1980
gtgggaagat gtcagaaaga caatggatgt ccccaaatgt ttctgtattt ccttgtaatt    2040
tcagtcatca catcctatac tttatcccta ggtggcatac ctggatacat attacttctg    2100
aggtgcatta agccacagct taagtctttt gccttgggta tctacacatt agcaataaga    2160
gttcttgcag gaatcccagc tccagtgtat tttggagttt tgattgatac ttcatgcctc    2220
aaatggggat ttaaaagatg tggaagtaga ggatcatgca gattatatga ttcaaatgtc    2280
ttcagacata tatatttggg actaactgtg atactgggca cagtgtcaat tctcctaagc    2340
attgcagtac ttttcatttt aaagaaaaat tatgtttcaa acacagaag ttttataacc     2400 aagagagaaa gaacaatggt gtctacaaga ttccaaaagg aaaattacac tacaagtgat    2460
catctgctac aacccaacta ctggccaggc aaggaaactc aactttagaa acatgatgac    2520
tggaagtcat gtcttctaat tggttgacat tttgcaaaca aataaattgt aatcaaaaga    2580
gctctaaatt tgtaatttct ttctcctttc aaaaaatgtc tactttgttt tggtcctagg    2640
cattaggtaa tataactgat aatatactga atatatataat ggaagatgca gatgataaaa   2700
ctaattttga acttttttaat ttatataaat tattttatat catttactta tttcacttta   2760
ttttgctttg tgctcattga tatatattag ctgtactcct agaagaacaa ttgtctctat    2820
tgtcacacat ggttatattt aaagtaattt ctgaactgtg taatgtgtct agagtaagca    2880
aatactgcta acaattaact cataccttgg gttccttcaa gtattactcc tatagtattt    2940
tctcccatag ctgtcttcat ctgtgtattt taataatgat cttaggatgg agcagaacat    3000
ggagaggaag atttcatttt aagctcctcc ttttccttga aatacaataa tttatataga    3060
aatgtgtagc agcaaattat attggggatt agaattttga attaatagct ctcctactat    3120
taatttacat gtgcttttg tgtggcgcta aagtgacta tggttgtaaa gtaataaaat      3180
tgatgttaac atgcccaatt attgttcttt tatgaattca atgaatttaa aactattgtt    3240
aaatataata ctgcccact ttaatatatg taagcaactt cctacttata cacgacgtgt     3300
tcctaaaaca tgtttgaaag gtgaatttct gaaagtctcc cataaatgta ggtgttacaa    3360
caggaaaaaa aaaaaaaaa a                                               3381
```

<210> SEQ ID NO 10
<211> LENGTH: 712
<212> TYPE: PRT
<213> ORGANISM: Homo sapiens

<400> SEQUENCE: 10

```
Met Asp Thr Ser Ser Lys Glu Asn Ile Gln Leu Phe Cys Lys Thr Ser
  1               5                  10                  15

Val Gln Pro Val Gly Arg Pro Ser Phe Lys Thr Glu Tyr Pro Ser Ser
             20                  25                  30
```

```
Glu Glu Lys Gln Pro Cys Cys Gly Glu Leu Lys Val Phe Leu Cys Ala
         35                  40                  45

Leu Ser Phe Val Tyr Phe Ala Lys Ala Leu Ala Glu Gly Tyr Leu Lys
         50                  55                  60

Ser Thr Ile Thr Gln Ile Glu Arg Arg Phe Asp Ile Pro Ser Ser Leu
 65                  70                  75                  80

Val Gly Val Ile Asp Gly Ser Phe Glu Ile Gly Asn Leu Leu Val Ile
                 85                  90                  95

Thr Phe Val Ser Tyr Phe Gly Ala Lys Leu His Arg Pro Lys Ile Ile
                100                 105                 110

Gly Ala Gly Cys Val Ile Met Gly Val Gly Thr Leu Leu Ile Ala Met
             115                 120                 125

Pro Gln Phe Phe Met Glu Gln Tyr Lys Tyr Glu Arg Tyr Ser Pro Ser
         130                 135                 140

Ser Asn Ser Thr Leu Ser Ile Ser Pro Cys Leu Leu Glu Ser Ser Ser
145                 150                 155                 160

Gln Leu Pro Val Ser Val Met Glu Lys Ser Lys Ser Lys Ile Ser Asn
                165                 170                 175

Glu Cys Glu Val Asp Thr Ser Ser Ser Met Trp Ile Tyr Val Phe Leu
             180                 185                 190

Gly Asn Leu Leu Arg Gly Ile Gly Glu Thr Pro Ile Gln Pro Leu Gly
         195                 200                 205

Ile Ala Tyr Leu Asp Asp Phe Ala Ser Glu Asp Asn Ala Ala Phe Tyr
         210                 215                 220

Ile Gly Cys Val Gln Thr Val Ala Ile Ile Gly Pro Ile Phe Gly Phe
225                 230                 235                 240

Leu Leu Gly Ser Leu Cys Ala Lys Leu Tyr Val Asp Ile Gly Phe Val
                245                 250                 255

Asn Leu Asp His Ile Thr Ile Thr Pro Lys Asp Pro Gln Trp Val Gly
             260                 265                 270

Ala Trp Trp Leu Gly Tyr Leu Ile Ala Gly Ile Ile Ser Leu Leu Ala
         275                 280                 285

Ala Val Pro Phe Trp Tyr Leu Pro Lys Ser Leu Pro Arg Ser Gln Ser
         290                 295                 300

Arg Glu Asp Ser Asn Ser Ser Glu Lys Ser Lys Phe Ile Ile Asp
305                 310                 315                 320

Asp His Thr Asp Tyr Gln Thr Pro Gln Gly Glu Asn Ala Lys Ile Met
             325                 330                 335

Glu Met Ala Arg Asp Phe Leu Pro Ser Leu Lys Asn Leu Phe Gly Asn
             340                 345                 350

Pro Val Tyr Phe Leu Tyr Leu Cys Thr Ser Thr Val Gln Phe Asn Ser
         355                 360                 365

Leu Phe Gly Met Val Thr Tyr Lys Pro Lys Tyr Ile Glu Gln Gln Tyr
         370                 375                 380

Gly Gln Ser Ser Ser Arg Ala Asn Phe Val Ile Gly Leu Ile Asn Ile
385                 390                 395                 400

Pro Ala Val Ala Leu Gly Ile Phe Ser Gly Ile Val Met Lys Lys
                405                 410                 415

Phe Arg Ile Ser Val Cys Gly Ala Ala Lys Leu Tyr Leu Gly Ser Ser
                420                 425                 430

Val Phe Gly Tyr Leu Leu Phe Leu Ser Leu Phe Ala Leu Gly Cys Glu
             435                 440                 445

Asn Ser Asp Val Ala Gly Leu Thr Val Ser Tyr Gln Gly Thr Lys Pro
```

-continued

```
           450               455                460
Val Ser Tyr His Glu Arg Ala Leu Phe Ser Asp Cys Asn Ser Arg Cys
465                 470                 475                 480

Lys Cys Ser Glu Thr Lys Trp Glu Pro Met Cys Gly Glu Asn Gly Ile
                485                 490                 495

Thr Tyr Val Ser Ala Cys Leu Ala Gly Cys Gln Thr Ser Asn Arg Ser
            500                 505                 510

Gly Lys Asn Ile Ile Phe Tyr Asn Cys Thr Cys Val Gly Ile Ala Ala
        515                 520                 525

Ser Lys Ser Gly Asn Ser Ser Gly Ile Val Gly Arg Cys Gln Lys Asp
530                 535                 540

Asn Gly Cys Pro Gln Met Phe Leu Tyr Phe Leu Val Ile Ser Val Ile
545                 550                 555                 560

Thr Ser Tyr Thr Leu Ser Leu Gly Gly Ile Pro Gly Tyr Ile Leu Leu
                565                 570                 575

Leu Arg Cys Ile Lys Pro Gln Leu Lys Ser Phe Ala Leu Gly Ile Tyr
                580                 585                 590

Thr Leu Ala Ile Arg Val Leu Ala Gly Ile Pro Ala Pro Val Tyr Phe
            595                 600                 605

Gly Val Leu Ile Asp Thr Ser Cys Leu Lys Trp Gly Phe Lys Arg Cys
        610                 615                 620

Gly Ser Arg Gly Ser Cys Arg Leu Tyr Asp Ser Asn Val Phe Arg His
625                 630                 635                 640

Ile Tyr Leu Gly Leu Thr Val Ile Leu Gly Thr Val Ser Ile Leu Leu
                645                 650                 655

Ser Ile Ala Val Leu Phe Ile Leu Lys Lys Asn Tyr Val Ser Lys His
                660                 665                 670

Arg Ser Phe Ile Thr Lys Arg Glu Arg Thr Met Val Ser Thr Arg Phe
            675                 680                 685

Gln Lys Glu Asn Tyr Thr Thr Ser Asp His Leu Leu Gln Pro Asn Tyr
        690                 695                 700

Trp Pro Gly Lys Glu Thr Gln Leu
705                 710
```

<210> SEQ ID NO 11
<211> LENGTH: 2763
<212> TYPE: DNA
<213> ORGANISM: Homo sapiens

<400> SEQUENCE: 11

| | | | | | |
|---|---|---|---|---|---|
| ggcacgaggc | gctgcgcggc | gcggcggccg | ggccctcgag | acggggacgg | acacaccagc | 60 |
| ccctcggata | ccacttggcc | actcccgctg | aggccactcc | cactgcgtgg | ctgaagcctc | 120 |
| gaggtcacca | ggcggaggcg | cggagatgcc | cctgcatcag | ctgggggaca | agccgctcac | 180 |
| cttccccagc | cccaactcag | ccatggaaaa | cgggcttgac | cacaccccac | ccagcaggag | 240 |
| ggcatccccg | ggcacacccc | tgagccccgg | gtccctccgc | tccgctgccc | atagccccct | 300 |
| ggacaccagc | aagcagcccc | tctgccagct | ctgggccgag | aagcatggcg | cccgggggac | 360 |
| ccatgaggtg | cggtacgtct | cggccgggca | gagcgtggcg | tgcggctggt | gggccttcgc | 420 |
| accgccgtgc | ctgcaggtcc | tcaacacgcc | caagggcatc | ctgttcttcc | tgtgtgcggc | 480 |
| cgcattcctg | cagggatga | ctgtgaatgg | cttcatcaac | acagtcatca | cctccctgga | 540 |
| gcgccgctat | gacctgcaca | gctaccagag | cgggctcatc | gccagctcct | acgacattgc | 600 |
| cgcctgcctc | tgcctcacct | tcgtcagcta | cttcggggc | tcagggcaca | agccgcgctg | 660 |

```
gctgggctgg ggcgtgctgc ttatgggcac ggggtcgctg gtgttcgcgc tgccccactt    720
cacggctggc cgctatgagg tggagttgga cgcgggtgtc aggacgtgcc ctgccaaccc    780
cggcgcggtg tgtgcggaca gcacctcggg cctgtcccgc taccagctgg tcttcatgct    840
gggccagttc ctgcatggcg tgggtgccac acccctctac acgctgggcg tcacctacct    900
ggatgagaac gtcaagtcca gctgctcgcc cgtctacatt gccatcttct acacagcggc    960
catcctgggc ccagctgccg gctacctgat tggaggtgcc ctgctgaata tctacacgga   1020
aatgggccga cggacggagc tgaccaccga gagcccactg tgggtcggcg cctggtgggt   1080
cggcttcctg ggctctgggg ccgctgcttt cttcaccgcc gttcccatcc ttggttaccc   1140
tcggcagctg ccaggctccc agcgctacgc ggtcatgaga gcggcggaaa tgcaccagtt   1200
gaaggacagc agccgtgggg aggcgagcaa cccggacttt gggaaaacca tcagagacct   1260
gcctctctcc atctggctcc tgctgaagaa ccccacgttc atcctgctct gcctggccgg   1320
ggccaccgag gccactctca tcaccggcat gtccacgttc agccccaagt tcttggagtc   1380
ccagttcagc ctgagtgcct cagaagctgc caccttgttt gggtacctgg tggtgccagc   1440
gggtggtggc ggcaccttcc tgggcggctt ctttgtgaac aagctcaggc tccggggctc   1500
cgcggtcatc aagttctgcc tgttctgcac cgttgtcagc ctgctgggca tcctcgtctt   1560
ctcactgcac tgccccagtg tgcccatggc gggcgtcaca gccagctacg gcgggagcct   1620
cctgcccgaa ggccacctga acctaacggc tccctgcaac gctgcctgca gctgccagcc   1680
agaacactac agccctgtgt gcggctcgga cggcctcatg tacttctcac tgtgccacgc   1740
agggtgccct gcagccacgg agacgaatgt ggacggccag aaggtgtacc gagactgtag   1800
ctgtatccct cagaatcttt cctctggttt tggccatgcc actgcaggga atgcacttc    1860
aacttgtcag agaaagcccc tccttctggt tttcatattc gttgtaattt tctttacatt   1920
cctcagcagc attcctgcac taacggcaac tctacgatgt gtccgtgacc ctcagagatc   1980
ctttgccctg ggaatccagt ggattgtagt tagaatacta gggggcatcc cggggcccat   2040
cgccttcggc tgggtgatcg acaaggcctg tctgctgtgg caggaccagt gtggccagca   2100
gggctcctgc ttggtgtacc agaattcggc catgagccgc tacatactca tcatggggct   2160
cctgtacaag gtgctgggcg tcctcttctt gccatagcc tgcttcttat acaagccct     2220
gtcggagtct tcagatggcc tggaaacttg tctgcccagc cagtcctcag cccctgacag   2280
tgccacagat agccagctcc agagcagcgt ctgaccaccg cccgcgccca ccggccacg    2340
gcgggcactc agcatttcct gatgacagaa cagtgccgtt gggtgatgca atcacacggg   2400
aacttctatt tgacctgcaa ccttctactt aacctgtggt ttaaagtcgg ctgtgacctc   2460
ctgtccccag agctgtacgg ccctgcagtg ggtgggagga acttgcataa atatatattt   2520
atggacacac agtttgcatc agaacgtgtt tatagaatgt gttttatacc cgatcgtgtg   2580
tggtgtgcgt gaggacaaac tccgcagggg ctgtgaatcc cactgggagg gcggcgggcc   2640
tgcagcccga ggaaggcttg tgtgtcctca gttaaaactg tgcatatcga aatatatttt   2700
gttatttaag cctgcgaaaa aaaaaaaaaa aaaaaaaaaa aaaaaaaaaa aaaaaaaaaa   2760
aaa                                                                 2763
```

<210> SEQ ID NO 12
<211> LENGTH: 722
<212> TYPE: PRT
<213> ORGANISM: Homo sapiens

```
<400> SEQUENCE: 12

Met Pro Leu His Gln Leu Gly Asp Lys Pro Leu Thr Phe Pro Ser Pro
  1               5                  10                  15

Asn Ser Ala Met Glu Asn Gly Leu Asp His Thr Pro Pro Ser Arg Arg
             20                  25                  30

Ala Ser Pro Gly Thr Pro Leu Ser Pro Gly Ser Leu Arg Ser Ala Ala
         35                  40                  45

His Ser Pro Leu Asp Thr Ser Lys Gln Pro Leu Cys Gln Leu Trp Ala
     50                  55                  60

Glu Lys His Gly Ala Arg Gly Thr His Glu Val Arg Tyr Val Ser Ala
 65                  70                  75                  80

Gly Gln Ser Val Ala Cys Gly Trp Trp Ala Phe Ala Pro Pro Cys Leu
                 85                  90                  95

Gln Val Leu Asn Thr Pro Lys Gly Ile Leu Phe Phe Leu Cys Ala Ala
            100                 105                 110

Ala Phe Leu Gln Gly Met Thr Val Asn Gly Phe Ile Asn Thr Val Ile
            115                 120                 125

Thr Ser Leu Glu Arg Arg Tyr Asp Leu His Ser Tyr Gln Ser Gly Leu
130                 135                 140

Ile Ala Ser Ser Tyr Asp Ile Ala Ala Cys Leu Cys Leu Thr Phe Val
145                 150                 155                 160

Ser Tyr Phe Gly Gly Ser Gly His Lys Pro Arg Trp Leu Gly Trp Gly
                165                 170                 175

Val Leu Leu Met Gly Thr Gly Ser Leu Val Phe Ala Leu Pro His Phe
            180                 185                 190

Thr Ala Gly Arg Tyr Glu Val Glu Leu Asp Ala Gly Val Arg Thr Cys
            195                 200                 205

Pro Ala Asn Pro Gly Ala Val Cys Ala Asp Ser Thr Ser Gly Leu Ser
        210                 215                 220

Arg Tyr Gln Leu Val Phe Met Leu Gly Gln Phe Leu His Gly Val Gly
225                 230                 235                 240

Ala Thr Pro Leu Tyr Thr Leu Gly Val Thr Tyr Leu Asp Glu Asn Val
                245                 250                 255

Lys Ser Ser Cys Ser Pro Val Tyr Ile Ala Ile Phe Tyr Thr Ala Ala
            260                 265                 270

Ile Leu Gly Pro Ala Ala Gly Tyr Leu Ile Gly Gly Ala Leu Leu Asn
        275                 280                 285

Ile Tyr Thr Glu Met Gly Arg Arg Thr Glu Leu Thr Thr Glu Ser Pro
    290                 295                 300

Leu Trp Val Gly Ala Trp Trp Val Gly Phe Leu Gly Ser Gly Ala Ala
305                 310                 315                 320

Ala Phe Phe Thr Ala Val Pro Ile Leu Gly Tyr Pro Arg Gln Leu Pro
                325                 330                 335

Gly Ser Gln Arg Tyr Ala Val Met Arg Ala Ala Glu Met His Gln Leu
            340                 345                 350

Lys Asp Ser Ser Arg Gly Glu Ala Ser Asn Pro Asp Phe Gly Lys Thr
        355                 360                 365

Ile Arg Asp Leu Pro Leu Ser Ile Trp Leu Leu Leu Lys Asn Pro Thr
    370                 375                 380

Phe Ile Leu Leu Cys Leu Ala Gly Ala Thr Glu Ala Thr Leu Ile Thr
385                 390                 395                 400

Gly Met Ser Thr Phe Ser Pro Lys Phe Leu Glu Ser Gln Phe Ser Leu
                405                 410                 415
```

-continued

Ser Ala Ser Glu Ala Ala Thr Leu Phe Gly Tyr Leu Val Val Pro Ala
                420                 425                 430

Gly Gly Gly Gly Thr Phe Leu Gly Phe Phe Val Asn Lys Leu Arg
            435                 440                 445

Leu Arg Gly Ser Ala Val Ile Lys Phe Cys Leu Phe Cys Thr Val Val
    450                 455                 460

Ser Leu Leu Gly Ile Leu Val Phe Ser Leu His Cys Pro Ser Val Pro
465                 470                 475                 480

Met Ala Gly Val Thr Ala Ser Tyr Gly Ser Leu Leu Pro Glu Gly
                485                 490                 495

His Leu Asn Leu Thr Ala Pro Cys Asn Ala Ala Cys Ser Cys Gln Pro
            500                 505                 510

Glu His Tyr Ser Pro Val Cys Gly Ser Asp Gly Leu Met Tyr Phe Ser
        515                 520                 525

Leu Cys His Ala Gly Cys Pro Ala Ala Thr Glu Thr Asn Val Asp Gly
    530                 535                 540

Gln Lys Val Tyr Arg Asp Cys Ser Cys Ile Pro Gln Asn Leu Ser Ser
545                 550                 555                 560

Gly Phe Gly His Ala Thr Ala Gly Lys Cys Thr Ser Thr Cys Gln Arg
                565                 570                 575

Lys Pro Leu Leu Leu Val Phe Ile Phe Val Ile Phe Phe Thr Phe
            580                 585                 590

Leu Ser Ser Ile Pro Ala Leu Thr Ala Thr Leu Arg Cys Val Arg Asp
    595                 600                 605

Pro Gln Arg Ser Phe Ala Leu Gly Ile Gln Trp Ile Val Arg Ile
610                 615                 620

Leu Gly Gly Ile Pro Gly Pro Ile Ala Phe Gly Trp Val Ile Asp Lys
625                 630                 635                 640

Ala Cys Leu Leu Trp Gln Asp Gln Cys Gly Gln Gln Gly Ser Cys Leu
                645                 650                 655

Val Tyr Gln Asn Ser Ala Met Ser Arg Tyr Ile Leu Ile Met Gly Leu
            660                 665                 670

Leu Tyr Lys Val Leu Gly Val Leu Phe Phe Ala Ile Ala Cys Phe Leu
        675                 680                 685

Tyr Lys Pro Leu Ser Glu Ser Ser Asp Gly Leu Glu Thr Cys Leu Pro
    690                 695                 700

Ser Gln Ser Ser Ala Pro Asp Ser Ala Thr Asp Ser Gln Leu Gln Ser
705                 710                 715                 720

Ser Val

<210> SEQ ID NO 13
<211> LENGTH: 20
<212> TYPE: DNA
<213> ORGANISM: Homo sapiens

<400> SEQUENCE: 13
accctgtcta gcaggttgca                                                20

<210> SEQ ID NO 14
<211> LENGTH: 19
<212> TYPE: DNA
<213> ORGANISM: Homo sapiens

<400> SEQUENCE: 14
ctgtcggagt cttcagatg                                                 19

```
<210> SEQ ID NO 15
<211> LENGTH: 20
<212> TYPE: DNA
<213> ORGANISM: Homo sapiens

<400> SEQUENCE: 15
tccatcacag cctcctacgc                                               20

<210> SEQ ID NO 16
<211> LENGTH: 20
<212> TYPE: DNA
<213> ORGANISM: Homo sapiens

<400> SEQUENCE: 16
tgcctctact ctgaccctag                                               20

<210> SEQ ID NO 17
<211> LENGTH: 20
<212> TYPE: DNA
<213> ORGANISM: Homo sapiens

<400> SEQUENCE: 17
ggagcagtca ttgacaccac                                               20

<210> SEQ ID NO 18
<211> LENGTH: 21
<212> TYPE: DNA
<213> ORGANISM: Homo sapiens

<400> SEQUENCE: 18
tgctgggagt acaacgtgac g                                             21

<210> SEQ ID NO 19
<211> LENGTH: 20
<212> TYPE: DNA
<213> ORGANISM: Homo sapiens

<400> SEQUENCE: 19
acaaggagga tggactgcag                                               20

<210> SEQ ID NO 20
<211> LENGTH: 20
<212> TYPE: DNA
<213> ORGANISM: Homo sapiens

<400> SEQUENCE: 20
caggaatccc agctccagtg                                               20

<210> SEQ ID NO 21
<211> LENGTH: 20
<212> TYPE: DNA
<213> ORGANISM: Homo sapiens

<400> SEQUENCE: 21
gctacaaccc aactactggc                                               20

<210> SEQ ID NO 22
<211> LENGTH: 20
```

-continued

```
<212> TYPE: DNA
<213> ORGANISM: Homo sapiens

<400> SEQUENCE: 22
gggactaact gtgatactgg                                               20
```

ORGANIC ANION TRANSPORT PROTEINS

This application is a Divisional of application Ser. No. 09/575,081, filed May 19, 2000, now U.S. Pat. No. 6,692,934 which claims priority from provisional U.S. application Ser. No. 60/135,081, filed May 20, 1999, the disclosures of which are hereby incorporated herein by reference in their entirety.

FIELD OF THE INVENTION

The invention claims isolated nucleic acid encoding all or a portion of novel members of the organic anion transport protein ("OATP") designated OATP2, OATP-RP1, OATP-RP2, OATP-RP3, OATP-RP4 and OATP-RP5. Also claimed are vectors containing the nucleic acid sequences, host cells containing the vectors and polypeptides having all or part of the amino acid sequence of OATP2, OATP-RP1, OATP-RP2, OATP-RP3, OATP-RP4 and OATP-RP5. Tissue expression of the transporter is described as well as some of its substrates. Also claimed are uses for these novel OATPs, including for targeting drugs to specific tissues, for modulating the concentration of endogenous substrates, and for identifying a substrate capable of being transported by a novel OATP of the invention.

BACKGROUND OF THE INVENTION

The liver functions in the clearance of a large variety of metabolic products, drugs and other xenobiotics by transporting them across the sinusoidal membrane into the hepatocyte. Several classes of transport systems have been described that mediate these processes including the Na+/taurocholate cotransporter polypeptide, NTCP, in rat and human liver (Hagenbuch, B., et al. (1991) *Proc. Natl. Acad. Sci. USA* 88:10629-33; Hagenbuch, B. et al., (1994) *J. Clin. Invest.* 93:1326-31) and a family of organic anion transporting polypeptides (OATPs) that are principally expressed in liver, kidney and brain, and transport a broad spectrum of substrates in a sodium-independent manner (Meier, P. J., et al., (1997) *Hepatology* 26:1667-77; Wolkoff, A. W., (1996) *Semin. Liver Dis.* 16:121-127). The distribution of this latter family of transporters in liver, kidney and choroid plexus in the brain is thought to reflect common physiological requirements of these organs for the clearance of a multitude of organic anions. There are three OATP isoforms in the rat: roatp1 (Jacquemin, E., et al., (1994) *Proc. Natl. Acad. Sci. USA* 91:133-37); roatp2 (Noe, B. A., et al., (1997) *Proc. Natl. Acad. Sci. USA* 94:10346-50; and roatp3 (Abe, T., et al., (1998) *J. Biol. Chem.* 273:11395-401). In addition to bile acids, OATPs are known to transport a variety of other compounds. These include, depending on the transporter, unconjugated and conjugated steroids such as estrone sulfate, estradiol-17B-glucuronide, aldosterone, and cardiac glycosides (Boussuyt, X., et al., (1996) *J. Pharmacol. Exp. Ther.* 276:891-6; Boussuyt, X. (1996) *J. Hepatol.* 25:733-8; Kanai, N., et al., (1996) *Am. J. Physiol.* 270:F319-F325; Kanai, N., et al., (1996) *Am. J. Physiol.* 270:F326-F331; Noe, B. A., et al., (1997) *Proc. Natl. Acad. Sci. USA* 94:10346-50). Bromosulfophthalien (Jacquemin, E., et al., (1994) *Proc. Natl. Acad. Sci. USA* 91:133-7); mycotoxin (Kontaxi, M., et al., (1996) *J. Pharmacol. Exp. Ther.* 279:1507-13); leukotriene $C_4$ (Li, L., et al., (1998) *J. Biol. Chem.* 273:16184-91); and thyroid hormone (Abe, T., et al., (1998) *J. Biol. Chem.* 273:11395) are additional substrates.

Several proteins have been identified. Jacquemin, E., et al., (1994) *Proc. Natl. Acad. Sci. U.S.A.*, 91:133-137 reported the first cloning and identification of a member of the OATP transporter family, namely the rat oatp1. The first cloning and identification of a human OATP was reported in Kullak-Ublick, G. A., et al., (1995) *Gastroenterology*, 109:1274-1282. Its expression was found in liver, kidney brain and other organs. The authors concluded, based on substrate specificities, that it was not the human orthologue of rat oatp 1.

Substrate specificities of rat oatp1 are discussed in Kullak-Ublick, G. A. et al., (1994) *Hepatology*, 20:411-416, while substrate specificities of human OATP are discussed in Bossuyt, X., et al., (1996) *J. Hepatol.*, 25:733-738.

Data was later discovered showing that rat oatp1 is involved in the transport of steroids (Bossuyt, X., et al., (1996) *J. Pharmacol. Exp. Ther.*, 276:891-896), and that human OATP acts as a transporter for the psychoactive hormone DHEAS (Kullak-Ublick, G. A., et al., (1998) *FEBS Lett.*, 424:173-176). For a review of the OATP family and organic anoin transport in the liver, see Wolkoff, A. W., (1996) *Semin. Liver Dis.*, 16:121-127.

A third rat OATP isoform that was shown to transport thyroid hormones T3 and T4 was cloned and reported in Abe, T., et al., (1998) *J. Biol. Chem.*, 273:22395-22401.

All references cited herein, whether supra or infra, are hereby incorporated by reference in their entirety.

SUMMARY OF THE INVENTION

The present invention encompasses novel organic anion transport proteins ("OATP") and polynucleotides encoding said OATPs. The OATPs disclosed herein are designated OATP2, OATP-RP2, OATP-RP3, OATP-RP4, OATP-RP5 and OATP-RP 1. A polynucleotide sequence of each OATP is disclosed herein, along with the deduced amino acid sequence. The cDNAs encoding the OATPs of the present invention have been deposited with the American Type Culture Collection and given Accession Numbers ATCC 207213 (OATP2), ATCC 207212 (OATP-RP2), ATCC 207209 (OATP-RP3), ATCC 207210 (OATP-RP4), ATCC 207211 (OATP-RP5), and ATCC 207214 (OATP-RP1).

The present inventors sequenced the cDNAs encoding the novel OATPs and determined the primary sequence of the deduced proteins. Disclosed herein are the nucleic acid sequence (SEQ ID NO:1) and amino acid sequence (SEQ ID NO:2) of OATP2; the nucleic acid sequence (SEQ ID NO:3) and amino acid sequence (SEQ ID NO:4) of OATP-RP2; the nucleic acid sequence (SEQ ID NO:5) and amino acid sequence (SEQ ID NO:6) of OATP-RP3; the nucleic acid sequence (SEQ ID NO:7) and amino acid sequence (SEQ ID NO:8) of OATP-RP4; the nucleic acid sequence (SEQ ID NO:9) and amino acid sequence (SEQ ID NO:10) of OATP-RP5; and the nucleic acid sequence (SEQ ID NO:11) and amino acid sequence (SEQ ID NO:12) of OATP-RP1.

The OATPs of the present invention can be produced by: (1) inserting the cDNA of a disclosed OATP into an appropriate expression vector; (2) transfecting the expression vector into an appropriate transfection host(s); (3) growing the transfected host(s) in appropriate culture media; and (4) assaying the transport activity in the transfected cells.

The present invention therefore provides a purified and isolated nucleic acid molecule, preferably a DNA molecule, having a sequence which codes for an OATP, or an oligonucleotide fragment of the nucleic acid molecule which is unique to an OATP of the invention. In a preferred embodiment of the invention, the purified and isolated nucleic acid molecule has the sequence as shown in SEQ ID NO:1 (OATP2). In another preferred embodiment, the purified and isolated nucleic acid molecule has the sequence as shown in SEQ ID NO:3 (OATP-RP2). In still another preferred embodiment the purified and isolated nucleic acid molecule has the sequence as shown in SEQ ID NO:5 (OATP-RP3). In still another preferred embodiment of the present invention the purified and isolated nucleic acid molecule has the nucleotide sequence as shown in SEQ ID NO:7 (OATP-RP4). In still another preferred embodiment the purified and isolated nucleic acid molecule has the sequence as shown in SEQ ID NO:9 (OATP-RP5). In still another preferred embodiment of the present invention the purified and isolated nucleic acid molecule has the nucleotide sequence as shown in SEQ ID NO:11 (OATP-RP1).

The invention also contemplates a double stranded nucleic acid molecule comprising a nucleic acid molecule of the invention or an oligonucleotide fragment thereof hydrogen bonded to a complementary nucleotide base sequence.

The terms "isolated and purified nucleic acid", "isolated and purified polynucleotide", "substantially pure nucleic acid", and "substantially pure polynucleotide", e.g., substantially pure DNA, refer to a nucleic acid molecule which is one or both of the following: (1) not immediately contiguous with either one or both of the sequences, e.g., coding sequences, with which it is immediately contiguous (i.e., one at the 5' end and one at the 3'end) in the naturally occurring genome of the organism from which the nucleic acid is derived; or (2) which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure or isolated and purified DNA also includes a recombinant DNA which is part of a hybrid gene encoding additional OATP sequence.

The present invention provides in one embodiment: (a) an isolated and purified nucleic acid molecule comprising a sequence encoding all or a portion of a protein having the amino acid sequence as shown in SEQ ID NO:2 (OATP2); (b) nucleic acid sequences complementary to (a); (c) nucleic acid sequences which exhibit at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The degree of homology (percent sequence identity) between two sequences may be determined, for example, by comparing the two sequences using computer programs commonly employed for this purpose. One suitable program is the GAP computer program described by Devereux et al., (1984) *Nucl. Acids Res.* 12:387. The GAP program utilizes the alignment method of Needleman and Wunsch (1970) *J. Mol. Biol.* 48:433, as revised by Smith and Waterman (1981) *Adv. Appl. Math.* 2:482. Briefly, the GAP program defines percent identity as the number of aligned symbols (i.e., nucleotides or amino acids) which are identical, divided by the total number of symbols in the shorter of the two sequences.

As used herein the term "stringent conditions" encompasses conditions known in the art under which a nucleotide sequence will hybridize to: (a) an isolated and purified nucleic acid molecule comprising a sequence encoding a protein having the amino acid sequence as shown herein, or to (b) a nucleic acid sequence complementary to (a). Screening polynucleotides under stringent conditions may be carried out according to the method described in Nature, 313:402-404 (1985). Polynucleotide sequences capable of hybridizing under stringent conditions with the polynucleotides of the present invention may be, for example, allelic variants of the disclosed DNA sequences, or may be derived from other sources. General techniques of nucleic acid hybridization are disclosed by Sambrook et al., "Molecular Cloning: A Laboratory Manual", 2nd Ed., Cold Spring Harbor Laboratory, Cold Spring Harbor, N.Y. (1984); and by Haymes et al., "Nucleic Acid Hybridization: A Practical Approach", IRL Press, Washington, D.C. (1985), which references are incorporated herein by reference.

The present invention provides in another embodiment: (a) an isolated and purified nucleic acid molecule comprising a sequence encoding all or a portion of a protein having the amino acid sequence as shown in SEQ ID NO:4 (OATP-RP2); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:6 (OATP-RP3); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:8 (OATP-RP4); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:10 (OATP-RP5); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention provides in another embodiment: (a) an isolated and purified nucleic acid molecule comprising a sequence encoding all or a portion of a protein having the amino acid sequence as shown in SEQ ID NO:12 (OATP-RP1); (b) nucleic acid sequences complementary to (a); (c) nucleic acid sequences which are at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention also provides: (a) a purified and isolated nucleic acid molecule comprising a sequence as shown in SEQ ID NO:1 (OATP2); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:3 (OATP-RP2); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:5 (OATP-RP3); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:7 (OATP-RP4); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:9 (OATP-RP5); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention further provides: (a) a purified and isolated nucleic acid molecule comprising a sequence as shown in SEQ ID NO:11 (OATP-RP1); (b) nucleic acid sequences complementary to (a); (c) nucleic acid sequences having at least 80%, more preferably at least 90%, more preferably at least 95%, and most preferably at least 98% sequence identity to (a); or (d) a fragment of (a) or (b) that is at least 18 bases and which will hybridize to (a) or (b) under stringent conditions.

The present invention additionally covers polynucleotides and amino acid sequences of the present invention having one or more structural mutations including replacement, deletion or insertion mutations. For example, a signal peptide may be deleted, or conservative amino acid substitutions may be made to generate a protein that is still biologically competent or active.

The invention further contemplates a recombinant molecule comprising a nucleic acid molecule of the present invention or an oligonucleotide fragment thereof and an expression control sequence operatively linked to the nucleic acid molecule or oligonucleotide fragment. A transformant host cell including a recombinant molecule of the invention is also provided.

In another aspect, the invention features a cell or purified preparation of cells which include a novel gene encoding an OATP of the present invention, or which otherwise misexpresses a gene encoding an OATP of the present invention. The cell preparation can consist of human or non-human cells, e.g., rodent cells, e.g., mouse or rat cells, rabbit cells, non-human primate cells, or pig cells. In preferred embodiments, the cell or cells include an OATP transgene, e.g., a heterologous form of an OATP gene, e.g., a gene derived from humans (in the case of a non-human cell). The OATP transgene can be misexpressed, e.g., overexpressed or underexpressed. In other preferred embodiments, the cell or cells include a gene which misexpresses an endogenous OATP gene, e.g., a gene that expression of which is disrupted, e.g., a knockout. Such cells can serve as a model for studying disorders which are related to mutated or misexpressed OATP alleles for use in drug screening.

Still further, the invention provides plasmids which comprise the nucleic acid molecules of the invention. Also encompassed within the invention are vectors comprising the nucleic acid sequences disclosed herein, as well as host cells comprising said vectors.

The present invention also includes a novel OATP of the present invention, or an active part thereof. A biologically competent or active form of the protein or part thereof is also referred to herein as an "active OATP or part thereof".

The invention further contemplates antibodies having specificity against an epitope of an OATP of the present invention or part of the protein. These antibodies may be polyclonal or monoclonal. The antibodies may be labeled with a detectable substance and they may be used, for example, to detect a novel OATP of the invention in tissue and cells. Additionally, the antibodies of the present invention, or portions thereof, may be used to make targeted antibodies that destroy OATP expressing cells (e.g., antibody-toxin fusion proteins, or radiolabelled antibodies).

The invention also permits the construction of nucleotide probes which encode part or all of a novel OATP protein of the invention or a part of the protein. Thus, the invention also relates to a probe comprising a nucleotide sequence coding for a protein, which displays the properties of a novel OATP of the invention or a peptide unique to the protein. The probe may be labeled, for example, with a detectable (e.g., radioactive) substance and it may be used to select from a mixture of nucleotide sequences a nucleotide sequence coding for a protein which displays the properties of a novel OATP of the invention.

The present invention also provides a transgenic non-human animal (e.g., a rodent, e.g., a mouse or a rat, a rabbit or a pig) or embryo all of whose germ cells and somatic cells contain a recombinant molecule of the invention, preferably a recombinant molecule comprising a nucleic acid molecule of the present invention encoding an OATP of the invention or part thereof. The recombinant molecule may comprise a nucleic acid sequence encoding an OATP of the present invention with a structural mutation, or may comprise a nucleic acid sequence encoding an OATP of the invention or part thereof and one or more regulatory elements which differ from the regulatory elements that drive expression of the native protein. In another preferred embodiment, the animal has an OATP gene which is misexpressed or not expressed, e.g., a knockout. Such transgenic animals can serve as a model for studying disorders that are related to mutated or misexpressed OATPs of the present invention.

The invention still further provides a method for identifying a substance which is capable of binding a novel OATP of the invention, comprising reacting a novel OATP of the invention or part of the protein under conditions which permit the formation of a complex between the substance and a novel OATP protein or part of the protein, and assaying for substance-OATP complexes, for free substance, for non-complexed OATP, or for activation of an OATP.

An embodiment of the invention provides a method for identifying substrates which are capable of binding to a novel OATP protein of the invention, isoforms thereof, or part of the protein, said method comprising reacting a novel OATP protein of the invention, isoforms thereof, or part of the protein, with at least one substrate which potentially is capable of binding to the protein, isoform, or part of the protein, under conditions which permit the formation of substrate-transporter protein complexes, and assaying for substrate-transporter protein complexes, for free substrate, for non-complexed OATP protein, or for activation of an OATP. In a preferred embodiment of the method, substrates are identified which are capable of binding to and being transported by a novel OATP protein of the invention, isoforms thereof, or part of the protein.

The invention also provides methods for screening potentially useful pharmacological agonists or antagonists of the OATPs of the present invention. The method comprises testing potential agents by adding the agent to be tested to a cell expressing a novel OATP of the present invention in the presence of a compound known to be transported by an OATP of the invention, and measuring the augmentation or inhibition of transport of the known compound.

An OATP of the present invention is also useful to identify compounds that may be transported into an organ, e.g., the liver. Compounds that are found to be actively transported into the liver are useful as carriers for other therapeutics targeting the liver.

Also included within the scope of the present invention is a composition which includes an OATP of the present invention, a fragment thereof (or a nucleic acid encoding said OATP or fragment thereof) and one or more additional components, e.g., a carrier, diluent or solvent. The additional component can be one that renders the composition useful for in vitro, in vivo, pharmaceutical or veterinary use.

Encompassed within the present invention are agonists and antagonists of an OATP of the present invention. Pharmacological agonists or antagonists are useful to increase or decrease the flow of compounds transported by an OATP of the present invention. Said agonists and/or antagonists of the present invention are preferably administered with an acceptable carrier, diluent or solvent.

In another aspect, the present invention relates to a method of treating a mammal, e.g., a human, at risk for a disorder, e.g., a disorder characterized by aberrant or unwanted level or biological activity of an OATP of the present invention. Additionally, encompassed within the invention is a method of treating a mammal, e.g., a human, at risk for disorders of the liver. Since OATP2 is expressed exclusively in the liver, compounds that are optimized for OATP2 are useful to target hepatic delivery. These compounds in themselves may be useful therapeutics, or may be useful to chaperone other therapeutic compounds to the liver. In addition, blocking OATP2-compound interactions could provide benefit by decreasing its first-pass extraction by the liver and, thus, increasing plasma concentrations and prolonging the systemic half-life of a drug.

Also within the scope of the present invention are fusion proteins comprising all or a portion of an OATP of the present invention.

The primary object of the present invention is the identification of new human OATPs, as identified by the nucleic acid and amino acid sequences disclosed herein. Additional objects of the invention are the methods of using the cDNA, the OATP proteins, monoclonal antibodies specific for the novel OATPs, fusion proteins comprising a portion of the OATP protein of the present invention, and agonists and/or antagonists of the novel OATPs as described above.

BRIEF DESCRIPTION OF THE FIGURES

FIG. 3 shows a sequence alignment of OATP family members. The protein sequences of human OATP2 (SEQ ID NO:2), OATP-RP1 (SEQ ID NO:12), OATP-RP2 (SEQ ID NO:4), OATP-RP3 (SEQ ID NO:6), OATP-RP4 (SEQ ID NO:8), and OATP-RP5 (SEQ ID NO:10) are aligned with the following other known OATP family members: roatp2 (SEQ ID NO:23), roatp3 (SEQ ID NO:24), rOAT-K1 (SEQ ID NO:25); roatp1 (SEQ ID NO:26); hOATP (SEQ ID NO:27); and hPGT (SEQ ID NO:28). Also shown is a concensus sequence in bold (SEQ ID NO:29). A concensus is indicated if at least 6 out of the 12 sequences are identical at a given position. A residue is capitalized if it agrees with the concensus.

DETAILED DESCRIPTION OF THE INVENTION

Figure 1:
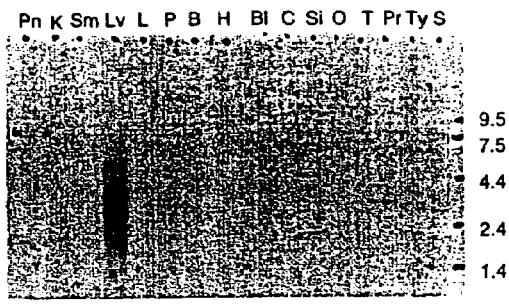
FIG. 1 is a Northern blot showing the mRNA tissue distribution of OATP2, OATP-RP1, OATP-RP2, OATP-RP4, and OATP-RP5. The tissues corresponding to the abbreviations above the lanes are indicated below.
Figure 1:
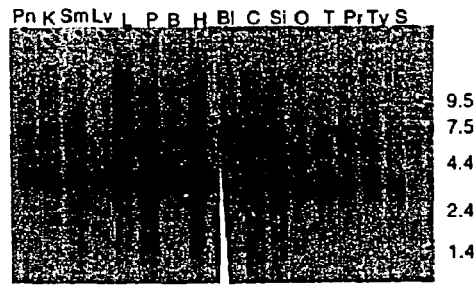
Figure 1:
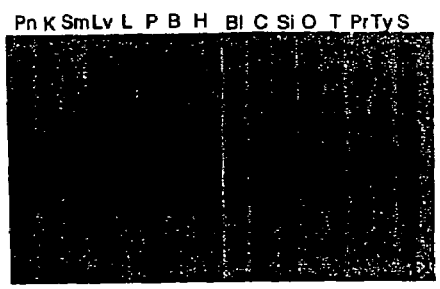
Figure 1:
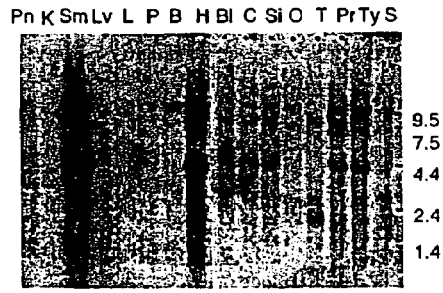
Figure 1:

The following definitions apply to the terms used throughout this specification, unless otherwise defined in specific instances:

"cloning"—isolation of a particular gene from genetic material, for example a genome, genomic library, or cDNA library into a plasmid or other vector;

"coding region"—the region of a nucleic acid sequence that codes for an active protein;

"OATP"—organic anion transport protein;

"stringent conditions" (as used concerning nucleic acid hybridization)—Southern blotting washed in 0.1×SSC and 0.1% SDS at a temperature of at least about 65° C. See Maniatis et al., Molecular Cloning: A Laboratory Manual, Cold Spring Harbor Laboratory, Cold Spring Harbor, N.Y. (1982); one skilled in the relevant art would recognize that less stringent conditions (e.g., 1× or 2×SSC, 0.1% SDS) may be employed in using the novel sequences disclosed herein to identify nucleic acid sequences encoding novel OATPs.

"Northern blotting"—a method of identifying particular RNA fragments by hybridization with a complementary nucleic acid, typically a cDNA or an oligonucleotide;

"open reading frame" or "ORF"—a DNA sequence containing a series of nucleotide triplets coding for amino acids and lacking any termination codes;

"plasmid"—cytoplasmic, autonomously replicating DNA elements found in microorganisms;

"promoter"—a region on DNA at which RNA polymerase binds and initiates transcription; and "Southern blotting"—a method of identifying particular DNA fragments by hybridization with a complementary nucleic acid, typically a cDNA or an oligonucleotide;

"transport"—the movement of a substance across a biological membrane as determined by measuring the redistribution of such a substance across the membrane upon exposure to a transporter.

For definitions of other terms in this specification, see F. Sherman et al., *Laboratory Course Manual for Methods in Yeast Genetics*, Cold Spring Harbor Laboratory, Cold Spring Harbor, N.Y. (1987) and Lewin, B., *Genes IV*, Oxford University Press, Oxford (1990). For the definitions of abbreviations, see *Aldrichimica Acta*, Vol. 17, No. 1 (1984).

Use and Utility

The amino acid sequences of the novel organic anion transport proteins of the present invention are aligned with known transporters of this family in FIG. 3. The degree of sequence homology between the sequences of the present invention and known organic anion transporters indicates that the proteins of the present invention are organic anion transporters.

It is believed by those skilled in the art that OATP proteins may be involved in the transport of compounds into the liver. Persons of ordinary skill in the art can use the OATP proteins of the present invention to assay for agents that may increase or decrease the rate of transport of compounds into the liver, or for compounds that are transported by the OATPs of the present invention that are useful as carriers for other compounds that are desired to be carried to a specific organ (e.g., the liver).

Therefore, agents that increase or decrease the rate of substrate transport by the OATPs of the present invention, or agents identified as carriers, are useful in the treatment of liver disease.

Because some of the OATPs of the present invention are organ specific/selective (e.g., OATP2—liver; OATP-RP4—heart and skeletal muscle, and OATP-RP5—brain and testis), compound specificity is built into any specific substrate of these OATPs and into molecular carriers transported by these OATPs. An agent transported by the above OATPs of the present invention would thus be delivered to the tissues in which they are expressed and not to tissues lacking the above OATPs, thereby achieving tissue specific targeting.

The OATP nucleic acids of the present invention, or antisense nucleic acids, may be useful therapeutic or diagnostic agents. For such gene therapy, the nucleic acids may be incorporated into vectors and/or formulated as described below and in further detail in the art.

The present invention also provides a basis for diagnostic genetic screens for predicting response to drugs. At least one of the transporters disclosed and claimed herein is a transporter of a known drug (i.e., OATP2 transports pravastatin into hepatocytes). Other transporters disclosed herein may similarly transport additional drugs into tissues. Persons skilled in the art can: (1) screen the transporter genes for allelic variants (genotypes) in the general population by various sequencing methods; and (2) determine the association of these transporter genotypes in patients with response to the transported drug in clinical trials. Particular allelic variants may be more or less effective in transporting a drug, which would be related to drug efficacy. Thus, genotyping of the claimed transporters could form the basis of a clinical diagnostic test to predict a patient's response to drug therapy.

Persons skilled in the art can use the polypeptides and nucleic acids of this invention to prepare vectors, cells or cell lines, and antibodies. All of these are useful in assays for identification of OATP positive and negative modulators (i.e., agonists and/or antagonists) and OATP carriers. The term "positive modulator" as used herein refers to an agent or compound that increases the rate or amount of transport of a compound into an organ, e.g., the liver, or an agent or compound that decreases the rate or amount of transport of a compound into an organ. The term "negative modulator" refers to a compound that is joined to a second compound to prevent the second compounds transport into or out of cells. The term "carrier" as used herein refers to an agent or compound that is transported by an OATP of the present invention and that is capable of being joined to or associated with another compound to chaperone that other compound into an organ, e.g., the liver. A carrier includes an agent that is used to transport a compound into an organ that is otherwise not transported into said organ, and includes an agent that increases the transport of a compound into an organ that is capable of being transported by an OATP.

One can administer OATP modulators and carriers to various mammalian species, such as monkeys, dogs, cats, mice, rats, humans, etc. By known methods, persons skilled in the pharmaceutical art can incorporate OATP modulators and carriers in a conventional systemic dosage form, such as a tablet, capsule, elixir or injectable formulation. The above dosage forms will also include any necessary physiologically acceptable carrier material, excipient, lubricant, buffer, antibacterial, bulking agent (such as mannitol), anti-oxidants (ascorbic acid or sodium bisulfite) or the like.

Process of preparation

In general

This specification describes the cloning and functional expression of full-length human cDNA clones of OATPs, preferably the nucleic acid sequence of OATP2 (SEQ ID NO:1), the amino acid sequence of OATP2 (SEQ ID NO:2), the nucleic acid sequence of OATP-RP2 (SEQ ID NO:3), the amino acid sequence of OATP-RP2 (SEQ ID NO:4), the nucleic acid sequence of OATP-RP3 (SEQ ID NO:5), the amino acid sequence of OATP-RP3 (SEQ ID NO:6), the nucleic acid sequence of OATP-RP4 (SEQ ID NO:7), the amino acid sequence of OATP-RP4 (SEQ ID NO:8), the nucleic acid sequence of OATP-RP5 (SEQ ID NO:9), the amino acid sequence of OATP-RP5 (SEQ ID NO:10), the nucleic acid sequence of OATP-RP1 (SEQ ID NO:11), and the amino acid sequence of OATP-RP1 (SEQ ID NO:12).

DNA clones comprising nucleotide sequences encoding the OATPs described above were deposited with the American Type Culture Collection ("ATCC") (10801 University Blvd., Manassas, Va. 20110-2209) on Apr. 20, 1999, and given the following ATCC Accession Numbers: 207209 (OATP-RP3), 207210 (OATP-RP4), 207211 (OATP-RP5), 207212 (OATP-RP2), 207213 (OATP2), and 207214 (OATP-RP1). The deposit(s) referred to herein will be maintained under the terms of the Budapest Treaty on the International Recognition of the Deposit of Microorganisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the of the polypeptides encoded thereby, are incorporated herein by reference and are controlling in the event of any conflict with any description of sequences herein. A license may be required to make, use or sell the deposited materials, and no such license is hereby granted.

Nucleic Acids

With the disclosed OATP gene sequences in hand, one skilled in the art can obtain OATP nucleic acids of this invention by known methods. Such methods include: (1) Southern and Northern blotting; (2) Western immunoblotting; (3) chemical synthesis; (4) synthesis by polymerase chain reaction (PCR) from primers; (5) expression cloning; and (6) subtractive cDNA cloning.

Preferred nucleic acid sequences of the present invention include the following (preferably the coding sequences as shown below):

```
OATP2 (SEQ ID NOS: 1 and 2):
CGGACGCGTG GGCGGACGCG TGGGTCGCCC ACGCGTCCGA CTTGTTGCAG      50

TTGCTGTAGG ATTCTAAATC CAGGTGATTG TTTCAAACTG AGCATCAACA     100

ACAAAAACAT TTGTATGATA TCTATATTTC AATC ATG GAC CAA AAT CAA  149
                                      M   D   Q   N   Q

CAT TTG AAT AAA ACA GCA GAG GCA CAA CCT TCA GAG AAT AAG    191
 H   L   N   K   T   A   E   A   Q   P   S   E   N   K

AAA ACA AGA TAC TGC AAT GGA TTG AAG ATG TTC TTG GCA GCT    233
 K   T   R   Y   C   N   G   L   K   M   F   L   A   A

CTG TCA CTC AGC TTT ATT GCT AAG ACA CTA GGT GCA ATT ATT    275
 L   S   L   S   F   I   A   K   T   L   G   A   I   I

ATG AAA AGT TCC ATC ATT CAT ATA GAA CGG AGA TTT GAG ATA    317
 M   K   S   S   I   I   H   I   E   R   R   F   E   I

TCC TCT TCT CTT GTT GGT TTT ATT GAC GGA AGC TTT GAA ATT    359
 S   S   S   L   V   G   F   I   D   G   S   F   E   I

GGA AAT TTG CTT GTG ATT GTA TTT GTG AGT TAC TTT GGA TCC    401
 G   N   L   L   V   I   V   F   V   S   Y   F   G   S

AAA CTA CAT AGA CCA AAG TTA ATT GGA ATC GGT TGT TTC ATT    443
 K   L   H   R   P   K   L   I   G   I   G   C   F   I

ATG GGA ATT GGA GGT GTT TTG ACT GCT TTG CCA CAT TTC TTC    485
 M   G   I   G   G   V   L   T   A   L   P   H   F   F

ATG GGA TAT TAC AGG TAT TCT AAA GAA ACT AAT ATC GAT TCA    527
 M   G   Y   Y   R   Y   S   K   E   T   N   I   D   S

TCA GAA AAT TCA ACA TCG ACC TTA TCC ACT TGT TTA ATT AAT    569
 S   E   N   S   T   S   T   L   S   T   C   L   I   N

CAA ATT TTA TCA CTC AAT AGA GCA TCA CCT GAG ATA GTG GGA    611
 Q   I   L   S   L   N   R   A   S   P   E   I   V   G

AAA GGT TGT TTA AAG GAA TCT GGG TCA TAC ATG TGG ATA TAT    653
 K   G   C   L   K   E   S   G   S   Y   M   W   I   Y

GTG TTC ATG GGT AAT ATG CTT CGT GGA ATA GGG GAG ACT CCC    695
 V   F   M   G   N   M   L   R   G   I   G   E   T   P

ATA GTA CCA TTG GGG CTT TCT TAC ATT GAT GAT TTC GCT AAA    737
 I   V   P   L   G   L   S   Y   I   D   D   F   A   K

GAA GGA CAT TCT TCT TTG TAT TTA GGT ATA TTG AAT GCA ATA    779
 E   G   H   S   S   L   Y   L   G   I   L   N   A   I

GCA ATG ATT GGT CCA ATC ATT GGC TTT ACC CTG GGA TCT CTG    821
 A   M   I   G   P   I   I   G   F   T   L   G   S   L

TTT TCT AAA ATG TAC GTG GAT ATT GGA TAT GTA GAT CTA AGC    863
 F   S   K   M   Y   V   D   I   G   Y   V   D   L   S

ACT ATC AGG ATA ACT CCT ACT GAT TCT CGA TGG GTT GGA GCT    905
 T   I   R   I   T   P   T   D   S   R   W   V   G   A

TGG TGG CTT AAT TTC CTT GTG TCT GGA CTA TTC TCC ATT ATT    947
 W   W   L   N   F   L   V   S   G   L   F   S   I   I

TCT TCC ATA CCA TTC TTT TTC TTG CCC CAA ACT CCA AAT AAA    989
 S   S   I   P   F   F   F   L   P   Q   T   P   N   K

CCA CAA AAA GAA AGA AAA GCT TCA CTG TCT TTG CAT GTG CTG   1031
 P   Q   K   E   R   K   A   S   L   S   L   H   V   L
```

-continued

```
GAA ACA AAT GAT GAA AAG GAT CAA ACA GCT AAT TTG ACC AAT        1073
 E   T   N   D   E   K   D   Q   T   A   N   L   T   N

CAA GGA AAA AAT ATT ACC AAA AAT GTG ACT GGT TTT TTC CAG        1115
 Q   G   K   N   I   T   K   N   V   T   G   F   F   Q

TCT TTT AAA AGC ATC CTT ACT AAT CCC CTG TAT GTT ATG TTT        1157
 S   F   K   S   I   L   T   N   P   L   Y   V   M   F

GTG CTT TTG ACG TTG TTA CAA GTA AGC AGC TAT ATT GGT GCT        1199
 V   L   L   T   L   L   Q   V   S   S   Y   I   G   A

TTT ACT TAT GTC TTC AAA TAC GTA GAG CAA CAG TAT GGT CAG        1241
 F   T   Y   V   F   K   Y   V   E   Q   Q   Y   G   Q

CCT TCA TCT AAG GCT AAC ATC TTA TTG GGA GTC ATA ACC ATA        1283
 P   S   S   K   A   N   I   L   L   G   V   I   T   I

CCT ATT TTT GCA AGT GGA ATG TTT TTA GGA GGA TAT ATC ATT        1325
 P   I   F   A   S   G   M   F   L   G   G   Y   I   I

AAA AAA TTC AAA CTG AAC ACC GTT GGA ATT GCC AAA TTC TCA        1367
 K   K   F   K   L   N   T   V   G   I   A   K   F   S

TGT TTT ACT GCT GTG ATG TCA TTG TCC TTT TAC CTA TTA TAT        1409
 C   F   T   A   V   M   S   L   S   F   Y   L   L   Y

TTT TTC ATA CTC TGT GAA AAC AAA TCA GTT GCC GGA CTA ACC        1451
 F   F   I   L   C   E   N   K   S   V   A   G   L   T

ATG ACC TAT GAT GGA AAT AAT CCA GTG ACA TCT CAT AGA GAT        1493
 M   T   Y   D   G   N   N   P   V   T   S   H   R   D

GTA CCA CTT TCT TAT TGC AAC TCA GAC TGC AAT TGT GAT GAA        1535
 V   P   L   S   Y   C   N   S   D   C   N   C   D   E

AGT CAA TGG GAA CCA GTC TGT GGA AAC AAT GGA ATA ACT TAC        1577
 S   Q   W   E   P   V   C   G   N   N   G   I   T   Y

ATC TCA CCC TGT CTA GCA GGT TGC AAA TCT TCA AGT GGC AAT        1619
 I   S   P   C   L   A   G   C   K   S   S   S   G   N

AAA AAG CCT ATA GTG TTT TAC AAC TGC AGT TGT TTG GAA GTA        1661
 K   K   P   I   V   F   Y   N   C   S   C   L   E   V

ACT GGT CTC CAG AAC AGA AAT TAC TCA GCC CAT TTG GGT GAA        1703
 T   G   L   Q   N   R   N   Y   S   A   H   L   G   E

TGC CCA AGA GAT GAT GCT TGT ACA AGG AAA TTT TAC TTT TTT        1745
 C   P   R   D   D   A   C   T   R   K   F   Y   F   F

GTT GCA ATA CAA GTC TTG AAT TTA TTT TTC TCT GCA CTT GGA        1787
 V   A   I   Q   V   L   N   L   F   F   S   A   L   G

GGC ACC TCA CAT GTC ATG CTG ATT GTT AAA ATT GTT CAA CCT        1829
 G   T   S   H   V   M   L   I   V   K   I   V   Q   P

GAA TTG AAA TCA CTT GCA CTG GGT TTC CAC TCA ATG GTT ATA        1871
 E   L   K   S   L   A   L   G   F   H   S   M   V   I

CGA GCA CTA GGA GGA ATT CTA GCT CCA ATA TAT TTT GGG GCT        1913
 R   A   L   G   G   I   L   A   P   I   Y   F   G   A

CTG ATT GAT ACA ACG TGT ATA AAG TGG TCC ACC AAC AAC TGT        1955
 L   I   D   T   T   C   I   K   W   S   T   N   N   C

GGC ACA CGT GGG TCA TGT AGG ACA TAT AAT TCC ACA TCA TTT        1997
 G   T   R   G   S   C   R   T   Y   N   S   T   S   F

TCA AGG GTC TAC TTG GGC TTG TCT TCA ATG TTA AGA GTC TCA        2039
 S   R   V   Y   L   G   L   S   S   M   L   R   V   S

TCA CTT GTT TTA TAT ATT ATA TTA ATT TAT GCC ATG AAG AAA        2081
 S   L   V   L   Y   I   I   L   I   Y   A   M   K   K

AAA TAT CAA GAG AAA GAT ATC AAT GCA TCA GAA AAT GGA AGT        2123
 K   Y   Q   E   K   D   I   N   A   S   E   N   G   S

GTC ATG GAT GAA GCA AAC TTA GAA TCC TTA AAT AAA AAT AAA        2165
 V   M   D   E   A   N   L   E   S   L   N   K   N   K
```

```
CAT TTT GTC CCT TCT GCT GGG GCA GAT AGT GAA ACA CAT TGT    2207
 H   F   V   P   S   A   G   A   D   S   E   T   H   C

TAA GGGGAGAAAA AAAGCCACTT CTGCTTCTGT GTTTCCAAAC AGCATTGCAT  2260
 *

TGATTCAGTA AGATGTTATT TTTGAGGAGT TCCTGGTCCT TTCACTAAGA     2310

ATTTCCACAT CTTTTATGGT GGAAGTATAA ATAAGCCTAT GAACTTATAA     2360

TAAAACAAAC TGTAGGTAGA AAAAATGAGA GTACTCATTG TTACATTATA     2410

GCTACATATT TGTGGTTAAG GTTAGACTAT ATGATCCATA CAAATTAAAG     2460

TGAGAGACAT GGTTACTGTG TAATAAAAGA AAAAATACTT GTTCAGGTAA     2510

TTCTAATTCT TAATAAAACA AATGAGTATC ATACAGGTAG AGGTTAAAAA     2560

GGAGGAGCTA GATTCATATC CTAAGTAAAG AGAAATGCCT AGTGTCTATT     2610

TTATTAAACA AACAAACACA GAGTTTGAAC TATAATACTA AGGCCTGAAG     2660

TCTAGCTTGG ATATATGCTA CAATAATATC TGTTACTCAC ATAAAATTAT     2710

ATATTTCACA GACTTTATCA ATGTATAATT AACAATTATC TTGTTTAAGT     2760

AAATTTAGAA TACATTTAAG TATTGTGGAA GAAATAAAGA CATTCCAATA     2810

TTTGCAAAAA AAAAAAAAA                                      2830

OATP-RP2 (SEQ ID NOS: 3 and 4):
CCCGGGTCGA CCCACGCGTC CGGGATAAAG TACTCCCAGG AAGGCTTTGA     50

GCCTTGGCAG AAGAGGCTGG GATTGAAGCT TCAGGGAGAG CCAGAGGTGA     100

GGCTGGAGTG GGAGATCACC TGAGGCAGGG CCAGCGGGTG AGGTACCCCA     150

GGTACCAGAC AAGGAAACCA AAGCCACA ATG GGC ACA GAA AAC ACA CCT  199
                                M   G   T   E   N   T   P

GGA GGC AAA GCC AGC CCA GAC CCT CAG GAC GTG CGG CCA AGT    241
 G   G   K   A   S   P   D   P   Q   D   V   R   P   S

GTG TTC CAT AAC ATC AAG CTG TTC GTT CTG TGC CAC AGC CTG    283
 V   F   H   N   I   K   L   F   V   L   C   H   S   L

CTG CAG CTG GCG CAG CTC ATG ATC TCC GGC TAC CTA AAG AGC    325
 L   Q   L   A   Q   L   M   I   S   G   Y   L   K   S

TCC ATC TCC ACA GTG GAG AAG CGC TTC GGC CTC TCC AGC CAG    367
 S   I   S   T   V   E   K   R   F   G   L   S   S   Q

ACG TCG GGG CTG CTG GCC TCC TTC AAC GAG GTG GGG AAC ACA    409
 T   S   G   L   L   A   S   F   N   E   V   G   N   T

GCC TTG ATT GTG TTT GTG AGC TAT TTT GGC AGC CGG GTG CAC    451
 A   L   I   V   F   V   S   Y   F   G   S   R   V   H

CGA CCC CGA ATG ATT GGC TAT GGG GCT ATC CTT GTG GCC CTG    493
 R   P   R   M   I   G   Y   G   A   I   L   V   A   L

GCG GGC CTG CTC ATG ACT CTC CCG CAC TTC ATC TCG GAG CCA    535
 A   G   L   L   M   T   L   P   H   F   I   S   E   P

TAC CGC TAC GAC AAC ACC AGC CCT GAG GAT ATG CCA CAG GAC    577
 Y   R   Y   D   N   T   S   P   E   D   M   P   Q   D

TTC AAG GCT TCC CTG TGC CTG CCC ACA ACC TCG GCC CCA GCC    619
 F   K   A   S   L   C   L   P   T   T   S   A   P   A

TCG GCC CCC TCC AAT GGC AAC TGC TCA AGC TAC ACA GAA ACC    661
 S   A   P   S   N   G   N   C   S   S   Y   T   E   T

CAG CAT CTG AGT GTG GTG GGG ATC ATG TTC GTG GCA CAG ACC    703
 Q   H   L   S   V   V   G   I   M   F   V   A   Q   T

CTG CTG GGC GTG GGC GGG GTG CCC ATT CAG CCC TTT GGC ATC    745
 L   L   G   V   G   G   V   P   I   Q   P   F   G   I
```

-continued

```
TCC TAC ATC GTT GAC TTT GCC CAC AAC AGT AAC TCG CCC CTC      787
 S   Y   I   V   D   F   A   H   N   S   N   S   P   L

TAC CTC GGG ATC CTG TTT GCA GTG ACC ATG ATG GGG CCA GGC      829
 Y   L   G   I   L   F   A   V   T   M   M   G   P   G

CTG GCC TTT GGG CTG GGC AGC CTC ATG CTG CGC CTT TAT GTG      871
 L   A   F   G   L   G   S   L   M   L   R   L   Y   V

GAC ATT AAC CAG ATG CCA GAA GGT GGT ATC AGC CTG ACC ATA      913
 D   I   N   Q   M   P   E   G   G   I   S   L   T   I

AAG GAC CCC CGA TGG GTG GGT GCC TGG TGG CTG GGT TTC CTC      955
 K   D   P   R   W   V   G   A   W   W   L   G   F   L

ATC GCT GCC GGT GCA GTG GCC CTG GCT GCC ATC CCC TAC TTC      997
 I   A   A   G   A   V   A   L   A   A   I   P   Y   F

TTC TTC CCC AAG GAA ATG CCC AAG GAA AAA CGT GAG CTT CAG     1039
 F   F   P   K   E   M   P   K   E   K   R   E   L   Q

TTT CGG CGA AAG GTC TTA GCA GTC ACA GAC TCA CCT GCC AGG     1081
 F   R   R   K   V   L   A   V   T   D   S   P   A   R

AAG GGC AAG GAC TCT CCC TCT AAG CAG AGC CCT GGG GAG TCC     1123
 K   G   K   D   S   P   S   K   Q   S   P   G   E   S

ACG AAG AAG CAG GAT GGC CTA GTC CAG ATT GCA CCA AAC CTG     1165
 T   K   K   Q   D   G   L   V   Q   I   A   P   N   L

ACT GTG ATC CAG TTC ATT AAA GTC TTC CCC AGG GTG CTG CTG     1207
 T   V   I   Q   F   I   K   V   F   P   R   V   L   L

CAG ACC CTA CGC CAC CCC ATC TTC CTG CTG GTG GTC CTG TCC     1249
 Q   T   L   R   H   P   I   F   L   L   V   V   L   S

CAG GTA TGC TTG TCA TCC ATG GCT GCG GGC ATG GCC ACC TTC     1291
 Q   V   C   L   S   S   M   A   A   G   M   A   T   F

CTG CCC AAG TTC CTG GAG CGC CAG TTT TCC ATC ACA GCC TCC     1333
 L   P   K   F   L   E   R   Q   F   S   I   T   A   S

TAC GCC AAC CTG CTC ATC GGC TGC CTC TCC TTC CCT TCG GTC     1375
 Y   A   N   L   L   I   G   C   L   S   F   P   S   V

ATC GTG GGC ATC GTG GTG GGT GGC GTC CTG GTC AAG CGG CTC     1417
 I   V   G   I   V   V   G   G   V   L   V   K   R   L

CAC CTG GGC CCT GTG GGA TGC GGT GCC CTT TGC CTG CTG GGG     1459
 H   L   G   P   V   G   C   G   A   L   C   L   L   G

ATG CTG CTG TGC CTC TTC TTC AGC CTG CCG CTC TTC TTT ATC     1501
 M   L   L   C   L   F   F   S   L   P   L   F   F   I

GGC TGC TCC AGC CAC CAG ATT GCG GGC ATC ACA CAC CAG ACC     1543
 G   C   S   S   H   Q   I   A   G   I   T   H   Q   T

AGT GCC CAC CCT GGG CTG GAG CTG TCT CCA AGC TGC ATG GAG     1585
 S   A   H   P   G   L   E   L   S   P   S   C   M   E

GCC TGC TCC TGC CCA TTG GAC GGC TTT AAC CCT GTC TGC GAC     1627
 A   C   S   C   P   L   D   G   F   N   P   V   C   D

CCC AGC ACT CGT GTG GAA TAC ATC ACA CCC TGC CAC GCA GGC     1669
 P   S   T   R   V   E   Y   I   T   P   C   H   A   G

TGC TCA AGC TGG GTG GTC CAG GAT GCT CTG GAC AAC AGC CAG     1711
 C   S   S   W   V   V   Q   D   A   L   D   N   S   Q

GTT TTC TAC ACC AAC TGC AGC TGC GTG GTG GAG GGC AAC CCC     1753
 V   F   Y   T   N   C   S   C   V   V   E   G   N   P

GTG CTG GCA GGA TCC TGC GAC TCA ACG TGC AGC CAT CTG GTG     1795
 V   L   A   G   S   C   D   S   T   C   S   H   L   V

GTG CCC TTC CTG CTC CTG GTC AGC CTG GGC TCG GCC CTG GCC     1837
 V   P   F   L   L   L   V   S   L   G   S   A   L   A

TGT CTC ACC CAC ACA CCC TCC TTC ATG CTC ATC CTA AGA GGA     1879
 C   L   T   H   T   P   S   F   M   L   I   L   R   G
```

-continued

```
GTG AAG AAA GAA GAC AAG ACT TTG GCT GTG GGC ATC CAG TTC    1921
 V   K   K   E   D   K   T   L   A   V   G   I   Q   F

ATG TTC CTG AGG ATT TTG GCC TGG ATG CCC AGC CCC GTG ATC    1963
 M   F   L   R   I   L   A   W   M   P   S   P   V   I

CAC GGC AGC GCC ATC GAC ACC ACC TGT GTG CAC TGG GCC CTG    2005
 H   G   S   A   I   D   T   T   C   V   H   W   A   L

AGC TGT GGG CGT CGA GCT GTC TGT CGC TAC TAC AAT AAT GAC    2047
 S   C   G   R   R   A   V   C   R   Y   Y   N   N   D

CTG CTC CGA AAC CGG TTC ATC GGC CTC CAG TTC TTC TTC AAA    2089
 L   L   R   N   R   F   I   G   L   Q   F   F   F   K

ACA GGT TCT GTG ATC TGC TTC GCC TTA GTT TTG GCT GTC CTG    2131
 T   G   S   V   I   C   F   A   L   V   L   A   V   L

AGG CAG CAG GAC AAA GAG GCA AGG ACC AAA GAG AGC AGA TCC    2173
 R   Q   Q   D   K   E   A   R   T   K   E   S   R   S

AGC CCT GCC GTA GAG CAG CAA TTG CTA GTG TCG GGC CCA GGG    2215
 S   P   A   V   E   Q   Q   L   L   V   S   G   P   G

AAG AAG CCA GAG GAT TCC CGA GTG TGA GCTGTCTTGG GGCCCCACCT  2262
 K   K   P   E   D   S   R   V   *

GGCCAAGAGT AGCAGCCACA GCAGTACCTC CTCTGAGTCC TTTGCCCAAG     2312

ATTGGGTGTC AAGAGCCCTG TGTTCCATTC TGGCTCCTCC ACTAAATTGC     2362

TGTGTGACTT CAGGCAAAAA AAAAAAAAAA AAAAAAAAAA AAAAAAAAAA     2412

AAAAAAAAAA AAAAAAAAAA AAAAAAAAAA                          2442

OATP-RP3 (SEQ ID NOS: 5 and 6):
                                                CC CACGCGTCCG   12

GCGAGGAGCT GTGCCTTCCA CCTCTCCAGC CCCGGCAGGA CGGGGGCGGC       62

CGCCGCGAAC CCGGGGCGGG GACAGCACGC AGCCTCGAGG CGCGCACCCC      112

CGCCCGGCAG CGGCCCCGAC ACCCGGGGCG AGCGGGAAAG CGGCAGCGGC      162

GGCGGCGGCG GCGGCGGCGG GGGAAGG ATG CAG GGG AAG AAG CCG GGC   210
                                M   Q   G   K   K   P   G

GGT TCG TCG GGC GGC GGC CGG AGC GGC GAG CTG CAG GGG GAC     252
 G   S   S   G   G   G   R   S   G   E   L   Q   G   D

GAG GCG CAG AGG AAC AAG AAA AAG AAA AAG AAG GTG TCC TGC     294
 E   A   Q   R   N   K   K   K   K   K   K   V   S   C

TTT TCC AAC ATC AAG ATC TTC CTG GTG TCC GAG TGC GCC CTG     336
 F   S   N   I   K   I   F   L   V   S   E   C   A   L

ATG CTG GCG CAG GGC ACG GTG GGC GCC TAC CTG GTG AGC GTC     378
 M   L   A   Q   G   T   V   G   A   Y   L   V   S   V

CTG ACC ACC CTG GAG CGT AGG TTC AAC CTG CAG AGC GCT GAC     420
 L   T   T   L   E   R   R   F   N   L   Q   S   A   D

GTG GGT GTG ATC GCT AGC AGC TTC GAG ATC GGG AAC CTG GCG     462
 V   G   V   I   A   S   S   F   E   I   G   N   L   A

CTC ATC CTC TTC GTG AGC TAC TTC GGG GCA CGC GGG CAC CGG     504
 L   I   L   F   V   S   Y   F   G   A   R   G   H   R

CCG CGC CTG ATC GGC TGC GGC GGC ATC GTC ATG GCG CTG GGC     546
 P   R   L   I   G   C   G   G   I   V   M   A   L   G

GCG CTG CTG TCG GCG CTG CCC GAG TTC CTG ACC CAC CAG TAC     588
 A   L   L   S   A   L   P   E   F   L   T   H   Q   Y

AAG TAC GAG GCG GGC GAG ATC CGC TGG GGC GCC GAG GGC CGC     630
 K   Y   E   A   G   E   I   R   W   G   A   E   G   R

GAC GTC TGC GCA GCC AAC GGC TCG GGC GGC GAC GAG GGG CCC     672
 D   V   C   A   A   N   G   S   G   G   D   E   G   P
```

```
GAC CCC GAC CTC ATC TGC CGC AAC CGG ACG GCT ACC AAC ATG      714
 D   P   D   L   I   C   R   N   R   T   A   T   N   M

ATG TAC TTG CTG CTC ATT GGG GCC CAG GTG CTC CTG GGC ATC      756
 M   Y   L   L   L   I   G   A   Q   V   L   L   G   I

GGT GCT ACC CCT GTG CAG CCC CTG GGC GTC TCC TAC ATC GAC      798
 G   A   T   P   V   Q   P   L   G   V   S   Y   I   D

GAC CAC GTG CGG AGG AAG GAC TCC TCG CTC TAT ATA GGA ATC      840
 D   H   V   R   R   K   D   S   S   L   Y   I   G   I

CTG TTC ACG ATG CTG GTA TTT GGA CCA GCC TGC GGG TTT ATC      882
 L   F   T   M   L   V   F   G   P   A   C   G   F   I

CTG GGC TCT TTC TGT ACC AAA ATC TAC GTG GAT GCG GTC TTC      924
 L   G   S   F   C   T   K   I   Y   V   D   A   V   F

ATT GAC ACA AGT AAC CTG GAC ATC ACT CCG GAC GAC CCC CGC      966
 I   D   T   S   N   L   D   I   T   P   D   D   P   R

TGG ATC GGA GCC TGG TGG GGT GGC TTT CTG CTC TGC GGT GCC     1008
 W   I   G   A   W   W   G   G   F   L   L   C   G   A

TTA CTC TTC TTC TCT TCC CTC TTG ATG TTT GGG TTT CCA CAG     1050
 L   L   F   F   S   S   L   L   M   F   G   F   P   Q

TCC CTG CCC CCG CAC TCA GAC CCC GCC ATG GAA AGC GAG CAG     1092
 S   L   P   P   H   S   D   P   A   M   E   S   E   Q

GCC ATG CTC TCC GAA AGA GAA TAC GAG AGA CCC AAG CCC AGC     1134
 A   M   L   S   E   R   E   Y   E   R   P   K   P   S

AAC GGG GTC CTG AGG CAC CCC CTG GAG CCA GAC AGC AGT GCC     1176
 N   G   V   L   R   H   P   L   E   P   D   S   S   A

TCC TGT TTC CAG CAG CTG AGA GTG ATC CCG AAG GTC ACC AAG     1218
 S   C   F   Q   Q   L   R   V   I   P   K   V   T   K

CAC CTG CTC TCA AAC CCT GTG TTC ACC TGC ATC ATC CTG GCC     1260
 H   L   L   S   N   P   V   F   T   C   I   I   L   A

GCC TGC ATG GAG ATT GCA GTG GTG GCT GGC TTC GCT GCC TTT     1302
 A   C   M   E   I   A   V   V   A   G   F   A   A   F

TTG GGG AAG TAC CTG GAG CAG CAG TTT AAC CTC ACC ACC TCT     1344
 L   G   K   Y   L   E   Q   Q   F   N   L   T   T   S

TCT GCC AAC CAG CTG CTT GGG ATG ACT GCG ATC CCG TGT GCT     1386
 S   A   N   Q   L   L   G   M   T   A   I   P   C   A

TGT CTG GGT ATC TTC CTG GGA GGT CTT TTG GTG AAG AAG CTC     1428
 C   L   G   I   F   L   G   G   L   L   V   K   K   L

AGC CTG TCT GCC CTG GGG GCC ATT CGG ATG GCC ATG CTC GTC     1470
 S   L   S   A   L   G   A   I   R   M   A   M   L   V

AAC CTG GTG TCC ACT GCT TGC TAC GTC TCC TTC CTC TTC CTG     1512
 N   L   V   S   T   A   C   Y   V   S   F   L   F   L

GGC TGC GAC ACT GGC CCT GTG GCT GGG GTT ACT GTT CCC TAT     1554
 G   C   D   T   G   P   V   A   G   V   T   V   P   Y

GGA AAC AGC ACA GCA CCT GGC TCA GCC CTG GAC CCC TAC TCG     1596
 G   N   S   T   A   P   G   S   A   L   D   P   Y   S

CCC TGC AAT AAT AAC TGT GAA TGC CAA ACC GAT TCC TTC ACT     1638
 P   C   N   N   N   C   E   C   Q   T   D   S   F   T

CCA GTG TGT GGG GCA GAT GGC ATC ACC TAC CTG TCT GCC TGC     1680
 P   V   C   G   A   D   G   I   T   Y   L   S   A   C

TTT GCT GGC TGC AAC AGC ACG AAT CTC ACG GGC TGT GCG TGC     1722
 F   A   G   C   N   S   T   N   L   T   G   C   A   C

CTC ACC ACC GTC CCT GCT GAG AAC GCA ACC GTG GTT CCT GGA     1764
 L   T   T   V   P   A   E   N   A   T   V   V   P   G

AAA TGC CCC AGT CCT GGG TGC CAA GAG GCC TTC CTC ACT TTC     1806
```

```
                        -continued
  K    C    P    S    P    G    C    Q    E    A    F    L    T    F CTC TGT GTG ATG TGT ATC TGC AGC CTG ATC GGT GCC ATG GCA           1848
 L   C   V   M   C   I   C   S   L   I   G   A   M   A CAG ACA CCC TCA GTC ATC ATC CTC ATC AGG ACA GTC AGC CCT           1890
 Q   T   P   S   V   I   I   L   I   R   T   V   S   P GAA CTC AAG TCT TAC GCT TTG GGA GTT CTT TTT CTC CTC CTT           1932
 E   L   K   S   Y   A   L   G   V   L   F   L   L   L CGT TTG TTG GGC TTC ATC CCT CCA CCC CTC ATC TTC GGG GCT           1974
 R   L   L   G   F   I   P   P   P   L   I   F   G   A GGC ATC GAC TCC ACC TGC CTG TTC TGG AGC ACG TTC TGT GGG           2016
 G   I   D   S   T   C   L   F   W   S   T   F   C   G GAG CAA GGC GCC TGC GTC CTC TAC GAC AAT GTG GTC TAC CGA           2058
 E   Q   G   A   C   V   L   Y   D   N   V   V   Y   R TAC CTG TAT GTC AGC ATC GCC ATC GCG CTC AAA TCC TTC GCC           2100
 Y   L   Y   V   S   I   A   I   A   L   K   S   F   A TTC ATC CTG TAC ACC ACC ACG TGG CAG TGC CTG AGG AAA AAC           2142
 F   I   L   Y   T   T   T   W   Q   C   L   R   K   N TAT AAA CGC TAC ATC AAA AAC CAC GAG GGC GGG CTG AGC ACC           2184
 Y   K   R   Y   I   K   N   H   E   G   G   L   S   T AGT GAG TTC TTT GCC TCT ACT CTG ACC CTA GAC AAC CTG GGG           2226
 S   E   F   F   A   S   T   L   T   L   D   N   L   G AGG GAC CCT GTG CCC GCA AAC CAG ACA CAT AGG ACA AAG TTT           2268
 R   D   P   V   P   A   N   Q   T   H   R   T   K   F ATC TAT AAC CTG GAA GAC CAT GAG TGG TGT GAA AAC ATG GAG           2310
 I   Y   N   L   E   D   H   E   W   C   E   N   M   E TCC GTT TTA TAG TGACTAAAGG AGGGCTGAAC TCTGTATTAG TAATCCAAGG       2362
 S   V   L   *

GTCATTTTTT TCTTAAAAAA AGAAAAAAAG GTTCCAAAAA AAACCAAAAC            2412

TCAGTACACA CACACAGGCA CAGATGCACA CACACGCAGA CAGACACACC            2462

GACTTTGTCC TTTTTCTCAG CATCAGAGCC AGACAGGATT CAGAATAAGG            2512

AGAGAATGAC ATCGTGCGGC AGGGTCCTGG AGGCCACTCG CGCGGCTGGG            2562

CCACAGAGTC TACTTTGAAG GCACCTCATG GTTTTCAGGA TGCTGACAGC            2612

TGCAAGCAAC AGGCACTGCC AAATTCAGGG AACAGTGGTG GCCAGCTTGG            2662

AGGATGGACA TTTCTGGATA CACATACACA TACAAAACAG AAAACATTTT            2712

TTAAAAGAAG TTTCCTAAAA TAAAAAAAAT AAAAAAAAAA AAAAA                 2757

OATP-RP4 (SEQ ID NOS: 7 and 8) (Nucleotide 713, designated Y,
can be either a C (in which case the encoded amino acid X is
Leu) or a T (in which case the encoded amino acid X is Phe);
Nucleotide 2397, designated K, can be either a G (in which case
the encoded amino acid X is Gly) or a T (in which case the
encoded amino acid X is Val):
CTGATTTCTC TTCGGCTGGA CGGAGGCTGC CTCCTCACGC GGCTCCCAAC             50

TATTCCCGTA GCTCAGTGCC CCCCTCCCGC CGCTCTACTC AGCCAGGCAG            100

ACAGACTGAC AGACTCGCTA GTCGGCAGCT TCACTCCCGA GGGTGCCGCG            150

AGCCCAGGCG GCGAACACCC GGTACCCCTG GCGCAGCGAG GTGGGATGCT            200

GTACGGACAG CAGCGCTAAG TGCCCCCCCA CCCCCGGCGC AGGGTGCACT            250

CGCTCCTGGC CGCGGGCCCA GCGGCGGCGG CGGCGGCGGC GGCGGAGGGG            300

ATGAGCCCGG GACGCGCGAG GCGCCTGCCT CAAGCTACCG CCCGGAGAGG            350

GACGCCGAGT AGGGCTCATC GCAGTACCGC GCGGACCCCT GCCCCCTGTG            400

GCACGCGGCT GCGGAGCCTT GAAGCCGTGT CTGTGATCAG GATGCACTGG            450
```

-continued

```
GCGCCTCGCA GCTGGTGAGG ATGCCCTGCT GCGCGGCCCT GCGCCCCCAG       500

CCCCAGTCCC AGGTGGGCAA GACTGACTGG GCCCGGCTTC GGCCCCTCGT       550

GCCGGTGGAT GAAACGTGCC GGAGTGCTTG GGTGCCATCA GCTATCAAAT       600

CTGAATTCTA AGCGCC ATG GAC GAA GGC ACT GGA CTG GAG CCC GGG   646
              M   D   E   G   T   G   L   Q   P   G

GCG GGA GAG CAG CTG GAG GCG CCG GCC ACT GCA GAA GCT GTC     688
 A   G   E   Q   L   E   A   P   A   T   A   E   A   V

CAA GAG AGG TGC GAG CCG GAG ACC YTC AGG TCT AAG AGT TTA     730
 Q   E   R   C   E   P   E   T   X   R   S   K   S   L

CCG GTC CTC AGC AGC GCC TCC TGC CGG CCA AGC CTC AGT CCC     772
 P   V   L   S   S   A   S   C   R   P   S   L   S   P

ACT AGT GGA GAC GCC AAC CCG GCC TTT GGC TGT GTG GAT TCT     814
 T   S   G   D   A   N   P   A   F   G   C   V   D   S

TCG GGC CAC CAG GAG TTG AAG CAA GGC CCG AAC CCG TTG GCC     856
 S   G   H   Q   E   L   K   Q   G   P   N   P   L   A

CCC AGT CCC TCT GCC CCG TCC ACT TCG GCG GGG CTC GGG GAC     898
 P   S   P   S   A   P   S   T   S   A   G   L   G   D

TGT AAC CAC AGG GTG GAC CTC AGC AAA ACC TTC TCG GTG TCC     940
 C   N   H   R   V   D   L   S   K   T   F   S   V   S

TCC GCC TTG GCC ATG CTC CAG GAG AGA AGG TGC CTC TAC GTG     982
 S   A   L   A   M   L   Q   E   R   R   C   L   Y   V

GTC CTC ACG GAT TCC CGT TGC TTC CTG GTG TGC ATG TGG TTT    1024
 V   L   T   D   S   R   C   F   L   V   C   M   W   F

CTG ACC TTC ATC CAG GCG TTA ATG GTC TCT GGG TAC CTG AGC    1066
 L   T   F   I   Q   A   L   M   V   S   G   Y   L   S

AGC GTA ATT ACC ACC ATT GAA AGG CGC TAC AGT CTG AAG AGT    1108
 S   V   I   T   T   I   E   R   R   Y   S   L   K   S

TCC GAG TCG GGC CTG CTG GTC AGC TGC TTT GAC ATC GGG AAC    1150
 S   E   S   G   L   L   V   S   C   F   D   I   G   N

CTG GTG GTG GTG GTG TTC GTC AGC TAC TTC GGC GGC CGG GGT    1192
 L   V   V   V   V   F   V   S   Y   F   G   G   R   G

CGG CGG CCC CTG TGG CTG GCC GTG GGT GGA CTC CTC ATC GCC    1234
 R   R   P   L   W   L   A   V   G   G   L   L   I   A

TTC GGG GCA GCC CTC TTC GCC TTA CCT CAC TTC ATC TCG CCC    1276
 F   G   A   A   L   F   A   L   P   H   F   I   S   P

CCC TAC CAG ATC CAA GAG TTG AAC GCC TCG GCC CCC AAC GAC    1318
 P   Y   Q   I   Q   E   L   N   A   S   A   P   N   D

GGC CTG TGT CAG GGT GGC AAC TCC ACC GCC ACT TTG GAG CCT    1360
 G   L   C   Q   G   G   N   S   T   A   T   L   E   P

CCG GCC TGT CCG AAG GAC TCG GGA GGA AAT AAT CAC TGG GTC    1402
 P   A   C   P   K   D   S   G   G   N   N   H   W   V

TAC CTG GCT TTA TTC ATT TGC GCG CAG ATT CTC ATT GGA ATG    1444
 Y   L   A   L   F   I   C   A   Q   I   L   I   G   M

GGC TCC ACA CCT ATT TAT ACC CTG GGA CCA ACC TAC TTA GAT    1486
 G   S   T   P   I   Y   T   L   G   P   T   Y   L   D

GAC AAT GTC AAG AAA GAA AAC TCC TCC TTG TAC CTA GCC ATC    1528
 D   N   V   K   K   E   N   S   S   L   Y   L   A   I

ATG TAT GTC ATG GGA GCA CTT GGC CCT GCA GTG GGA TAT TTA    1570
 M   Y   V   M   G   A   L   G   P   A   V   G   Y   L

TTA GGT GGA CTT CTT ATT GGT TTT TAT GTT GAT CCC AGA AAT    1612
 L   G   G   L   L   I   G   F   Y   V   D   P   R   N

CCT GTT CAC CTT GAC CAG AAT GAC CCT CGT TTC ATT GGA AAC    1654
```

```
                    -continued
      P   V   H   L   D   Q   N   D   P   R   F   I   G   N TGG TGG AGT GGA TTC CTC CTT TGT GCC ATT GCA ATG TTT CTT      1696
 W   W   S   G   F   L   L   C   A   I   A   M   F   L GTG ATA TTC CCA ATG TTT ACT TTC CCA AAA AAG CTT CCA CCT      1738
 V   I   F   P   M   F   T   F   P   K   K   L   P   P CGA CAC AAG AAA AAG AAA AAG AAA AAA TTT TCT GTT GAT GCT      1780
 R   H   K   K   K   K   K   K   K   F   S   V   D   A GTT AGT GAT GAC GAT GTT CTG AAG GAG AAA TCA AAC AAC AGT      1822
 V   S   D   D   D   V   L   K   E   K   S   N   N   S GAA CAA GCG GAC AAA AAA GTT TCT TCG ATG GGA TTT GGA AAG      1864
 E   Q   A   D   K   K   V   S   S   M   G   F   G   K GAT GTC AGA GAC CTA CCA AGA GCA GCT GTC AGG ATC TTA AGC      1906
 D   V   R   D   L   P   R   A   A   V   R   I   L   S AAC ATG ACA TTC CTT TTT GTG AGT TTG TCA TAC ACA GCT GAG      1948
 N   M   T   F   L   F   V   S   L   S   Y   T   A   E AGT GCC ATT GTA ACT GCT TTC ATT ACC TTC ATT CCC AAG TTC      1990
 S   A   I   V   T   A   F   I   T   F   I   P   K   F ATC GAG TCA CAG TTT GGT ATC CCA GCC TCC AAT GCC AGC ATC      2032
 I   E   S   Q   F   G   I   P   A   S   N   A   S   I TAC ACT GGG GTT ATT ATC GTC CCC AGT GCT GGT GTT GGT ATT      2074
 Y   T   G   V   I   I   V   P   S   A   G   V   G   I GTC CTC GGA GGC TAC ATT ATA AAA AAA TTG AAA CTT GGT GCC      2116
 V   L   G   G   Y   I   I   K   K   L   K   L   G   A AGA GAA TCT GCA AAA CTA GCA ATG ATC TGC AGT GGT GTG TCT      2158
 R   E   S   A   K   L   A   M   I   C   S   G   V   S TTA CTA TGT TTT TCA ACC CTA TTT ATT GTT GGA TGT GAA AGC      2200
 L   L   C   F   S   T   L   F   I   V   G   C   E   S ATT AAT CTA GGG GGC ATA AAC ATC CCT TAT ACA ACA GGA CCT      2242
 I   N   L   G   G   I   N   I   P   Y   T   T   G   P TCT CTC ACC ATG CCC CAT AGG AAT CTG ACA GGA AGC TGC AAC      2284
 S   L   T   M   P   H   R   N   L   T   G   S   C   N GTT AAT TGT GGT TGT AAA ATA CAC GAG TAT GAG CCA GTC TGT      2326
 V   N   C   G   C   K   I   H   E   Y   E   P   V   C GGA TCA GAT GGA ATT ACA TAC TTT AAC CCT TGT CTG GCT GGC      2368
 G   S   D   G   I   T   Y   F   N   P   C   L   A   G TGT GTT AAT AGT GGT AAT CTT AGC ACT GKG ATA CGG AAT TAT      2410
 C   V   N   S   G   N   L   S   T   X   I   R   N   Y ACA GAA TGC ACC TGT GTC CAA AGT CGC CAA GTG ATC ACT CCA      2452
 T   E   C   T   C   V   Q   S   R   Q   V   I   T   P CCC ACC GTG GGA CAG CGA AGT CAG CTC CGT GTG GTT ATT GTC      2494
 P   T   V   G   Q   R   S   Q   L   R   V   V   I   V AAG ACT TAT CTC AAT GAG AAC GGC TAT GCT GTG TCT GGG AAA      2536
 K   T   Y   L   N   E   N   G   Y   A   V   S   G   K TGT AAA CGG ACC TGC AAT ACT CTT ATC CCA TTC TTA GTT TTT      2578
 C   K   R   T   C   N   T   L   I   P   F   L   V   F CTT TTC ATA GTC ACC TTC ATC ACA GCA TGT GCC CAA CCA TCA      2620
 L   F   I   V   T   F   I   T   A   C   A   Q   P   S GCT ATC ATA GTA ACA CTC AGG TCC GTA GAA GAT GAG GAG AGA      2662
 A   I   I   V   T   L   R   S   V   E   D   E   E   R CCT TTT GCA CTG GGA ATG CAG TTT GTT TTG TTG CGA ACA CTT      2704
 P   F   A   L   G   M   Q   F   V   L   L   R   T   L GCA TAC ATT CCT ACT CCA ATC TAC TTT GGA GCA GTC ATT GAC      2746
 A   Y   I   P   T   P   I   Y   F   G   A   V   I   D
```

-continued

```
ACC ACC TGC ATG CTC TGG CAA CAG GAA TGT GGT GTG CAG GGT      2788
 T   T   C   M   L   W   Q   Q   E   C   G   V   Q   G

TCT TGC TGG GAG TAC AAC GTG ACG TCG TTT CGT TTT GTG TAT      2830
 S   C   W   E   Y   N   V   T   S   F   R   F   V   Y

TTT GGT TTG GCT GCC GGC CTC AAA TTC GTT GGG TTT ATT TTT      2872
 F   G   L   A   A   G   L   K   F   V   G   F   I   F

ATT TTT CTG GCC TGG TAC TCC ATA AAA TAC AAG GAG GAT GGA      2914
 I   F   L   A   W   Y   S   I   K   Y   K   E   D   G

CTG CAG AGG CGG AGG CAG AGA GAA TTT CCC CTG AGC ACC GTG      2956
 L   Q   R   R   R   Q   R   E   F   P   L   S   T   V

AGT GAG AGA GTG GGA CAC CCC GAC AAT GCC CGG ACT AGA TCT      2998
 S   E   R   V   G   H   P   D   N   A   R   T   R   S

TGC CCA GCT TTC AGC ACC CAG GGA GAA TTC CAC GAA GAG ACT      3040
 C   P   A   F   S   T   Q   G   E   F   H   E   E   T

GGC CTG CAA AAA GGG ATC CAG TGC GCA GCA CAG ACC TAC CCG      3082
 G   L   Q   K   G   I   Q   C   A   A   Q   T   Y   P

GGG CCC TTC CCA GAA GCA ATA AGT TCC TCT GCG GAC CCG GGG      3124
 G   P   F   P   E   A   I   S   S   S   A   D   P   G

CTG GAA GAG AGC CCC GCT GCC TTG GAG CCG CCC TCC TGA          3163
 L   E   E   S   P   A   A   L   E   P   P   S   *

AGCTTGAAAA TGGAAGAATT TAGTTTTGTT GGTTGAATTG AAAATGGCGA       3213
CTTGAGAAAC AACTGTGCCT TCTTTTCTTT CTTTCTTTTT TTTAACCTCT       3263
ACAGACACAA TCCTCAAACC AACAAAACTC AGTATACACA GCCGCTATTC       3313
ATTGAGGGCT GGATACCTCA ACAAGACTGA GAGCCTTTCC CCGCTTCTCT       3363
CCAAGAAGGA GACGTTCAGC TAGATTTGTT CCCATTTCCG TTGTGTTAAT       3413
TCAAAGCTCA TGCTCCCCTA CGGTACAGGC TGAGGTACAC GGTTAGCAAA       3463
ACCATGGGAA GGGGAATGGC GGTGCATATC ATTAACTAAC ACTCCAAACA       3513
AAGGTGAGCT TGCCCAGGAC TTGGCATTTC CAAATCAAAG TTTTTAGATA       3563
TGAACACCTA CTGTGAGTTC TGCTACAAAG CACAAATGAA TTTGTCTCAA       3613
CTATGCAATT TGATTGGAAA AATGTATGTG CAGCATGTTA CATTTACTTT       3663
CACGGAATAA AGCAGATATG TTTCTGAAA                              3692

OATP-RP5 (SEQ ID NOS: 9 and 10):
CGCAAAGAAA TGGCTCAAAA GCTTCAGCTC TTTCTGTGCC CTGGGAGCTG        50
AGATGCACGT CAGTGGCCTT GCCAGCGTGG CCAATTCTCT GCTGACTGCC       100
AGAAAAAAGA GGCCAGGAAG AAAGAGGAAA GAGAAGAGAT CGCTCAGGGG       150
TGAGACCATG CCCTTCATCT TTTCTTTTCC CTAATCTCCT CTGCTTGTGT       200
CCACCCACAC TCTCCCCACC TGGCAAAATT GTTCAAAATT GCTGTGGAGT       250
TTACCTCAGT TTCCTCTTTC AGTCTGTGGT GTGTGGTCCA TCCTCTTGCT       300
GAGCACATTG AAAGGAACTG GCTATCTTTG ATCTCTTCCT CCAGATCAGA       350

GTCAAGGAAT GTGTTTATA ATG GAC ACT TCA TCC AAA GAA AAT ATC     396
                      M   D   T   S   S   K   E   N   I

CAG TTG TTC TGC AAA ACT TCA GTG CAA CCT GTT GGA AGG CCT      438
 Q   L   F   C   K   T   S   V   Q   P   V   G   R   P

TCT TTT AAA ACA GAA TAT CCC TCC TCA GAA GAA AAG CAA CCA      480
 S   F   K   T   E   Y   P   S   S   E   E   K   Q   P

TGC TGT GGT GAA CTA AAG GTG TTC TTG TGT GCC TTG TCT TTT      522
 C   C   G   E   L   K   V   F   L   C   A   L   S   F

GTT TAC TTT GCC AAA GCA TTG GCA GAA GGC TAT CTG AAG AGC      564
 V   Y   F   A   K   A   L   A   E   G   Y   L   K   S
```

```
                    -continued
    V   Y   F   A   K   A   L   A   E   G   Y   L   K   S
ACC ATC ACT CAG ATA GAG AGA AGG TTT GAT ATC CCT TCT TCA         606
 T   I   T   Q   I   E   R   R   F   D   I   P   S   S CTG GTG GGA GTT ATT GAT GGT AGT TTT GAA ATT GGG AAT CTC         648
 L   V   G   V   I   D   G   S   F   E   I   G   N   L TTA GTT ATA ACA TTT GTT AGC TAC TTT GGA GCC AAA CTT CAC         690
 L   V   I   T   F   V   S   Y   F   G   A   K   L   H AGG CCA AAA ATA ATT GGA GCA GGG TGT GTA ATC ATG GGA GTT         732
 R   P   K   I   I   G   A   G   C   V   I   M   G   V GGA ACA CTG CTC ATT GCA ATG CCT CAG TTC TTC ATG GAG CAG         774
 G   T   L   L   I   A   M   P   Q   F   F   M   E   Q TAC AAA TAT GAG AGA TAT TCT CCT TCC TCC AAT TCC ACT CTC         816
 Y   K   Y   E   R   Y   S   P   S   S   N   S   T   L AGC ATC TCT CCG TGT CTC CTA GAG TCA AGC AGT CAA TTA CCA         858
 S   I   S   P   C   L   L   E   S   S   S   Q   L   P GTT TCA GTT ATG GAA AAA TCA AAA TCC AAA ATA AGT AAC GAA         900
 V   S   V   M   E   K   S   K   S   K   I   S   N   E TGT GAA GTG GAC ACT AGC TCT TCC ATG TGG ATT TAT GTT TTC         942
 C   E   V   D   T   S   S   S   M   W   I   Y   V   F CTG GGC AAT CTT CTT CGT GGA ATA GGA GAA ACT CCC ATT CAG         984
 L   G   N   L   L   R   G   I   G   E   T   P   I   Q CCT TTG GGC ATT GCC TAC CTG GAT GAT TTT GCC AGT GAA GAC         1026
 P   L   G   I   A   Y   L   D   D   F   A   S   E   D AAT GCA GCT TTC TAT ATT GGG TGT GTG CAG ACG GTT GCA ATT         1068
 N   A   A   F   Y   I   G   C   V   Q   T   V   A   I ATA GGA CCA ATC TTT GGT TTC CTG TTA GGC TCA TTA TGT GCC         1110
 I   G   P   I   F   G   F   L   L   G   S   L   C   A AAA CTA TAT GTT GAC ATT GGC TTT GTA AAC CTA GAT CAC ATA         1152
 K   L   Y   V   D   I   G   F   V   N   L   D   H   I ACC ATT ACC CCA AAA GAT CCC CAG TGG GTA GGA GCC TGG TGG         1194
 T   I   T   P   K   D   P   Q   W   V   G   A   W   W CTT GGC TAT CTA ATA GCA GGA ATC ATA AGT CTT CTT GCA GCT         1236
 L   G   Y   L   I   A   G   I   I   S   L   L   A   A GTG CCT TTC TGG TAT TTA CCA AAG AGT TTA CCA AGA TCC CAA         1278
 V   P   F   W   Y   L   P   K   S   L   P   R   S   Q AGT AGA GAG GAT TCT AAT TCT TCC TCT GAG AAA TCC AAG TTT         1320
 S   R   E   D   S   N   S   S   S   E   K   S   K   F ATT ATA GAT GAT CAC ACA GAC TAC CAA ACA CCC CAG GGA GAA         1362
 I   I   D   D   H   T   D   Y   Q   T   P   Q   G   E AAT GCA AAA ATA ATG GAA ATG GCA AGA GAT TTT CTT CCA TCA         1404
 N   A   K   I   M   E   M   A   R   D   F   L   P   S CTG AAG AAT CTT TTT GGA AAC CCA GTA TAC TTC CTA TAT TTA         1446
 L   K   N   L   F   G   N   P   V   Y   F   L   Y   L TGT ACA AGC ACT GTT CAG TTC AAT TCT CTG TTC GGC ATG GTG         1488
 C   T   S   T   V   Q   F   N   S   L   F   G   M   V ACG TAC AAA CCA AAG TAC ATT GAG CAG CAG TAT GGA CAG TCA         1530
 T   Y   K   P   K   Y   I   E   Q   Q   Y   G   Q   S TCC TCC AGG GCC AAC TTT GTG ATC GGG CTC ATC AAC ATT CCA         1572
 S   S   R   A   N   F   V   I   G   L   I   N   I   P GCA GTG GCC CTT GGA ATA TTC TCT GGG GGA ATA GTT ATG AAA         1614
 A   V   A   L   G   I   F   S   G   G   I   V   M   K AAA TTC AGA ATC AGT GTG TGT GGA GCT GCA AAA CTC TAC TTG         1656
 K   F   R   I   S   V   C   G   A   A   K   L   Y   L
```

```
                     -continued
GGA TCA TCT GTC TTT GGT TAC CTC CTA TTT CTT TCC CTG TTT    1698
 G   S   S   V   F   G   Y   L   L   F   L   S   L   F GCA CTG GGC TGT GAA AAT TCT GAT GTG GCA GGA CTA ACT GTC    1740
 A   L   G   C   E   N   S   D   V   A   G   L   T   V TCC TAC CAA GGA ACC AAA CCT GTC TCT TAT CAT GAA CGA GCT    1782
 S   Y   Q   G   T   K   P   V   S   Y   H   E   R   A CTC TTT TCA GAT TGC AAC TCA AGA TGC AAA TGT TCA GAG ACA    1824
 L   F   S   D   C   N   S   R   C   K   C   S   E   T AAA TGG GAA CCC ATG TGC GGT GAA AAT GGA ATC ACA TAT GTA    1866
 K   W   E   P   M   C   G   E   N   G   I   T   Y   V TCA GCT TGT CTT GCT GGT TGT CAA ACC TCC AAC AGG AGT GGA    1908
 S   A   C   L   A   G   C   Q   T   S   N   R   S   G AAA AAT ATT ATA TTT TAC AAC TGC ACT TGT GTG GGA ATT GCA    1950
 K   N   I   I   F   Y   N   C   T   C   V   G   I   A GCT TCT AAA TCC GGA AAT TCC TCA GGC ATA GTG GGA AGA TGT    1992
 A   S   K   S   G   N   S   S   G   I   V   G   R   C CAG AAA GAC AAT GGA TGT CCC CAA ATG TTT CTG TAT TTC CTT    2034
 Q   K   D   N   G   C   P   Q   M   F   L   Y   F   L GTA ATT TCA GTC ATC ACA TCC TAT ACT TTA TCC CTA GGT GGC    2076
 V   I   S   V   I   T   S   Y   T   L   S   L   G   G ATA CCT GGA TAC ATA TTA CTT CTG AGG TGC ATT AAG CCA CAG    2118
 I   P   G   Y   I   L   L   L   R   C   I   K   P   Q CTT AAG TCT TTT GCC TTG GGT ATC TAC ACA TTA GCA ATA AGA    2160
 L   K   S   F   A   L   G   I   Y   T   L   A   I   R GTT CTT GCA GGA ATC CCA GCT CCA GTG TAT TTT GGA GTT TTG    2202
 V   L   A   G   I   P   A   P   V   Y   F   G   V   L ATT GAT ACT TCA TGC CTC AAA TGG GGA TTT AAA AGA TGT GGA    2244
 I   D   T   S   C   L   K   W   G   F   K   R   C   G AGT AGA GGA TCA TGC AGA TTA TAT GAT TCA AAT GTC TTC AGA    2286
 S   R   G   S   C   R   L   Y   D   S   N   V   F   R CAT ATA TAT TTG GGA CTA ACT GTG ATA CTG GGC ACA GTG TCA    2328
 H   I   Y   L   G   L   T   V   I   L   G   T   V   S ATT CTC CTA AGC ATT GCA GTA CTT TTC ATT TTA AAG AAA AAT    2370
 I   L   L   S   I   A   V   L   F   I   L   K   K   N TAT GTT TCA AAA CAC AGA AGT TTT ATA ACC AAG AGA GAA AGA    2412
 Y   V   S   K   H   R   S   F   I   T   K   R   E   R ACA ATG GTG TCT ACA AGA TTC CAA AAG GAA AAT TAC ACT ACA    2454
 T   M   V   S   T   R   F   Q   K   E   N   Y   T   T AGT GAT CAT CTG CTA CAA CCC AAC TAC TGG CCA GGC AAG GAA    2496
 S   D   H   L   L   Q   P   N   Y   W   P   G   K   E

ACT CAA CTT TAG AAACATGATG ACTGGAAGTC ATGTCTTCTA           2538
 T   Q   L   *

ATTGGTTGAC ATTTTGCAAA CAAATAAATT GTAATCAAAA GAGCTCTAAA     2588

TTTGTAATTT CTTTCTCCTT TCAAAAAATG TCTACTTTGT TTTGGTCCTA     2638

GGCATTAGGT AATATAACTG ATAATATACT GAAATATATA ATGGAAGATG     2688

CAGATGATAA AACTAATTTT GAACTTTTTA ATTTATATAA ATTATTTTAT     2738

ATCATTTACT TATTTCACTT TATTTTGCTT TGTGCTCATT GATATATATT     2788

AGCTGTACTC CTAGAAGAAC AATTGTCTCT ATTGTCACAC ATGGTTATAT     2838

TTAAAGTAAT TTCTGAACTG TGTAATGTGT CTAGAGTAAG CAAATACTGC     2888

TAACAATTAA CTCATACCTT GGGTTCCTTC AAGTATTACT CCTATAGTAT     2938

TTTCTCCCAT AGCTGTCTTC ATCTGTGTAT TTAATAATG ATCTTAGGAT      2988
```

-continued

```
GGAGCAGAAC ATGGAGAGGA AGATTTCATT TTAAGCTCCT CCTTTTCCTT    3038

GAAATACAAT AATTTATATA GAAATGTGTA GCAGCAAATT ATATTGGGGA    3088

TTAGAATTTT GAATTAATAG CTCTCCTACT ATTAATTTAC ATGTGCTTTT    3138

TGTGTGGCGC TATAAGTGAC TATGGTTGTA AAGTAATAAA ATTGATGTTA    3188

ACATGCCCAA TTATTGTTCT TTTATGAATT CAATGAATTT AAAACTATTG    3238

TTAAATATAA TACTGCCCCA CTTTAATATA TGTAAGCAAC TTCCTACTTA    3288

TACACGACGT GTTCCTAAAA CATGTTTGAA AGGTGAATTT CTGAAAGTCT    3338

CCCATAAATG TAGGTGTTAC AACAGGAAAA AAAAAAAAAA AAA          3381

OATP-RP1 (SEQ ID NOS: 11 and 12):
                              GGCACGAG GCGCTGCGCG    18

GCGCGGCGGC CGGGCCCTCG AGACGGGGAC GGACACACCA GCCCCTCGGA    68

TACCACTTGG CCACTCCCGC TGAGGCCACT CCCACTGCGT GGCTGAAGCC   118

TCGAGGTCAC CAGGCGGAGG CGCGGAG ATG CCC CTG CAT CAG CTG GGG  166
                              M   P   L   H   Q   L   G

GAC AAG CCG CTC ACC TTC CCC AGC CCC AAC TCA GCC ATG GAA   208
 D   K   P   L   T   F   P   S   P   N   S   A   M   E

AAC GGG CTT GAC CAC ACC CCA CCC AGC AGG AGG GCA TCC CCG   250
 N   G   L   D   H   T   P   P   S   R   R   A   S   P

GGC ACA CCC CTG AGC CCC GGG TCC CTC CGC TCC GCT GCC CAT   292
 G   T   P   L   S   P   G   S   L   R   S   A   A   H

AGC CCC CTG GAC ACC AGC AAG CAG CCC CTC TGC CAG CTC TGG   334
 S   P   L   D   T   S   K   Q   P   L   C   Q   L   W

GCC GAG AAG CAT GGC GCC CGG GGG ACC CAT GAG GTG CGG TAC   376
 A   E   K   H   G   A   R   G   T   H   E   V   R   Y

GTC TCG GCC GGG CAG AGC GTG GCG TGC GGC TGG TGG GCC TTC   418
 V   S   A   G   Q   S   V   A   C   G   W   W   A   F

GCA CCG CCG TGC CTG CAG GTC CTC AAC ACG CCC AAG GGC ATC   460
 A   P   P   C   L   Q   V   L   N   T   P   K   G   I

CTG TTC TTC CTG TGT GCG GCC GCA TTC CTG CAG GGG ATG ACT   502
 L   F   F   L   C   A   A   A   F   L   Q   G   M   T

GTG AAT GGC TTC ATC AAC ACA GTC ATC ACC TCC CTG GAG CGC   544
 V   N   G   F   I   N   T   V   I   T   S   L   E   R

CGC TAT GAC CTG CAC AGC TAC CAG AGC GGG CTC ATC GCC AGC   586
 R   Y   D   L   H   S   Y   Q   S   G   L   I   A   S

TCC TAC GAC ATT GCC GCC TGC CTC TGC CTC ACC TTC GTC AGC   628
 S   Y   D   I   A   A   C   L   C   L   T   F   V   S

TAC TTC GGG GGC TCA GGG CAC AAG CCG CGC TGG CTG GGC TGG   670
 Y   F   G   G   S   G   H   K   P   R   W   L   G   W

GGC GTG CTG CTT ATG GGC ACG GGG TCG CTG GTG TTC GCG CTG   712
 G   V   L   L   M   G   T   G   S   L   V   F   A   L

CCC CAC TTC ACG GCT GGC CGC TAT GAG GTG GAG TTG GAC GCG   754
 P   H   F   T   A   G   R   Y   E   V   E   L   D   A

GGT GTC AGG ACG TGC CCT GCC AAC CCC GGC GCG GTG TGT GCG   796
 G   V   R   T   C   P   A   N   P   G   A   V   C   A

GAC AGC ACC TCG GGC CTG TCC CGC TAC CAG CTG GTC TTC ATG   838
 D   S   T   S   G   L   S   R   Y   Q   L   V   F   M

CTG GGC CAG TTC CTG CAT GGC GTG GGT GCC ACA CCC CTC TAC   880
 L   G   Q   F   L   H   G   V   G   A   T   P   L   Y

ACG CTG GGC GTC ACC TAC CTG GAT GAG AAC GTC AAG TCC AGC   922
 T   L   G   V   T   Y   L   D   E   N   V   K   S   S
```

-continued

```
TGC TCG CCC GTC TAC ATT GCC ATC TTC TAC ACA GCG GCC ATC    964
 C   S   P   V   Y   I   A   I   F   Y   T   A   A   I

CTG GGC CCA GCT GCC GGC TAC CTG ATT GGA GGT GCC CTG CTG   1006
 L   G   P   A   A   G   Y   L   I   G   G   A   L   L

AAT ATC TAC ACG GAA ATG GGC CGA CGG ACG GAG CTG ACC ACC   1048
 N   I   Y   T   E   M   G   R   R   T   E   L   T   T

GAG AGC CCA CTG TGG GTC GGC GCC TGG TGG GTC GGC TTC CTG   1090
 E   S   P   L   W   V   G   A   W   W   V   G   F   L

GGC TCT GGG GCC GCT GCT TTC TTC ACC GCC GTT CCC ATC CTT   1132
 G   S   G   A   A   A   F   F   T   A   V   P   I   L

GGT TAC CCT CGG CAG CTG CCA GGC TCC CAG CGC TAC GCG GTC   1174
 G   Y   P   R   Q   L   P   G   S   Q   R   Y   A   V

ATG AGA GCG GCG GAA ATG CAC CAG TTG AAG GAC AGC AGC CGT   1216
 M   R   A   A   E   M   H   Q   L   K   D   S   S   R

GGG GAG GCG AGC AAC CCG GAC TTT GGG AAA ACC ATC AGA GAC   1258
 G   E   A   S   N   P   D   F   G   K   T   I   R   D

CTG CCT CTC TCC ATC TGG CTC CTG CTG AAG AAC CCC ACG TTC   1300
 L   P   L   S   I   W   L   L   L   K   N   P   T   F

ATC CTG CTC TGC CTG GCC GGG GCC ACC GAG GCC ACT CTC ATC   1342
 I   L   L   C   L   A   G   A   T   E   A   T   L   I

ACC GGC ATG TCC ACG TTC AGC CCC AAG TTC TTG GAG TCC CAG   1384
 T   G   M   S   T   F   S   P   K   F   L   E   S   Q

TTC AGC CTG AGT GCC TCA GAA GCT GCC ACC TTG TTT GGG TAC   1426
 F   S   L   S   A   S   E   A   A   T   L   F   G   Y

CTG GTG GTG CCA GCG GGT GGT GGC GGC ACC TTC CTG GGC GGC   1468
 L   V   V   P   A   G   G   G   G   T   F   L   G   G

TTC TTT GTG AAC AAG CTC AGG CTC CGG GGC TCC GCG GTC ATC   1510
 F   F   V   N   K   L   R   L   R   G   S   A   V   I

AAG TTC TGC CTG TTC TGC ACC GTT GTC AGC CTG CTG GGC ATC   1552
 K   F   C   L   F   C   T   V   V   S   L   L   G   I

CTC GTC TTC TCA CTG CAC TGC CCC AGT GTG CCC ATG GCG GGC   1594
 L   V   F   S   L   H   C   P   S   V   P   M   A   G

GTC ACA GCC AGC TAC GGC GGG AGC CTC CTG CCC GAA GGC CAC   1636
 V   T   A   S   Y   G   G   S   L   L   P   E   G   H

CTG AAC CTA ACG GCT CCC TGC AAC GCT GCC TGC AGC TGC CAG   1678
 L   N   L   T   A   P   C   N   A   A   C   S   C   Q

CCA GAA CAC TAC AGC CCT GTG TGC GGC TCG GAC GGC CTC ATG   1720
 P   E   H   Y   S   P   V   C   G   S   D   G   L   M

TAC TTC TCA CTG TGC CAC GCA GGG TGC CCT GCA GCC ACG GAG   1762
 Y   F   S   L   C   H   A   G   C   P   A   A   T   E

ACG AAT GTG GAC GGC CAG AAG GTG TAC CGA GAC TGT AGC TGT   1804
 T   N   V   D   G   Q   K   V   Y   R   D   C   S   C

ATC CCT CAG AAT CTT TCC TCT GGT TTT GGC CAT GCC ACT GCA   1846
 I   P   Q   N   L   S   S   G   F   G   H   A   T   A

GGG AAA TGC ACT TCA ACT TGT CAG AGA AAG CCC CTC CTT CTG   1888
 G   K   C   T   S   T   C   Q   R   K   P   L   L   L

GTT TTC ATA TTC GTT GTA ATT TTC TTT ACA TTC CTC AGC AGC   1930
 V   F   I   F   V   V   I   F   F   T   F   L   S   S

ATT CCT GCA CTA ACG GCA ACT CTA CGA TGT GTC CGT GAC CCT   1972
 I   P   A   L   T   A   T   L   R   C   V   R   D   P

CAG AGA TCC TTT GCC CTG GGA ATC CAG TGG ATT GTA GTT AGA   2014
 Q   R   S   F   A   L   G   I   Q   W   I   V   V   R

ATA CTA GGG GGC ATC CCG GGG CCC ATC GCC TTC GGC TGG GTG   2056
```

-continued

| | | | | | | | | | | | | |
|---|---|---|---|---|---|---|---|---|---|---|---|---|
| I | L | G | G | I | P | G | P | I | A | F | G | W | V |

| | | | | | | | | | | | |
|---|---|---|---|---|---|---|---|---|---|---|---|
| ATC | GAC | AAG | GCC | TGT | CTG | CTG | TGG | CAG | GAC | CAG | TGT | GGG | CAG | 2098 |
| I | D | K | A | C | L | L | W | Q | D | Q | C | G | Q |

```
ATC GAC AAG GCC TGT CTG CTG TGG CAG GAC CAG TGT GGG CAG    2098
 I   D   K   A   C   L   L   W   Q   D   Q   C   G   Q

CAG GGC TCC TGC TTG GTG TAC CAG AAT TCG GCC ATG AGC CGC    2140
 Q   G   S   C   L   V   Y   Q   N   S   A   M   S   R

TAC ATA CTC ATC ATG GGG CTC CTG TAC AAG GTG CTG GGC GTC    2182
 Y   I   L   I   M   G   L   L   Y   K   V   L   G   V

CTC TTC TTT GCC ATA GCC TGC TTC TTA TAC AAG CCC CTG TCG    2224
 L   F   F   A   I   A   C   F   L   Y   K   P   L   S

GAG TCT TCA GAT GGC CTG GAA ACT TGT CTG CCC AGC CAG TCC    2266
 E   S   S   D   G   L   E   T   C   L   P   S   Q   S

TCA GCC CCT GAC AGT GCC ACA GAT AGC CAG CTC CAG AGC AGC    2308
 S   A   P   D   S   A   T   D   S   Q   L   Q   S   S

GTC TGA CCACCGCCCG CGCCCACCCG GCCACGGCGG GCACTCAGCA        2354
 V   *

TTTCCTGATG ACAGAACAGT GCCGTTGGGT GATGCAATCA CACGGGAACT     2404

TCTATTTGAC CTGCAACCTT CTACTTAACC TGTGGTTTAA AGTCGGCTGT     2454

GACCTCCTGT CCCCAGAGCT GTACGGCCCT GCAGTGGGTG GGAGGAACTT     2504

GCATAAATAT ATATTTATGG ACACACAGTT TGCATCAGAA CGTGTTTATA     2554

GAATGTGTTT TATACCCGAT CGTGTGTGGT GTGCGTGAGG ACAAACTCCG     2604

CAGGGGCTGT GAATCCCACT GGGAGGGCGG CGGGCCTGCA GCCCGAGGAA     2654

GGCTTGTGTG TCCTCAGTTA AAACTGTGCA TATCGAAATA TATTTTGTTA     2704

TTTAAGCCTG CGAAAAAAAA AAAAAAAAAA AAAAAAAAAA AAAAAAAAAA     2754

AAAAAAAAA                                                  2763
```

Persons skilled in the art can also modify the nucleic acids coding for the OATPs of the present invention to prepare useful mutations. For example, one may modify the sequence to provide additional restriction endonuclease recognition sites in the nucleic acid. Such mutations may be silent or may change the amino acid encoded by the mutated codon. One can prepare these modified nucleic acids, for example, by mutating the nucleic acid coding for an OATP of the present invention to result in deletion, substitution, insertion, inversion or addition of one or more amino acids in the encoded polypeptide. For methods of site-directed mutagenesis, see Taylor, J. W. et al. (1985), Nucl. Acids Res. 13, 8749-64 and Kunkel, J. A. (1985), Proc. Natl. Acad. Sci. USA 82: 482-92. In addition, kits for site-directed mutagenesis are available from commercial vendors (e.g., BioRad Laboratories, Richmond, Calif.; Amersham Corp., Arlington Heights, Ill.). For disruption, deletion and truncation methods, see Sayers, J. R. et al. (1988), Nucl. Acids Res. 16: 791-800.

This invention also comprises modified nucleic acids, including (1) alternative splice exon variants; (2) allelic variants; and (3) chimeric proteins in which the fusion construct comprises an OATP or fragment thereof. Such modified nucleic acids can be obtained by persons of ordinary skill in the art when armed with the present disclosure.

Expression Vectors

This invention further concerns expression vectors comprising a nucleotide sequence encoding an OATP of the present invention. Preferably, the expression vectors comprise all or a portion of the nucleic acid sequence as shown in SEQ ID NO:1, SEQ ID NO:3, SEQ ID NO:5, SEQ ID NO:7, SEQ ID NO:9, or SEQ ID NO:11; preferred is a nucleotide sequence encoding an OATP as shown above (i.e., the coding region).

Expression vectors are usually plasmids, but the invention includes other vector forms that serve equivalent functions and become known in the art subsequently hereto. A person skilled in the art might also stably integrate a sequence encoding an OATP into the chromosome of an appropriate host cell.

Expression vectors typically contain regulatory elements capable of affecting expression of an OATP. These regulatory elements can be heterologous or native OATP elements. Typically, a vector contains an origin of replication, a promoter, and a transcription termination sequence. The vector may also include other regulatory sequences, including mRNA stability sequences, which provide for stability of the expression product; secretory leader sequences, which provide for secretion of the expression product; environmental feedback sequences, which allow expression of the structural gene to be modulated (e.g., by the presence or absence of nutrients or other inducers in the growth medium); marking sequences, which are capable of providing phenotypic selection in transformed host cells; restriction sites, which provide sites for cleavage by restriction endonucleases; and sequences which allow expression in various types of hosts, including prokaryotes, yeasts, fungi, plants and higher eukaryotes.

An expression vector of this invention is at least capable of directing the replication, and preferably the expression, of the nucleic acids and protein of this invention. Suitable origins of replication include, for example, the Col E1, the SV40 viral, Epstein Barr viral, and the M13 origins of replication. Suitable promoters include, for example, the cytomegalovirus promoter, the lacZ promoter, the gal10 promoter and the *Autographa californica* multiple nuclear polyhedrosis virus (AcMNPV) polyhedral promoter. Suitable termination sequences include, for example, the bovine growth hormone, SV40, lacZ and AcMNPV polyhedral polyadenylation signals. Examples of selectable markers include neomycin, ampicillin, and hygromycin resistance and the like.

Persons skilled in the art may insert DNA encoding An OATP of the present invention into several commercially available vectors. Examples include vectors compatible with mammalian cells, such as pcDNA3 or pCEP4; baculovirus vectors such as pBlueBac; prokaryotic vectors such as pcDNA2; and yeast vectors such as pYes2. For vector modification techniques, see Sambrook et al. (1989), *Molecular Cloning: A Laboratory Manual*, Second Edition, Cold Spring Harbor Laboratory, Cold Spring Harbor, N.Y.

Host Cells

This invention additionally concerns host cells containing an expression vector that comprises a sequence encoding an OATP, preferably the OATP2, OATP-RP2, OATP-RP3, OATP-RP4, OATP-RP5 or OATP-RP1 of the present invention. The host cells preferably contain an expression vector which comprises all or part of the DNA sequence having the nucleotide sequence substantially as shown in SEQ ID NO:1, SEQ ID NO:3, SEQ ID NO:5, SEQ ID NO:7, SEQ ID NO:9, or SEQ ID NO:11, particularly the coding regions thereof. Suitable host cells include both prokaryotic cells (e.g., *E. coli* strains HB101, DH5a, XL1 Blue, Y1090 and JM101) and eukaryotic cells (e.g., *Spodoptera frugiperda* insect cells, CHO cells, COS-7 cells, HEK 293 cells, human skin fibroblasts, and *S. cerevisiae* cells).

Persons skilled in the art may introduce expression vectors into host cells by various methods known in the art. Exemplary methods are transfection by calcium phosphate precipitation, electroporation, liposomal fusion, nuclear injection, and viral or phage infection. One may then culture the host cell under conditions permitting expression of large amounts of OATP.

One may identify such modified host cells by any of five general approaches:

(a) DNA-DNA hybridization with probes complementary to the sequence encoding an OATP (Southern blotting).

(b) detection of marker gene functions, such as thymidine kinase activity, resistance to antibiotics, and the like. A marker gene can be placed in the same plasmid as an OATP sequence under the regulation of the same or a different promoter.

(c) detection of mRNA transcripts by hybridization assays (e.g., Northern blotting or a nuclease protection assay using a probe complementary to the RNA sequence).

(d) immunodetection of gene expression (e.g., by Western blotting with antibody to OATP).

(e) PCR with primers homologous to expression vector sequences or sequences encoding OATP. The PCR produces a DNA fragment of predicted length, indicating incorporation of the expression system in the host cell.

Persons skilled in the art may determine DNA sequences by various known methods. See, for example, the dideoxy chain termination method in Sanger et al. (1977), *Proc. Natl. Acad. Sci. USA* 74: 5463-7 and the Maxam-Gilbert method in Maxam-Gilbert (1977), *Proc. Natl. Acad. Sci. USA* 74: 560-4.

One may use the host cells of this invention in a variety of ways that are now apparent. One may use the cells to screen for compounds that bind to or otherwise modulate or regulate the function of an OATP of the present invention, which would be useful for modulation, for example activation or inactivation, of OATP2, OATP-RP2, OATP-RP3, OATP-RP4, OATP-RP5 or OATP-RP1 activity; to study signal transduction mechanisms and protein-protein interactions; and to prepare OATP for the uses described below.

Not all expression vectors and DNA regulatory sequences will function equally well to express the DNA sequences of this invention. Neither will all host cells function equally well with the same expression system. However, one of ordinary skill in the art may make a selection among expression vectors, DNA regulatory sequences, and host cells using the guidance provided herein without undue experimentation and without departing from the scope of the invention.

Polypeptides

This invention further concerns polypeptides comprising all or a portion of the amino acid sequences of OATPs of the present invention. The inventors prefer polypeptides comprising all or a portion of the amino acid sequences shown as in SEQ ID NO:2 (OATP2), SEQ ID NO:4 (OATP-RP2), SEQ ID NO:6 (OATP-RP3), SEQ ID NO:8 (OATP-RP4), SEQ ID NO:10 (OATP-RP5) or SEQ ID NO:12 (OATP-RP1). Where a portion of an OATP of the present invention is used, preferably the portion exhibits the same biological activity of the OATP from which the portion is derived. For example, and within the scope of the invention, are polypeptides that comprise all or a portion of OATP2, OATP-RP2, OATP-RP3, OATP-RP4, OATP-RP5 or OATP-RP1 that exhibit transport activity. The portions may contain one or more mutations so that the protein(s) fail(s) to exhibit transport activity, but that can be used to screen for compounds that will modulate or bind to the protein or portion thereof.

Persons having ordinary skill in the art may prepare these polypeptides by methods known in the art. For example, one may use chemical synthesis, such as the solid phase procedure described by Houghton et al. (1985), *Proc. Natl. Acad. Sci.* 82: 5131-5. Another method is in vitro translation of mRNA. One may also produce the polypeptides in the above-described host cells, which is the preferred method. For example, one may synthesize DNA comprising all or a portion of SEQ ID NO:1, SEQ ID NO:3, SEQ ID NO:5, SEQ ID NO:7, SEQ ID NO:9, or SEQ ID NO:11 by PCR as described above, insert the synthesized DNA into an expression vector, transform a host cell with the expression vector, and culture the host cell to produce the desired polypeptides.

Persons skilled in the art can isolate and purify such polypeptides by any one of several known techniques; for example, ion exchange chromatography, gel filtration chromatography and affinity chromatography. Such techniques may require modification of the protein. For example, one may add a histidine tag to the protein to enable purification on a nickel column.

Persons skilled in the art can use the polypeptides of the invention in a wide variety of ways. For example, one may use them to generate polyclonal or monoclonal antibodies. One may then use such antibodies for immunodetection (e.g., radioimmunoassay, enzyme immunoassay, or immunocytochemistry), immunopurification (e.g., affinity chromatography) of polypeptides from various sources, or immunotherapy.

Persons skilled in the art may make modified OATP polypeptides by known techniques. Such modifications may cause higher or lower activity, permit higher levels of protein production, or simplify purification of the protein.

Such modifications may help identify specific OATP amino acids involved in binding, which in turn may help rational drug design of OATP modulators. One can make amino acid substitutions based on similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine; asparagine, glutamine; serine, threonine; phenylalanine, tyrosine. All such modified polypeptides are included within the scope of the invention.

Preferred analogs include proteins that differ from the novel OATPs of the present invention (or biologically active fragments thereof) by one or more conservative amino acid substitutions or by one or more non-conservative amino acid substitutions, deletions or insertions which do not abolish the biological activity of the analog. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative amino acid substitutions can be taken from the table below.

TABLE 1

Conservative amino acid replacements

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase protein or peptide stability; such analogs may contain, for example, one or more non-peptide bonds (which replace the peptide bonds) in the protein or peptide sequence. Also included are analogs that include residues other than naturally occurring L-amino acids, e.g., D-amino acids or non-naturally occurring or synthetic amino acids, e.g., β or γ amino acids.

The inventors contemplate a number of other variations of the above-described polypeptides. Such variations include salts and esters of the polypeptides, as well as precursors of the aforementioned polypeptides (e.g., having N-terminal substituents such as methionine, N-formylmethionine and leader sequences). The invention includes all such variations.

Method for Detecting Nucleic Acids

The present invention further concerns a method for detecting nucleic acids encoding OATP proteins. In this method, a person of ordinary skill in the art (a) contacts nucleic acids of unknown sequence with a nucleic acid having a sequence complementary to a known coding sequence (e.g., a sequence of at least about 10 nucleotides from, e.g., SEQ ID NO:1, SEQ ID NO:3, SEQ ID NO:5, SEQ ID NO:7, SEQ ID NO:9, or SEQ ID NO:11, particularly the coding regions thereof), wherein the latter nucleic acid has a detectable marker; and (b) determines the presence of marker bound to any of the nucleic acids of unknown sequence. The presence of bound marker indicates the presence of the desired nucleic acids. One can apply this method to detect OATP nucleic acids from other tissues (which may have different regulatory elements) and nucleic acids from other species (e.g., monkey).

Persons of ordinary skill in the art generally know how to obtain nucleic acids to be analyzed in this method. For genomic DNA, one can rapidly freeze tissue, crush the tissue into readily digestible pieces, and incubate the crushed tissue in proteinase K and SDS to degrade most cellular proteins. One can then deproteinize the genomic DNA by successive phenol/chloroform/isoamyl alcohol extractions, recover DNA by ethanol precipitation, dry it and resuspend it in buffer. For RNA, one can lyse cultured cells in 4M guanidinium solution, draw the lysate through a 20-gauge needle, pellet the RNA through a cesium chloride step gradient, and remove the supernatant. The pellet should contain purified RNA.

The detectable marker may be a radioactive ion linked to one of the nucleotides of the complementary nucleic acid. Common radioactive labels are $^{32}P$ and $^{35}S$, although one may also use other labels such as biotin. Persons skilled in the art are aware of various methods to attach the labels to the complementary nucleic acid (e.g., the random primer method for attachment of $^{32}P$ or $^{35}S$).

Persons of ordinary skill in the art generally know how to carry out such a method of detecting nucleic acids. For example, one may perform a Southern or northern blot using a radiolabeled OATP complementary oligonucleotide probe. One can then detect hybridization by autoradiography. Depending on the marker, one may also use other detection methods (e.g., spectrophotometry).

Methods for Detecting OATP Modulators and Compounds Transported by the OATPs of the Present Invention This invention further concerns methods for detecting modulators of the OATPs of the present invention, as well as methods for detecting compounds that are transported by the OATPs of the present invention (e.g., compounds that are transported into the liver that may be used as carriers for other compounds). A screen for OATP modulators entails detecting binding of molecules (e.g., polypeptides, natural products, synthetic compounds) in cells expressing OATP protein. Alternatively, a screen for OATP positive modulators and/or negative modulators entails detecting the augmentation and/or inhibition of transport of a known compound. A screen for OATP-transported compounds entails detecting the transport of molecules (e.g., polypeptides, natural products, synthetic compounds) by an OATP.

Cloning and sequencing of the OATPs of the present invention enables construction of cells useful in screening for natural products and synthetic compounds that bind to, modulate, and/or are transported by OATP activity. A process for detecting OATP modulators requires transforming a suitable vector into compatible host cells as described previously herein. One treats such transformed cells with test substances (e.g., synthetic compounds or natural products), and then measures activity in the presence and absence of the test substance.

OATP Assay

An assay for the measurement of OATP activity is performed as follows: HEK293 cells are plated in Dulbeccos Modified Eagles Medium (DMEM) plus 10% fetal bovine serum plus penicillin and streptomycin, in poly-d-lysine coated dishes and co-transfected with OATP transporter expression plasmids using Lipofectamine Plus (Life Technologies, Inc.). The cells and media are assayed for substrate transport 24 hours later. Alternatively, cell lines engineered to stably express OATPs could be plated and assayed directly without transfection. To measure transport, media is removed and monolayers are assayed in triplicate by washing once in serum-free DMEM and adding the same medium containing [$^3$H]-substrate alone or in the presence of various concentrations of unlabeled test compounds. For OATP2, the [$^3$H]-substrate could be [$^3$H]-pravastatin, [$^3$H]-taurocholate, or [$^3$H]-dehydroepiandrosterone sulfate, or [$^{125}$I]-thyroid hormone (T4). Monolayers are incubated at room temperature for 5 to 10 minutes depending on the transporter. Then the cells are rapidly washed once with ice cold DMEM containing 5% BSA, twice with DMEM plus 0.1% BSA and once with DMEM alone. Cells are lysed in 0.1 N NaOH and a fraction of the lysate is used to determine radiolabel incorporation by liquid scintillation counting, and another is used to determine protein concentration in the lysate using the Bradford assay with BSA as a standard. The transport activity is expressed as moles of substrate transported into cells/mg of cell protein/minute.

Drug Targeting

Also included within the present invention is tissue expression of an OATP of the present invention. The OATPs of the present invention are also useful for targeting drugs to certain organs that express an OATP described herein (e.g., the liver), and for modulating the concentration of endogenous substrates.

For example, the novel organic anion transporter disclosed herein, OATP2, represents a potential therapeutic target due to its ability to modulate the cellular uptake and potential secretion of a several biologically important organic anions, including bile acids and the androgen hormone dehydroepiandrosterone sulfate ("DHEAS"). Furthermore, since OATP2 transports at least one drug (i.e. pravastatin), and other members of this family are known to transport a variety of other xenobiotics, this transporter could be exploited to optimize the delivery of drugs into liver and away from other tissues.

OATP2 is unique among the OATP family, in that it is the only known organic anion transporter that is expressed exclusively in the liver. Thus, drugs optimized for this transporter could be targeted for hepatic delivery with greater selectivity than with any other known transporter. To generalize this approach, it may be possible to identify a small molecule "adaptor" that is efficiently recognized and transported by OATP2 (an OATP2-transported compound) that could be appended to other drugs for hepatic targeting even if the parent compound is not transported by OATP2.

Alternatively, if a therapeutic compound is taken up into the liver entirely or substantially by OATP2, one could inhibit hepatic clearance and thereby elevate circulating concentrations, or increase the compounds half-life in the periphery, by adding a functionality to said compound that disallows transport by OATP2. Likewise, if an endogenous substance utilizes OATP2 for liver uptake and clearance from the circulation, a competitive or non-competitive OATP2 inhibitor could elevate plasma levels of said substance. As an example, DHEAS is an adrenal androgen that declines with age and on the basis of some animal data, it has been suggested that replacement of DHEAS deficiency may stimulate age-related immune deficiencies, increase cognitive function and insulin sensitivity, and maintain bone mass. Inhibiting the hepatic clearance of endogenous DHEAS through blocking its interactions with OATP2 could result in elevated hormone levels in the absence of hormone supplementation.

With the information provided herein, one skilled in the art is able to identify molecules, both naturally occurring and synthetic (including therapeutic drugs), that are transported by the OATPs, e.g., OATP2, disclosed herein. OATPs as a class generally exhibit broad substrate specificity ("polyspecific" transporters). Thus, it is anticipated that many additional substrates of these transporters will be identified.

Gene Therapy

Persons skilled in the art can also use sense and antisense nucleic acid molecules as therapeutic agents for OATP-related indications. One may construct vectors that direct the synthesis of the desired DNA or RNA or formulate the nucleic acid as described in the art.

Several references describe the usefulness of antisense molecule. See Toulme and Helene (1988), Gene 72: 51-8; Inouye (1988), Gene, 72: 25-34; Uhlmann and Peyman (1990), Chemical Reviews 90: 543-584; Biotechnology Newswatch (Jan. 15, 1996), p. 4; Robertson, Nature Biotechnology 15: 209 (1997); Gibbons and Dzau (1996), Science 272: 689-93. One can design them based on genomic DNA and/or cDNA, 5' and 3' flanking control regions, other flanking sequences, intron sequences, and nonclassic Watson and Crick base pairing sequences used in formation of triplex DNA. Such antisense molecules include antisense oligodeoxyribonucleotides, oligoribonucleotides, oligonucleotide analogues, and the like, and may comprise at least about 15 to 25 bases.

Antisense molecules may bind noncovalently or covalently to the OATP DNA or RNA. Such binding could, for example, cleave or facilitate cleavage of OATP DNA or RNA, increase degradation of nuclear or cytoplasmic mRNA, or inhibit transcription, translation, binding of trans-activating factors, or pre-mRNA splicing or processing. Antisense molecules may also contain additional functionalities that increase stability, transport into and out of cells, binding affinity, cleavage of the target molecule, and the like. All of these effects would decrease expression of OATP protein and thus make the antisense molecules useful as OATP modulators.

EXAMPLES

The following examples are included for understanding the present invention and are not intended to limit the scope of Applicants invention, which is defined solely by the claims.

Example 1

Isolation of OATP2, OATP-RP1, OATP-RP2, OATP-RP3, OATP-RP4 and OATP-RP5 Full Length cDNAs and Cloning into Mammalian Expression Vectors Human OATP2 was identified by searching the public EST databases for sequences homologous to human OATP. One EST sequence, Genbank accession number T73863, encoded a partial cDNA with significant sequence identity with OATP. EST sequences encoding partial cDNAs for OATP-RP1, OATP-RP2, OATP-RP3, OATP-RP4, and OATP-RP5 were identified by searching the public EST databases and the Incyte, Inc. EST database for sequences homologous to human OATP. The EST clone IDs corresponding to OATP-RP1 are 820117, 2668489, 1610706, 2972518, and 588148. These clones represent a contig encoding only part of the full length cDNA. The Incyte EST clone IDs corresponding to OATP-RP2 are 1664737 and 2641944. These clones represent a contig encoding only part of the full length cDNA. The Incyte EST clone IDs corresponding to OATP-RP3 are 2493241, 2497845, and 2664024. These clones represent a contig encoding only part of the full length cDNA. The Incyte EST clone IDs corresponding to OATP-RP4 are 1494683 and 1685219. These clones represent a contig encoding only part of the full length cDNA. The Incyte EST clone ID corresponding to OATP-RP5 is 925716. This clone encodes only part of the full length cDNA. Full length clones for each of the above genes were obtained using the Gene Trapper cDNA Positive Selection System (LifeTechnologies, Inc.). In this procedure, a single or multiple oligonucleotides complementary to each of the EST contigs or individual EST sequences, were biotinylated at the 3'-end and used to hybridize to a single-stranded human cDNA library constructed in pCM-VSport2 (LifeTechnologies, Inc.). The sequence of oligonucleotides used for each gene as well as the tissue source of the libraries screened are shown in Table 2.

Two polymorphic positions were identified when sequencing multiple OATP-RP4 cDNA clones. Thus, nucleotide number 713 of SEQ ID NO:7 can be either a C, encoding Leu in SEQ ID NO:8, or a T, encoding a Phe in SEQ ID NO:8. Similarly, nucleotide number 2397 of SEQ ID NO:7 can be either a G, encoding a Gly in SEQ ID NO:8, or a T, encoding a Val in SEQ ID NO:8.

For expression studies, OATP2 cDNA was cloned into the expression vector pCEP4βR, a modified form of pCEP4 (Invitrogen, Inc.) in which the CMV promoter-driven expression cassette has been inverted, and used in transient transfections. To accomplish this, OATP2 cDNA in pCM-VSport2, correponding to nucleotides 59 through 2361 of SEQ ID NO:1, was excised by digestion with KpnI and NotI. This fragment was cloned into KpnI-NotI digested pCEP4βR. This clone, pCEP-OATP2 was used for transient transfection expression studies.

Example 2

Tissue and Cellular Distribution of OATP2, OATP-RP1, OATP-RP2, OATP-RP4, and OATP-RP5

The tissue distribution of OATP2, OATP-RP1, OATP-RP2, OATP-RP4, and OATP-RP5 expression was determined by Northern blotting of poly A+ RNA from a variety of human tissues (FIG. 1). Transporters of this family

TABLE 2

Oligonucleotides used to screen for OATP Full length cDNAs using Gene-Trapper Selection

| Gene | Biotinylated capture oligonucleotide(s) used | Seq ID number of oligonucleotide | Human cDNA library screened |
| --- | --- | --- | --- |
| OATP2 | 5'-ACCCTGTCTAGCAGGTTGCA-3' | 13 | liver |
| OATP-RP1 | 5'-CTGTCGGAGTCTTCAGATG-3' | 14 | brain |
| OATP-RP2 | 5'-TCCATCACAGCCTCCTACGC-3' | 15 | liver |
| OATP-RP3 | 5'-TGCCTCTACTCTGACCCTAG-3' | 16 | heart |
| OATP-RP4 | 5'-GGAGCAGTCATTGACACCAC-3' | 17 | heart |
|  | 5'-TGCTGGGAGTACAACGTGACG-3' | 18 |  |
|  | 5'-ACAAGGAGGATGGACTGCAG-3' | 19 |  |
| OATP-RP5 | 5'-CAGGAATCCCAGCTCCAGTG-3' | 20 | brain |
|  | 5'-GCTACAACCCAACTACTGGC-3' | 21 |  |
|  | 5'-GGGACTAACTGTGATACTGG-3' | 22 |  |

Hybrids between the biotinylated oligonucleotides and single-stranded cDNA were captured on streptavidin-coated paramagnetic beads. After washing, the captured single-stranded cDNA targets was released from the biotinylated oligonucleotides and converted to dsDNA by DNA polymerase using the corresponding unbiotinylated oligonucleotide. Following transformation and plating, several positive clones for each gene were identified by PCR analysis. Full-length cDNA clones were identified by sequencing. In the case of OATP-RP1, a partial cDNA was obtained by the above technique (pSP-RP1A). Another cDNA clone that was part of the OATP-RP1 contig was identified by searching the public EST databases (Genbank accession number AI027850). An EcoRI-NotI fragment of this clone containing the first 477 nucleotides of OATP-RP1 (SEQ ID NO:11) (obtained from Research Genetics, Inc.) was ligated to EcoRI-Not I digested pSP-RP1A to generate the full length sequence.

previously described in the literature, namely human OATP, rat oatp1, rat oatp2 and rat oatp3, are all expressed in liver, kidney and brain. All of the above transport bile acids as well as a variety of other substrates that are specific for subsets of these transporters. In contrast, the expression of OATP2, which also transports bile acids, is very hepato-specific; a major 3.2 kb and several minor hybridizing bands were observed only in RNA from liver and no other tissue. The specific cell types that express this transporter were examined by in situ hybridization of OATP2 riboprobe to human liver samples. Strong hybridization signal was seen localized to hepatocytes throughout the liver lobule with no significant difference in signal intensity among centrilobular, midzonal or periportal regions. No signal was observed in bile ducts, Kupffer cells, or blood vessels, nor in any cell types from human lung (data not shown).

OATP-RP1 is expressed in nearly all tissues tested with highest abundance in skeletal muscle, lung, placenta, and heart. OATP-RP2 is ubiquitously expressed in all tissues tested. OATP-RP4 has a much more restricted pattern of expression with abundant transcipts in skeletal muscle and heart and much less in prostate and thymus. The expression of OATP-RP5 is likewise tissue specific, with brain and testes being the only sites where transcripts were detected.

Example 3

Expression of OATP2 in Transfected Cells

Figure 2C:
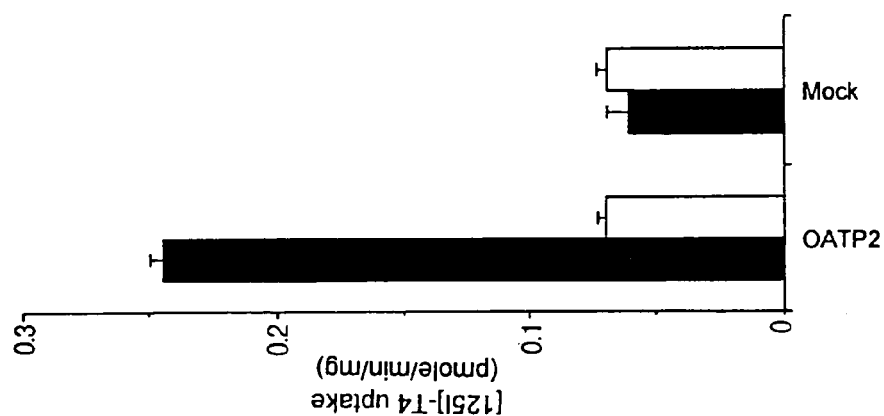
FIG. 2 shows that OATP2 transports pravastatin, dehydroepiandosterone sulfate (DHEAS), taurocholate and thyroid hormone (T).
FIG. 2A shows specific uptake of [$^3$H]-pravastatin and [$^3$H]-DHEAS.
FIG. 2B shows specific uptake of [$^3$H]-taurocholate. Panel 2C shows specific uptake of [$^{125}$I]-thyroid hormone (T4). The uptake of radiolabeled substrate for 5 minutes into cells transfected with pCE-POATP-RP 1 or empty vector (MOCK) was determined in the absence (solid bars) and presence (open bars) of excess unlabeled substrate.
Figure 2B:
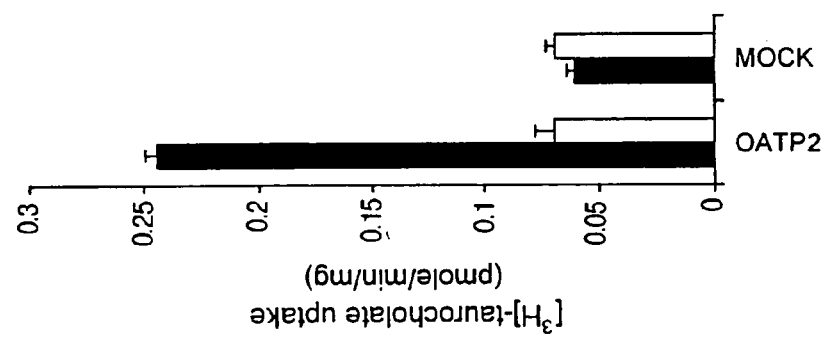
Figure 2A:
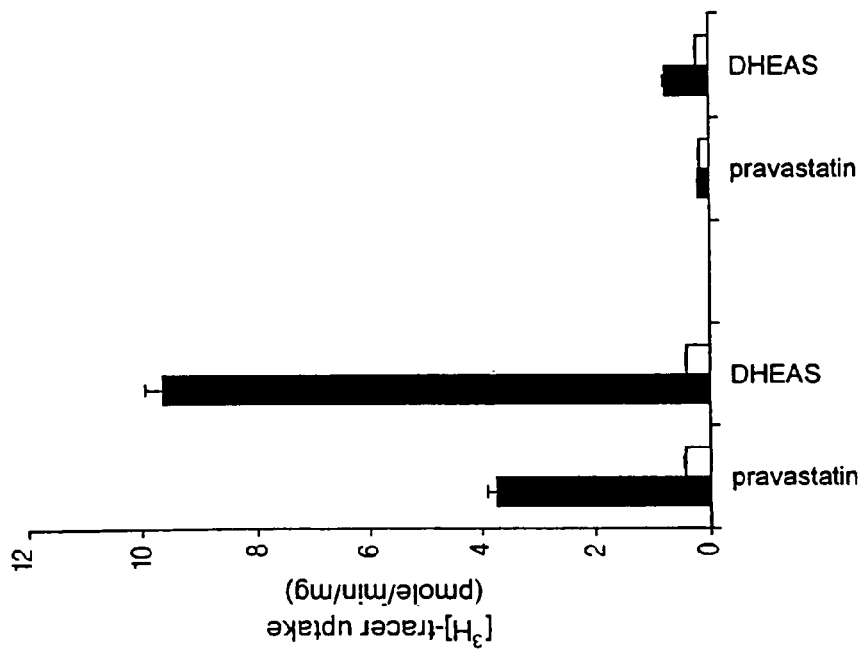

293EBNA cells (Invitrogen, Inc.), an HEK293 cell derivative, were transiently transfected with the OATP2 expression vector pCEP-OATP2, or the pCEP4 vector alone (MOCK) and the transport of [$^3$H]-labeled substrates was determined 24 hours later. FIG. 2A shows specific uptake of [$^3$H]-pravastatin and [$^3$H]-DHEAS. FIGS. 2B and 2C show the specific uptake of [$^3$H]-taurocholate and [125I]-thyroid hormone (T4), respectively. The uptake of radiolabeled substrate for 5 minutes into cells transfected with pCEP-OATP2 or empty vector (MOCK) was determined in the absence (solid bars) and presence (open bars) of excess unlabeled substrate. Thus, OATP2 is a liver specific human transporter of at least some HMG CoA reductase inhibitors, bile acids, adrenal steroids, and thyroid hormone.

We claim:

1. A method of identifying a compound that is transported by an OATP2 (organic anion transport protein 2) protein comprising the amino acid sequence of SEQ ID NO: 2, said method comprising the steps of:
   (a) contacting a cell expressing OATP2 protein with said compound, under conditions which permit the movement of said compound across the cell membrane;
   (b) contacting a control cell that lacks OATP2 protein with said compound, under said conditions of step (a); and
   (c) determining the presence of said compound inside the cell expressing OATP2 protein and inside the cell that lacks OATP2 protein,
   wherein the presence or a greater quantity of said compound inside the cell expressing OATP2 protein as compared to the cell that lacks OATP2 protein indicates said compound is transported by OATP2.

* * * * *